United States Patent
Conn et al.

(10) Patent No.: US 9,382,208 B1
(45) Date of Patent: Jul. 5, 2016

(54) NEGATIVE ALLOSTERIC MODULATORS OF METABOTROPIC GLUTAMATE RECEPTOR 2

(71) Applicant: Vanderbilt University, Nashville, TN (US)

(72) Inventors: P. Jeffrey Conn, Nashville, TN (US); Craig W. Lindsley, Brentwood, TN (US); Kyle A. Emmitte, Spring Hill, TN (US); Andrew S. Felts, Brentwood, TN (US); Katrina A. Bollinger, Murfreesboro, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 15/006,486

(22) Filed: Jan. 26, 2016

Related U.S. Application Data

(60) Provisional application No. 62/107,821, filed on Jan. 26, 2015.

(51) Int. Cl.

| | |
|---|---|
| *C07D 215/233* | (2006.01) |
| *C07D 401/12* | (2006.01) |
| *C07D 417/14* | (2006.01) |
| *C07D 413/06* | (2006.01) |
| *C07D 401/06* | (2006.01) |

(52) U.S. Cl.
CPC .......... *C07D 215/233* (2013.01); *C07D 401/06* (2013.01); *C07D 401/12* (2013.01); *C07D 413/06* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 4,959,363 A | 9/1990 | Wentland | |
| 5,622,967 A | 4/1997 | Dolle et al. | |
| 6,653,307 B2 | 11/2003 | Schnute | |
| 7,879,878 B2 | 2/2011 | Watanuki et al. | |
| 8,802,700 B2 | 8/2014 | Sheth et al. | |
| 2002/0103220 A1 | 8/2002 | Schnute | |
| 2004/0024209 A1 | 2/2004 | Schnute | |

FOREIGN PATENT DOCUMENTS

| | | |
|---|---|---|
| WO | 2006/077851 | 7/2006 |
| WO | 2007/105751 | 9/2007 |
| WO | 2011/072241 | 6/2011 |
| WO | 2013/129622 | 9/2013 |

OTHER PUBLICATIONS

Wicke et al. Arch. Pharm. Chem. Life Sci. 2013, 346, 757-765.*
Chaki, S. et al., "mGlu2/3 and mGlu5 receptors: potential targets for novel antidepressants," Neuropharm. (2013) 66:40-52.
Graybill, T.L. et al., "Inhibition of human erythrocyte calpain I by novel quinolinecarboxamides," Bioorg Med. Chem. Lett (1995) 5(4):387-392.
Kim, S.H. et al., "Proneurogenic group II mGluR antagonist improves learning and reduces anxiety in Alzheimer Abeta oligomer mouse," Mol. Psychiatry (2014) 1-8.
Mistry, S.N. et al., "Synthesis and pharmacological profiling of analogues of benzyl quinolone carboxylic acid (BQCA) as allosteric modulators of the M1 muscarinic receptor," J. Med. Chem. (2013) 56:5151-5172.
Sheu, J-Y. et al., "Synthesis, and antimycobacterial and cytotoxic evaluation of certain fluoroquinolone derivatives," Helvetica Chimica Acta (2003) 86:2481-2489.
Shimazaki, T. e al., "Anxiolytic-like acivity of MGS0039, a potent group II metabotropic glutamate receptor antagonist, in a marble-burying behavior test," Eur. J. Pharmacol. (2004) 501:121-125.
Wentland, M.P. et al., "3-quinolinecarboxamids. A series of novel orally-active antiherpetic agents," J. Med. Chem. (1993) 36:1580-1596.
Yoshimizu, T. et al., "An mGluR2/3 antagonist, MGS0039, exerts antidepressant and anxiolytic effects in behavioral models in rats," Psychopharmacology (2006) 186:587-593.

\* cited by examiner

*Primary Examiner* — Yevegeny Valenrod
(74) *Attorney, Agent, or Firm* — Michael Best & Friedrich LLP

(57) ABSTRACT

Described are negative allosteric modulators of metabotropic glutamate receptor 2 (mGlu$_2$), pharmaceutical compositions including the compounds, and methods of using the compounds and compositions for treating depression, anxiety, obsessive-compulsive disorder, cognitive disorders, Alzheimer's disease, or autism spectrum disorders in a subject.

13 Claims, No Drawings

NEGATIVE ALLOSTERIC MODULATORS OF METABOTROPIC GLUTAMATE RECEPTOR 2

CROSS-REFERENCE TO RELATED APPLICATION

This application is a non-provisional of and claims priority to U.S. Provisional Application No. 62/107,821, filed Jan. 26, 2015, the entire content of which is incorporated herein by reference.

STATEMENT OF GOVERNMENT INTEREST

This invention was made with government support under Grant number 5 U54 MH84659-06 awarded by the National Institute of Mental Health (NIMH). The government has certain rights in the invention.

TECHNICAL FIELD

The present disclosure relates to compounds, compositions, and methods for treating metabotropic glutamate receptor 2 related diseases and/or disorders, such as depression, anxiety, obsessive-compulsive disorder, cognitive disorders, Alzheimer's disease, and autism spectrum disorders.

BACKGROUND

Metabotropic glutamate (mGlu) receptors, a class of G-protein coupled receptor (GPCR) family C, have recently emerged as targets of potential therapeutic value. They bind glutamate, an amino acid that is the most prominent excitatory neurotransmitter in the human central nervous system (CNS). mGlus are known to activate biochemical cascades, leading to the modification of other proteins. For example, this can lead to changes in a synapse's excitability by presynaptic inhibition of neurotransmission, or modulation and even induction of postsynaptic responses.

Metabotropic glutamate receptor 2 (mGlu$_2$) is one of eight mGlus that have been identified, and, along with mGlu$_3$, is classified as a group II mGlu. Group II mGlus play an important role is synaptic plasticity, which directly effects cognitive function (including learning and memory), among other things. The effects of group II mGlus occur primarily presynaptically via their inhibition of glutamate release. These effects can also be due to the inhibition of non-vesicular glutamate release from glia. However, group II receptors are known to also reduce the activity of postsynaptic potentials, both excitatory and inhibitory, in the cortex.

Dysfunction of mGlu$_2$ has been implicated in many diseases and/or disorders. Hence, targeting mGlu$_2$ activity has been the subject of much investigation. Several reports have highlighted its link to a variety of diseases, such as depression, anxiety, obsessive-compulsive disorder, cognitive disorders, Alzheimer's disease, and autism spectrum disorders. Accordingly, there exists a need for selective modulators of mGlu$_2$.

SUMMARY OF THE INVENTION

In one aspect, disclosed are compounds of formula (I),

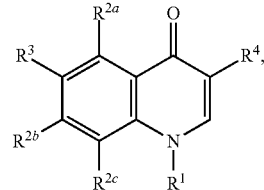

or a pharmaceutically acceptable salt thereof, wherein
$R^1$ is aryl, heteroaryl, heterocycle, or cycloalkyl;
$R^{2a}$, $R^{2b}$, and $R^{2c}$ are each independently selected from hydrogen, halogen, $C_1$-$C_4$ alkyl, $C_1$-$C_4$ alkoxy, $C_1$-$C_4$ haloalkyl, and $C_1$-$C_4$ haloalkoxy;
$R^3$ is —X—(CR$^{8a}$R$^{8b}$)$_p$—Z—(CR$^{8c}$R$^{8d}$)$_q$—N(R$^{7a}$)(R$^{7b}$), —X—(CR$^{8a}$R$^{8b}$)$_p$—Z—(CR$^{8c}$R$^{8d}$)$_q$—Y-A, -A'—X—(CR$^{8a}$R$^{8b}$)$_p$—N(R$^{7a}$)(R$^{7b}$), or -A'—X—(CR$^{8a}$R$^{8b}$)$_p$—Y-A;
p is 0-2;
q is 0-2;
X, Y, and Z are each independently selected from a bond, CR$^{8e}$R$^{8f}$, O, S, NR$^{10}$, —C(O)—, —O—C(O)—, —C(O)—O—, —O—C(O)—NR$^{10}$—, —C(O)—NR$^{10}$—, —NR$^{10}$—C(O)—, —NR$^{10}$—C(O)—O—, —NR$^{10}$—C(O)—NR$^{10}$—, —NR$^{10}$—SO$_2$—, and —SO$_2$—;
$R^{7a}$ and $R^{7b}$ are each independently selected from $C_1$-$C_7$ alkyl, $C_1$-$C_7$ haloalkyl, cycloalkyl, $C_1$-$C_7$ heteroalkyl, and heterocycle, or $R^{7a}$ and $R^{7b}$ together with the nitrogen atom to which they attach form a heterocycle;
$R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy;
$R^{10}$ at each occurrence is independently selected from hydrogen, $C_1$-$C_4$ alkyl, and $C_1$-$C_4$ haloalkyl;
A is aryl, heteroaryl, cycloalkyl, or heterocycle;
A' is aryl, heteroaryl, cycloalkyl, or heterocycle; and
$R^4$ is —CONH$_2$ or cyano;
wherein said aryl, heteroaryl, cycloalkyl, and heterocycle, at each occurrence, are independently substituted or unsubstituted.

Also disclosed are pharmaceutical compositions comprising the compounds, methods of making the compounds, and methods of using the compounds for treatment of metabotropic glutamate receptor 2 related diseases and/or disorders.

DETAILED DESCRIPTION

Disclosed herein are negative allosteric modulators (NAMs) of mGlu$_2$. The modulators can have formula (I). Compounds of formula (I) may exhibit selectivity for mGlu$_2$ over other mGlu receptors. Compounds of formula (I) can be used to treat or prevent diseases and disorders associated with mGlu$_2$ by modulating mGlu$_2$ activity. mGlu$_2$ has been implicated in a number of different diseases and disorders including, but not limited to, depression, anxiety, obsessive-compulsive disorder, cognitive disorders, Alzheimer's disease, and autism spectrum disorders.

Since the orthosteric binding sites of the mGlu isoforms are highly conserved, very few selective modulators of the mGlus that bind at the orthosteric site have been identified. One strategy to selectively bind and modulate the mGlus includes identifying allosteric sites which may be amenable to modulation by a small molecule. In particular, negative allosteric modulation of mGlu$_2$ can result in inhibition of processes governed by mGlu$_2$ and provide therapeutic benefits for disorders caused by mGlu$_2$ dysfunction.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety.

The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference. The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 10 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkoxyalkyl" as used herein, refers to an alkoxy group, as defined herein, appended to the parent molecular moiety through an alkyl group, as defined herein.

The term "alkylene", as used herein, refers to a divalent group derived from a straight or branched chain hydrocarbon of 1 to 10 carbon atoms, for example, of 2 to 5 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "aryl" as used herein, refers to a phenyl group, or a bicyclic fused ring system. Bicyclic fused ring systems are exemplified by a phenyl group appended to the parent molecular moiety and fused to a cycloalkyl group, as defined herein, a phenyl group, a heteroaryl group, as defined herein, or a heterocycle, as defined herein. Representative examples of aryl include, but are not limited to, indolyl, naphthyl, phenyl, quinolinyl and tetrahydroquinolinyl.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "heteroalkyl" as used herein, means an alkyl group, as defined herein, in which one or more of the carbon atoms has been replaced by a heteroatom selected from S, O, P and N. Representative examples of heteroalkyls include, but are not limited to, alkyl ethers, secondary and tertiary alkyl amines, amides, and alkyl sulfides.

The term "heteroaryl" as used herein, refers to an aromatic monocyclic ring or an aromatic bicyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. Representative examples of heteroaryl include, but are not limited to, indolyl, pyridinyl (including pyridin-2-yl, pyridin-3-yl, pyridin-4-yl), pyrimidinyl, thiazolyl, and quinolinyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" or "hydroxy" as used herein, means an —OH group.

In some instances, the number of carbon atoms in a hydrocarbyl substituent (e.g., alkyl or cycloalkyl) is indicated by the prefix "$C_x$-$C_y$-", wherein x is the minimum and y is the maximum number of carbon atoms in the substituent. Thus, for example, "$C_1$-$C_3$-alkyl" refers to an alkyl substituent containing from 1 to 3 carbon atoms.

The term "substituents" refers to a group "substituted" on an aryl, heteroaryl, phenyl or pyridinyl group at any atom of that group. Any atom can be substituted.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

In one aspect, disclosed is a compound of formula (I):

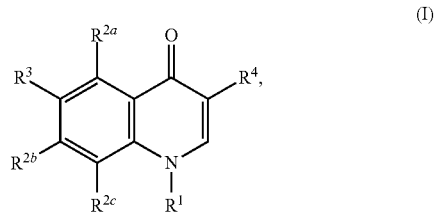

(I)

or a pharmaceutically acceptable salt thereof, wherein $R^1$ is aryl, heteroaryl, heterocycle, or cycloalkyl; $R^{2a}$, $R^{2b}$, and $R^{2c}$ are each independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^3$ is —X—$(CR^{8a}R^{8b})_p$—Z—$(CR^{8c}R^{8d})_q$—N$(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; p is 0-2; q is 0-2; X, Y, and Z are each independently selected from a bond, $CR^{8e}R^{8f}$, O, S, $NR^{10}$, —C(O)—, —O—C(O)—, —C(O)—O—, —O—C(O)—$NR^{10}$—, —C(O)—$NR^{10}$—, —$NR^{10}$—C(O)—, —$NR^{10}$—C(O)—O—, —$NR^{10}$—C(O)—NR—, —$NR^{10}$—$SO_2$—, and —$SO_2$—; $R^{7a}$ and $R^{7b}$ are each independently selected from $C_1$-$C_7$ alkyl, $C_1$-$C_7$ haloalkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$ or cyano; wherein said aryl, heteroaryl, cycloalkyl, and heterocycle, at each occurrence, are independently substituted or unsubstituted.

In certain embodiments, $R^1$ is aryl, heteroaryl, heterocycle, or cycloalkyl; $R^{2a}$, $R^{2b}$, and $R^{2c}$ are each independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; q is 0-2; X, Y, and Z are each independently selected from a bond, $CR^{8e}R^{8f}$, O, S, $NR^{10}$, —C(O)—, —O—C(O)—, —C(O)—O—, —O—C(O)—$NR^{10}$—, —C(O)—$NR^{10}$—, —$NR^{10}$—C(O)—, —$NR^{10}$—C(O)—O—, —$NR^{10}$—C(O)—NR—, —$NR^{10}$—$SO_2$—, and —$SO_2$—; $R^{7a}$ and $R^{7b}$ are each independently selected from $C_1$-$C_7$ alkyl, $C_1$-$C_7$ haloalkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$ or cyano; wherein said aryl, heteroaryl, cycloalkyl, and heterocycle, at each occurrence, are each independently unsubstituted or substituted with 1, 2, 3, 4, 5, 6, or 7 functional groups independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, $R^1$ is aryl or heteroaryl.

In certain embodiments, $R^1$ is aryl or heteroaryl, substituted with 0-3 substituents independently selected from fluoro, chloro, cyano, $C_1$-$C_6$ alkyl, $C_1$-$C_6$ fluoroalkyl, $C_1$-$C_6$ alkoxyalkyl, cyclopropyl, fluorocyclopropyl, $OR^5$, and $NR^{6a}R^{6b}$; wherein $R^5$ is hydrogen, $C_1$-$C_6$ alkyl or $C_1$-$C_6$ fluoroalkyl; and $R^{6a}$ and $R^{6b}$ are each independently hydrogen, $C_1$-$C_6$ alkyl, cyclopropyl, cyclobutyl, or $C_1$-$C_6$ heteroalkyl; or $R^{6a}$ and $R^{6b}$ together with the nitrogen atom to which they are attach form a heterocycle; wherein each $R^{6a}$ and $R^{6b}$ are substituted with 0-3 fluorine atoms.

In certain embodiments, $R^1$ is aryl substituted with 0-2 substituents independently selected from fluoro, chloro, $C_1$-$C_3$ alkyl, $C_1$-$C_3$ fluoroalkyl, $C_1$-$C_3$ alkoxyalkyl, and $OR^5$; wherein $R^5$ is hydrogen, $C_1$-$C_3$ alkyl, or $C_1$-$C_3$ fluoroalkyl.

In certain embodiments, $R^1$ is heteroaryl substituted with 0-2 substituents independently selected from fluoro, chloro, $C_1$-$C_3$ alkyl, $C_1$-$C_3$ fluoroalkyl, and $C_1$-$C_3$ alkoxyalkyl. In certain embodiments, $R^1$ is heteroaryl substituted with 0-1 substituents selected from $C_1$-$C_3$ alkyl. In certain embodiments, $R^1$ is isothiazolyl substituted with 0-1 substituents selected from $C_1$-$C_3$ alkyl.

In certain embodiments, $R^1$ is phenyl substituted with 0-2 substituents independently selected from fluoro and methoxy.

In certain embodiments, $R^1$ is phenyl. In certain embodiments, $R^1$ is pyridyl. In certain embodiments, $R^1$ is isothiazolyl. In certain embodiments, $R^1$ is thiazolyl. In certain embodiments, $R^1$ is pyrazolyl. In certain embodiments, $R^1$ is imidazolyl. In certain embodiments, $R^1$ is pyrrolyl. In certain embodiments, $R^1$ is thienyl. In certain embodiments, $R^1$ is furanyl. In certain embodiments, $R^1$ is benzofuranyl. In certain embodiments, $R^1$ is benzothienyl. In certain embodiments, $R^1$ is indolyl. In certain embodiments, $R^1$ is naphthyl. In certain embodiments, $R^1$ is quinolinyl. In certain embodiments, $R^1$ is tetrahydroquinolinyl. In certain embodiments, $R^1$ is pyrimidinyl. In certain embodiments, $R^1$ is pyridazinyl. In certain embodiments, $R^1$ is pyrazinyl. In certain embodiments, $R^1$ is oxazolyl. In certain embodiments, $R^1$ is isoxazolyl.

In certain embodiments, $R^{2a}$, $R^{2b}$, and $R^{2c}$ are each independently hydrogen, fluoro, or chloro. In certain embodiments, $R^{2a}$, $R^{2b}$, and $R^{2c}$ are each hydrogen. In certain embodiments, $R^{2a}$ and $R^{2b}$ are hydrogen, and $R^{2c}$ is fluoro. In certain embodiments, $R^{2a}$ is hydrogen, and $R^{2b}$ and $R^{2c}$ are each independently hydrogen or fluoro.

In certain embodiments, $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl or heterocycle; and A' is aryl, heteroaryl, cycloalkyl, or heterocycle.

In certain embodiments, $R^3$ is —X—$(CR^{8a}R^{8b})_p$—$(CR^{8c}R^{8d})_q$—$N(R^{7a})(R^{7b})$ or —X—$(CR^{8a}R^{8b})_p$—$(CR^{8c}R^{8d})_q$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; and A is aryl, heteroaryl, cycloalkyl or heterocycle.

In certain embodiments, $R^3$ is

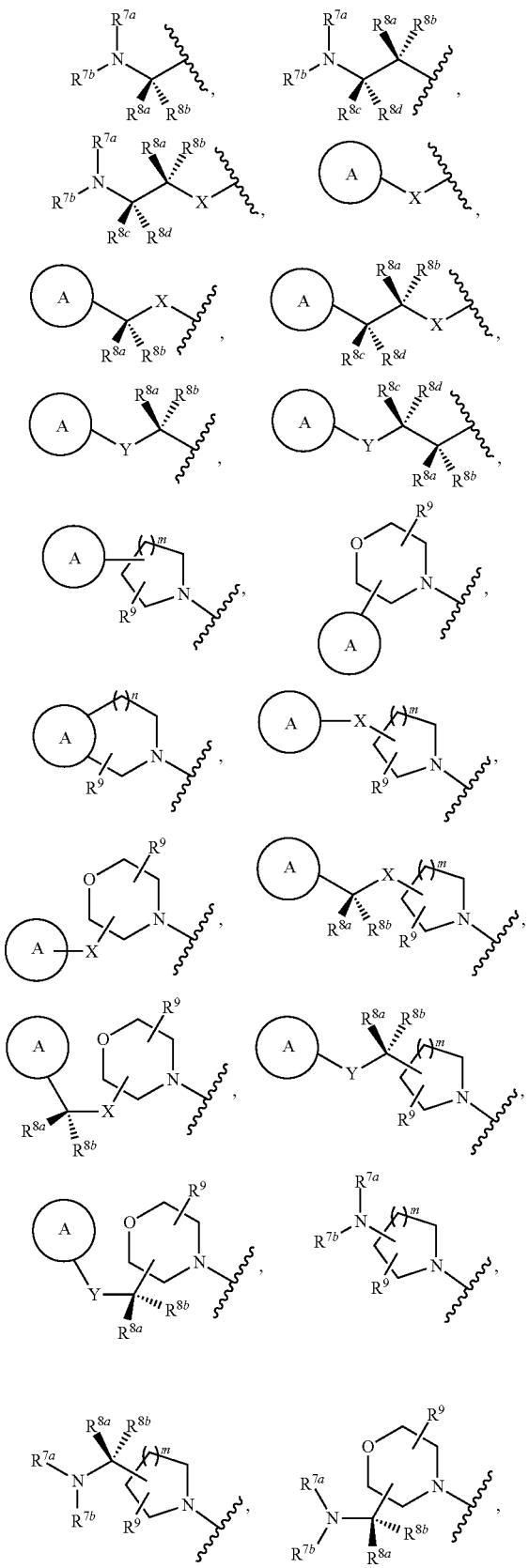

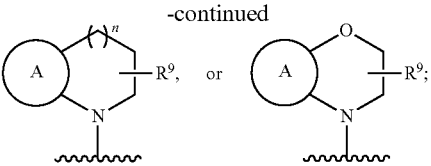

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; n is 0-2; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms.

In certain embodiments, $R^3$ is

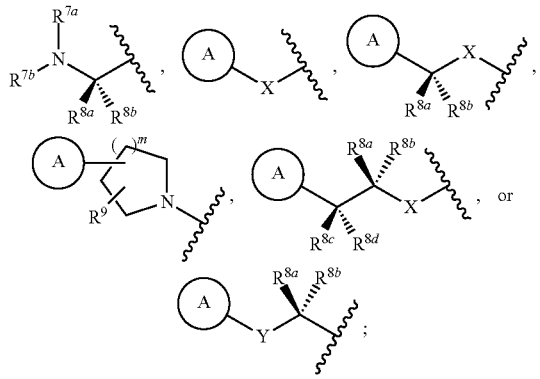

wherein X, Y, $R^{7a}$, $R^{7b}$, $R^{8a}$, $R^{8b}$, $R^{8c}$, $R^{8d}$, $R^9$, m and A are as defined in any of the previous embodiments.

In certain embodiments, $R^3$ is

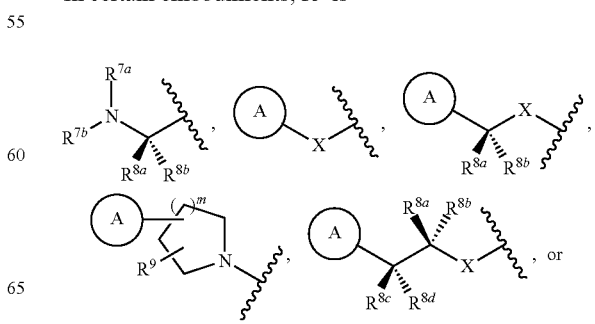

-continued

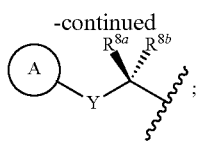

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; n is 0-2; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms.

In certain embodiments, $R^3$ is —X—$(CR^{8a}R^{8b})_p$—Z—$(CR^{8c}R^{8d})_q$—$N(R^{7a})(R^{7b})$, provided that when q=0, Z is not O, S, $NR^{10}$, —C(O)—O—, —O—C(O)—$NR^{10}$—, —C(O)—$NR^{10}$—, —$NR^{10}$—C(O)—O—, or —$NR^{10}$—C(O)—$NR^{10}$—.

In certain embodiments, $R^3$ is —X—$(CR^{8a}R^{8b})_p$—Z—$(CR^{8c}R^{8d})_q$—$N(R^{7a})(R^{7b})$, provided that when p=0, then Z and X do not form an O—O, N—N, O—N, or N—O bond.

In certain embodiments, $R^3$ is —X—$(CR^{8a}R^{8b})_p$—Z—$(CR^{8c}R^{8d})_q$—Y-A, provided that when q=0, Z and Y do not form an O—O, N—N, O—N, or N—O bond.

In certain embodiments, $R^3$ is —X—$(CR^{8a}R^{8b})_p$—Z—$(CR^{8c}R^{8d})_q$—Y-A, provided that when p=0, Z and X do not form an O—O, N—N, O—N, or N—O bond.

In certain embodiments, $R^3$ is -A'—X—$(CR^{8a}R^{8b})_p$—N$(R^{7a})(R^{7b})$, provided that when p=0, X is not O, S, $NR^{10}$, —C(O)—O—, —O—C(O)—$NR^{10}$—, —C(O)—$NR^{10}$—, —$NR^{10}$—C(O)—O—, or —$NR^{10}$—C(O)—$NR^{10}$—.

In certain embodiments, $R^3$ is -A'—X—$(CR^{8a}R^{8b})_p$—Y-A, provided that when p=0, X and Y do not form an O—O, N—N, O—N, or N—O bond.

In certain embodiments, A' is aryl, heteroaryl, cycloalkyl, or heterocycle. In certain embodiments, A' is cycloalkyl or heterocycle.

In certain embodiments, A' is a monocyclic heteroaryl. In certain embodiments, A' is a monocyclic heterocycle. In certain embodiments, A' is bicyclic heterocycle. In certain embodiments, A' is a monocyclic heterocycle fused to a phenyl group. In certain embodiments, A' is a monocyclic heterocycle fused to a monocyclic cycloalkenyl. In certain embodiments, A' is a monocyclic heterocycle fused to a monocyclic heterocycle. In certain embodiments, A' is a spiro heterocycle. In certain embodiments, A' is a bridged monocyclic heterocycle ring system. In certain embodiments, A' is a tricyclic heterocycle. In certain embodiments, A' is a bicyclic heterocycle fused to a phenyl group. In certain embodiments, A' is a bicyclic heterocycle fused to a monocyclic cycloalkyl. In certain embodiments, A' is a bicyclic heterocycle fused to a monocyclic cycloalkenyl. In certain embodiments, A' is a bicyclic heterocycle fused to a monocyclic heterocycle. In certain embodiments, A' is a bicyclic heterocycle in which two non-adjacent atoms of the bicyclic ring are linked by an alkylene bridge. In certain embodiments, A' is an aromatic monocyclic ring. In certain embodiments, A' is an aromatic bicyclic ring system. In certain embodiments, A' is a cycloalkyl. In certain embodiments, A' is unsubstituted. In certain embodiments, A' is substituted with 1, 2, 3, 4, 5, 6, or 7 functional groups independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, A is a monocyclic heteroaryl. In certain embodiments, A is a monocyclic heterocycle. In certain embodiments, A is bicyclic heterocycle. In certain embodiments, A is a monocyclic heterocycle fused to a phenyl group. In certain embodiments, A is a monocyclic heterocycle fused to a monocyclic cycloalkenyl. In certain embodiments, A is a monocyclic heterocycle fused to a monocyclic heterocycle. In certain embodiments, A is a spiro heterocycle. In certain embodiments, A is a bridged monocyclic heterocycle ring system. In certain embodiments, A is a tricyclic heterocycle. In certain embodiments, A is a bicyclic heterocycle fused to a phenyl group. In certain embodiments, A is a bicyclic heterocycle fused to a monocyclic cycloalkyl. In certain embodiments, A is a bicyclic heterocycle fused to a monocyclic cycloalkenyl. In certain embodiments, A is a bicyclic heterocycle fused to a monocyclic heterocycle. In certain embodiments, A is a bicyclic heterocycle in which two non-adjacent atoms of the bicyclic ring are linked by an alkylene bridge. In certain embodiments, A is an aromatic monocyclic ring. In certain embodiments, A is an aromatic bicyclic ring system. In certain embodiments, A is a cycloalkyl. In certain embodiments, A is unsubstituted. In certain embodiments, A is substituted with 1, 2, 3, 4, 5, 6, or 7 functional groups independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

In certain embodiments, $R^3$ is a monocyclic heteroaryl. In certain embodiments, $R^3$ is a monocyclic heterocycle. In certain embodiments, $R^3$ is bicyclic heterocycle. In certain embodiments, $R^3$ is a monocyclic heterocycle fused to a phenyl group. In certain embodiments, $R^3$ is a monocyclic heterocycle fused to a monocyclic cycloalkenyl. In certain embodiments, $R^3$ is a monocyclic heterocycle fused to a monocyclic heterocycle. In certain embodiments, $R^3$ is a spiro heterocycle. In certain embodiments, $R^3$ is a bridged monocyclic heterocycle ring system. In certain embodiments, $R^3$ is a tricyclic heterocycle. In certain embodiments, $R^3$ is a bicyclic heterocycle fused to a phenyl group. In certain embodiments, $R^3$ is a bicyclic heterocycle fused to a monocyclic cycloalkyl. In certain embodiments, $R^3$ is a bicyclic heterocycle fused to a monocyclic cycloalkenyl. In certain embodiments, $R^3$ is a bicyclic heterocycle fused to a monocyclic heterocycle. In certain embodiments, $R^3$ is a bicyclic heterocycle in which two non-adjacent atoms of the bicyclic ring are linked by an alkylene bridge. In certain embodiments, $R^3$ is an aromatic monocyclic ring. In certain embodiments, $R^3$ is an aromatic bicyclic ring system. In certain embodiments, $R^3$ is unsubstituted. In certain embodiments, $R^3$ is substituted with 1-7 functional groups independently selected from the group consisting of halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinyl amino, sulfonyl, alkylsulfonyl, arylsulfonyl, aminosulfonyl, sulfinyl, —COOH, ketone, amide, carbamate, and acyl.

In certain embodiments, $R^3$ is

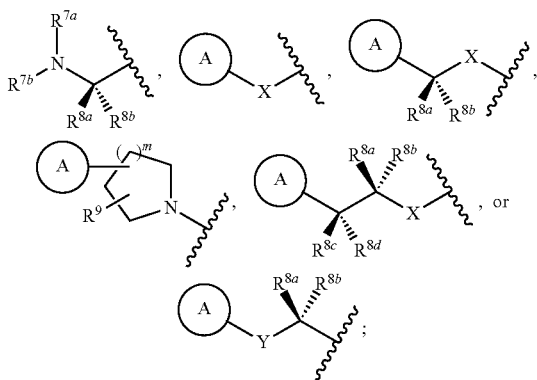

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_3$ alkyl and $C_3$-$C_5$ cycloalkyl, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$ are each independently selected from hydrogen and methyl; $R^9$ at each occurrence is independently selected from pyridyl and morpholinyl; wherein 0-1 $R^9$ groups are present in each $R^3$; m is 0 -1; $R^{10}$ is hydrogen or $C_1$-$C_3$ alkyl; A is pyridyl, pyrimidinyl, morpholinyl, pyrrolidinyl, piperidinyl, pyrazolinyl, tetrahydropyranyl, piperazinyl, 1,1-dioxothiomorpholinyl, 1, -dioxo-1,4-thiazepanyl, 1,4-diazepanyl, 1,4-thiazepanyl, 1,4-oxazepanyl, azepanyl, 2-azaspiro[3.3]heptan-2-yl, decahydroquinolyl; wherein A is substituted with 0-2 substituents independently selected from fluoro, chloro, cyano, methyl, —$CH_2CF_3$, methoxy, $SO_2Me$, acyl, and cyclopropyl.

In certain embodiments, $R^4$ is —$CONH_2$. In certain embodiments, $R^4$ is cyano.

In certain embodiments, $R^1$ is aryl, heteroaryl, heterocycle, or cycloalkyl; $R^{2a}$, $R^{2b}$, and $R^{2c}$ are each independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; p is 0-2; q is 0-2; X, Y, and Z are each independently selected from a bond, $CR^{8e}R^{8f}$, O, S, $NR^{10}$, —C(O)—, —O—C(O)—, —C(O)—O—, —O—C(O)—$NR^{10}$—, —C(O)—$NR^{10}$—, —$NR^{10}$—C(O)—, —$NR^{10}$—C(O)—O—, —$NR^{10}$—C(O)—$NR^{10}$—, —$NR^{10}$—$SO_2$—, and —$SO_2$—; $R^{7a}$ and $R^{7b}$ are each independently selected from $C_1$-$C_7$ alkyl, $C_1$-$C_7$ haloalkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl or heteroaryl; $R^{2a}$, $R^{2b}$, and $R^{2c}$ are each independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; p is 0-2; q is 0-2; X, Y, and Z are each independently selected from a bond, $CR^{8e}R^{8f}$, O, S, $NR^{10}$, —C(O)—, —O—C(O)—, —C(O)—O—, —O—C(O)—$NR^{10}$—, —C(O)—$NR^{10}$—, —$NR^{10}$—C(O)—, —$NR^{10}$—C(O)—O—, —$NR^{10}$—C(O)—$NR^{10}$—, —$NR^{10}$—$SO_2$—, and —$SO_2$—; $R^{7a}$ and $R^{7b}$ are each independently selected from $C_1$-$C_7$ alkyl, $C_1$-$C_7$ haloalkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl or heteroaryl, substituted with 0-3 substituents independently selected from fluoro, chloro, cyano, $C_1$-$C_6$ alkyl, $C_1$-$C_6$ fluoroalkyl, $C_1$-$C_6$ alkoxyalkyl, cyclopropyl, fluorocyclopropyl, $OR^5$, and $NR^{6a}R^{6b}$; wherein $R^5$ is hydrogen, $C_1$-$C_6$ alkyl or $C_1$-$C_6$ fluoroalkyl; and $R^{6a}$ and $R^{6b}$ are each independently hydrogen, $C_1$-$C_6$ alkyl, cyclopropyl, cyclobutyl, or $C_1$-$C_6$ heteroalkyl; or $R^{6a}$ and $R^{6b}$ together with the nitrogen atom to which they are attach form a heterocycle; wherein each $R^{6a}$ and $R^{6b}$ are substituted with 0-3 fluorine atoms; $R^{2a}$, $R^{2b}$, and $R^{2c}$ are each independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^3$ is —X—$(CR^{8a}R^{8b})_p$—Z—$(CR^{8c}R^{8d})_q$ $N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; p is 0-2; q is 0-2; X, Y, and Z are each independently selected from a bond, $CR^{8e}R^{8f}$, O, S, $NR^{10}$, —C(O)—, —O—C(O)—, —C(O)—O—, —O—C(O)—$NR^{10}$—, —C(O)—$NR^{10}$—, —$NR^{10}$—C(O)—, —$NR^{10}$—C(O)—O—, —$NR^{10}$—C(O)—$NR^{10}$—, —$NR^{10}$—$SO_2$—, and —$SO_2$—; $R^{7a}$ and $R^{7b}$ are each independently selected from $C_1$-$C_7$ alkyl, $C_1$-$C_7$ haloalkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl substituted with 0-2 substituents independently selected from fluoro, chloro, $C_1$-$C_3$ alkyl, $C_1$-$C_3$ fluoroalkyl, $C_1$-$C_3$ alkoxyalkyl, and OR$^5$; wherein R$^5$ is hydrogen, $C_1$-$C_3$ alkyl, or $C_1$-$C_3$ fluoroalkyl; R$^{2a}$, R$^{2b}$, and R$^{2c}$ are each independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; R$^3$ is —X—(CR$^{8a}$R$^{8b}$)$_p$—Z—(CR$^{8c}$R$^{8d}$)$_q$—N(R$^{7a}$)(R$^{7b}$), —X—(CR$^{8a}$R$^{8b}$)$_p$—Z—(CR$^{8c}$R$^{8d}$)$_q$—Y-A, -A'—X—(CR$^{8a}$R$^{8b}$)$_p$—N(R$^{7a}$)(R$^{7b}$), or -A'—X—(CR$^{8a}$R$^{8b}$)$_p$—Y-A; p is 0-2; q is 0-2; X, Y, and Z are each independently selected from a bond, CR$^{8e}$R$^{8f}$, O, S, NR$^{10}$, —C(O)—, —O—C(O)—, —C(O)—O—, —O—C(O)—NR$^{10}$—, —C(O)—NR$^{10}$—, —NR$^{10}$—C(O)—, —NR$^{10}$—C(O)—O—, —NR$^{10}$—C(O)—NR$^{10}$—, —NR$^{10}$—SO$_2$—, and —SO$_2$—; R$^{7a}$ and R$^{7b}$ are each independently selected from $C_1$-$C_7$ alkyl, $C_1$-$C_7$ haloalkyl, cycloalkyl, $C_1$-$C_7$ heteroalkyl, and heterocycle, or R$^{7a}$ and R$^{7b}$ together with the nitrogen atom to which they attach form a heterocycle; R$^{8a}$, R$^{8b}$, R$^{8c}$, R$^{8d}$, R$^{8e}$ and R$^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; R$^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and R$^4$ is —CONH$_2$.

In certain embodiments, R$^1$ is heteroaryl substituted with 0-2 substituents independently selected from fluoro, chloro, $C_1$-$C_3$ alkyl, $C_1$-$C_3$ fluoroalkyl, and $C_1$-$C_3$ alkoxyalkyl; R$^{2a}$, R$^{2b}$, and R$^{2c}$ are each independently selected from hydrogen, halogen, $C_1$-$C_4$ alkyl, $C_1$-$C_4$ alkoxy, $C_1$-$C_4$ haloalkyl, and $C_1$-$C_4$ haloalkoxy R$^3$ is —X—(CR$^{8a}$R$^{8b}$)$_p$—Z—(CR$^{8c}$R$^{8d}$)$_q$—N(R$^{7a}$)(R$^{7b}$), —X—(CR$^{8a}$R$^{8b}$)$_p$—Z—(CR$^{8c}$R$^{8d}$)$_q$—Y-A, -A'—X—(CR$^{8a}$R$^{8b}$)$_p$—N(R$^{7a}$)(R$^{7b}$), or -A'—X—(CR$^{8a}$R$^{8b}$)$_p$—Y-A; p is 0-2; q is 0-2; X, Y, and Z are each independently selected from a bond, CR$^{8e}$R$^{8f}$, O, S, NR$^{10}$, —C(O)—, —O—C(O)—, —C(O)—O—, —O—C(O)—NR$^{10}$—, —C(O)—NR$^{10}$—, —NR$^{10}$—C(O)—, —NR$^{10}$—C(O)—O—, —NR$^{10}$—C(O)—NR$^{10}$—, —NR$^{10}$—SO$_2$—, and —SO$_2$—; R$^{7a}$ and R$^{7b}$ are each independently selected from $C_1$-$C_7$ alkyl, $C_1$-$C_7$ haloalkyl, cycloalkyl, $C_1$-$C_7$ heteroalkyl, and heterocycle, or R$^{7a}$ and R$^{7b}$ together with the nitrogen atom to which they attach form a heterocycle; R$^{8a}$, R$^{8b}$, R$^{8c}$, R$^{8d}$, R$^{8e}$ and R$^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; R$^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and R$^4$ is —CONH$_2$.

In certain embodiments, R$^1$ is aryl, heteroaryl, heterocycle, or cycloalkyl; R$^{2a}$, R$^{2b}$, and R$^{2c}$ are each independently hydrogen, fluoro, or chloro; R$^3$ is —X—(CR$^{8a}$R$^{8b}$)$_p$—Z—(CR$^{8c}$R$^{8d}$)$_q$—N(CR$^{7a}$R$^{7b}$), —X—(CR$^{8a}$R$^{8b}$)$_p$—Z—(CR$^{8c}$R$^{8d}$)$_q$—Y-A, -A'—X—(CR$^{8a}$R$^{8b}$)$_p$—N(R$^{7a}$)(R$^{7b}$), or -A'—X—(CR$^{8a}$R$^{8b}$)$_p$—Y-A; p is 0-2; q is 0-2; X, Y, and Z are each independently selected from a bond, CR$^{8e}$R$^{8f}$, O, S, NR$^{10}$, —C(O)—, —O—C(O)—, —C(O)—O—, —O—C(O)—NR$^{10}$—, —C(O)—NR$^{10}$—, —NR$^{10}$—C(O)—, —NR$^{10}$—C(O)—O—, —NR$^{10}$—C(O)—NR$^{10}$—, —NR$^{10}$—SO$_2$—, and —SO$_2$—; R$^{7a}$ and R$^{7b}$ are each independently selected from $C_1$-$C_7$ alkyl, $C_1$-$C_7$ haloalkyl, cycloalkyl, $C_1$-$C_7$ heteroalkyl, and heterocycle, or R$^{7a}$ and R$^{7b}$ together with the nitrogen atom to which they attach form a heterocycle; R$^{8a}$, R$^{8b}$, R$^{8c}$, R$^{8d}$, R$^{8e}$ and R$^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; R$^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and R$^4$ is —CONH$_2$.

In certain embodiments, R$^1$ is aryl or heteroaryl; R$^{2a}$, R$^{2b}$, and R$^{2c}$ are each independently hydrogen, fluoro, or chloro; R$^3$ is —X—(CR$^{8a}$R$^{8b}$)$_p$—Z—(CR$^{8c}$R$^{8d}$)$_q$—N(R$^{7a}$)(R$^{7b}$), —X—(CR$^{8a}$R$^{8b}$)$_p$—Z—(CR$^{8c}$R$^{8d}$)$_q$—Y-A, -A'—X—(CR$^{8a}$R$^{8b}$)$_p$—N(R$^{7a}$)(R$^{7b}$), or -A'—X—(CR$^{8a}$R$^{8b}$)$_p$—Y-A; p is 0-2; q is 0-2; X, Y, and Z are each independently selected from a bond, CR$^{8e}$R$^{8f}$, O, S, NR$^{10}$, —C(O)—, —O—C(O)—, —C(O)—O—, —O—C(O)—NR$^{10}$—, —C(O)—NR$^{10}$—, —NR$^{10}$—C(O)—, —NR$^{10}$—C(O)—O—, —NR$^{10}$—C(O)—NR$^{10}$—, —NR$^{10}$—SO$_2$—, and —SO$_2$—; R$^{7a}$ and R$^{7b}$ are each independently selected from $C_1$-$C_7$ alkyl, $C_1$-$C_7$ haloalkyl, cycloalkyl, $C_1$-$C_7$ heteroalkyl, and heterocycle, or R$^{7a}$ and R$^{7b}$ together with the nitrogen atom to which they attach form a heterocycle; R$^{8a}$, R$^{8b}$, R$^{8c}$, R$^{8d}$, R$^{8e}$ and R$^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; R$^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and R$^4$ is —CONH$_2$.

In certain embodiments, R$^1$ is aryl or heteroaryl, substituted with 0-3 substituents independently selected from fluoro, chloro, cyano, $C_1$-$C_6$ alkyl, $C_1$-$C_6$ fluoroalkyl, $C_1$-$C_6$ alkoxyalkyl, cyclopropyl, fluorocyclopropyl, OR$^5$, and NR$^{6a}$R$^{6b}$; wherein R$^5$ is hydrogen, $C_1$-$C_6$ alkyl or $C_1$-$C_6$ fluoroalkyl; and R$^{6a}$ and R$^{6b}$ are each independently hydrogen, $C_1$-$C_6$ alkyl, cyclopropyl, cyclobutyl, or $C_1$-$C_6$ heteroalkyl; or R$^{6a}$ and R$^{6b}$ together with the nitrogen atom to which they are attach form a heterocycle; wherein each R$^{6a}$ and R$^{6b}$ are substituted with 0-3 fluorine atoms; R$^{2a}$, R$^{2b}$, and R$^{2c}$ are each independently hydrogen, fluoro, or chloro; R$^3$ is —X—(CR$^{8a}$R$^{8b}$)$_p$—Z—(CR$^{8c}$R$^{8d}$)$_q$—N(R$^{7a}$)(R$^{7b}$), —X—(CR$^{8a}$R$^{8b}$)$_p$—Z—(CR$^{8c}$R$^{8d}$)$_q$—Y-A, -A'—X—(CR$^{8a}$R$^{8b}$)$_p$—N(R$^{7a}$)(R$^{7b}$), or -A'—X—(CR$^{8a}$R$^{8b}$)$_p$—Y-A; p is 0-2; q is 0-2; X, Y, and Z are each independently selected from a bond, CR$^{8e}$R$^{8f}$, O, S, NR$^{10}$, —C(O)—, —O—C(O)—, —C(O)—O—, —O—C(O)—NR$^{10}$—, —C(O)—NR$^{10}$—, —NR$^{10}$—C(O)—, —NR$^{10}$—C(O)—O—, —NR$^{10}$—C(O)—NR$^{10}$—, —NR$^{10}$—SO$_2$—, and —SO$_2$—; R$^{7a}$ and R$^{7b}$ are each independently selected from $C_1$-$C_7$ alkyl, $C_1$-$C_7$ haloalkyl, cycloalkyl, $C_1$-$C_7$ heteroalkyl, and heterocycle, or R$^{7a}$ and R$^{7b}$ together with the nitrogen atom to which they attach form a heterocycle; R$^{8a}$, R$^{8b}$, R$^{8c}$, R$^{8d}$, R$^{8e}$ and R$^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; R$^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and R$^4$ is —CONH$_2$.

In certain embodiments, R$^1$ is aryl substituted with 0-2 substituents independently selected from fluoro, chloro, $C_1$-$C_3$ alkyl, $C_1$-$C_3$ fluoroalkyl, $C_1$-$C_3$ alkoxyalkyl, and OR$^5$; wherein R$^5$ is hydrogen, $C_1$-$C_3$ alkyl, or $C_1$-$C_3$ fluoroalkyl; R$^{2a}$, R$^{2b}$, and R$^{2c}$ are each independently hydrogen, fluoro, or chloro; R$^3$ is —X—(CR$^{8a}$R$^{8b}$)$_p$—Z—(CR$^{8c}$R$^{8d}$)$_q$—N(R$^{7a}$)(R$^{7b}$), —X—(CR$^{8a}$R$^{8b}$)$_p$—Z—(CR$^{8c}$R$^{8d}$)$_q$—Y-A, -A'—X—(CR$^{8a}$R$^{8b}$)$_p$—N(R$^{7a}$)(R$^{7b}$), or -A'—X—(CR$^{8a}$R$^{8b}$)$_p$—Y-A; p is 0-2; q is 0-2; X, Y, and Z are each independently selected from a bond, CR$^{8e}$R$^{8f}$, O, S, NR$^{10}$, —C(O)—, —O—C(O)—, —C(O)—O—, —O—C(O)—NR$^{10}$—, —C(O)—NR$^{10}$—, —NR$^{10}$—C(O)—, —NR$^{10}$—C(O)—O—, —NR$^{10}$—C(O)—NR$^{10}$—, —NR$^{10}$—SO$_2$—, and —SO$_2$—; R$^{7a}$ and R$^{7b}$ are each independently selected from $C_1$-$C_7$ alkyl, $C_1$-$C_7$ haloalkyl, cycloalkyl, $C_1$-$C_7$ heteroalkyl, and heterocycle, or R$^{7a}$ and R$^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is heteroaryl substituted with 0-2 substituents independently selected from fluoro, chloro, $C_1$-$C_3$ alkyl, $C_1$-$C_3$ fluoroalkyl, and $C_1$-$C_3$ alkoxyalkyl; $R^{2a}$, $R^{2b}$, and $R^{2c}$ are each independently hydrogen, fluoro, or chloro; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; p is 0-2; q is 0-2; X, Y, and Z are each independently selected from a bond, $CR^{8e}R^{8f}$, O, S, $NR^{10}$, —C(O)—, —O—C(O)—, —C(O)—O—, —O—C(O)—$NR^{10}$—, —C(O)—$NR^{10}$—, —$NR^{10}$—C(O)—, —$NR^{10}$—C(O)—O—, —$NR^{10}$—C(O)—$NR^{10}$—, —$NR^{10}$—$SO_2$—, and —$SO_2$—; $R^{7a}$ and $R^{7b}$ are each independently selected from $C_1$-$C_7$ alkyl, $C_1$-$C_7$ haloalkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$ or cyano.

In certain embodiments, $R^1$ is aryl, heteroaryl, heterocycle, or cycloalkyl; $R^{2a}$, $R^{2b}$, and $R^{2c}$ are each hydrogen; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; p is 0-2; q is 0-2; X, Y, and Z are each independently selected from a bond, $CR^{8e}R^{8f}$, O, S, $NR^{10}$, —C(O)—, —O—C(O)—, —C(O)—O—, —O—C(O)—$NR^{10}$—, —C(O)—$NR^{10}$—, —$NR^{10}$—C(O)—, —$NR^{10}$—C(O)—O—, —$NR^{10}$—C(O)—NR—, —$NR^{10}$—$SO_2$—, and —$SO_2$—; $R^{7a}$ and $R^{7b}$ are each independently selected from $C_1$-$C_7$ alkyl, $C_1$-$C_7$ haloalkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl or heteroaryl; $R^{2a}$, $R^{2b}$, and $R^{2c}$ are each hydrogen; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; p is 0-2; q is 0-2; X, Y, and Z are each independently selected from a bond, $CR^{8e}R^{8f}$, O, S, $NR^{10}$, —C(O)—, —O—C(O)—, —C(O)—O—, —O—C(O)—$NR^{10}$—, —C(O)—$NR^{10}$—, —$NR^{10}$—C(O)—, —$NR^{10}$—C(O)—O—, —$NR^{10}$—C(O)—NR—, —$NR^{10}$—$SO_2$—, and —$SO_2$—; $R^{7a}$ and $R^{7b}$ are each independently selected from $C_1$-$C_7$ alkyl, $C_1$-$C_7$ haloalkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl or heteroaryl, substituted with 0-3 substituents independently selected from fluoro, chloro, cyano, $C_1$-$C_6$ alkyl, $C_1$-$C_6$ fluoroalkyl, $C_1$-$C_6$ alkoxyalkyl, cyclopropyl, fluorocyclopropyl, $OR^5$, and $NR^{6a}R^{6b}$; wherein $R^5$ is hydrogen, $C_1$-$C_6$ alkyl or $C_1$-$C_6$ fluoroalkyl; and $R^{6a}$ and $R^{6b}$ are each independently hydrogen, $C_1$-$C_6$ alkyl, cyclopropyl, cyclobutyl, or $C_1$-$C_6$ heteroalkyl; or $R^{6a}$ and $R^{6b}$ together with the nitrogen atom to which they are attach form a heterocycle; wherein each $R^{6a}$ and $R^{6b}$ are substituted with 0-3 fluorine atoms; $R^{2a}$, $R^{2b}$, and $R^{2c}$ are each hydrogen; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; p is 0-2; q is 0-2; X, Y, and Z are each independently selected from a bond, $CR^{8e}R^{8f}$, O, S, $NR^{10}$, —C(O)—, —O—C(O)—, —C(O)—O—, —O—C(O)—$NR^{10}$—, —C(O)—$NR^{10}$—, —$NR^{10}$—C(O)—, —$NR^{10}$—C(O)—O—, —$NR^{10}$—C(O)—$NR^{10}$—, —$NR^{10}$—$SO_2$—, and —$SO_2$—; $R^{7a}$ and $R^{7b}$ are each independently selected from $C_1$-$C_7$ alkyl, $C_1$-$C_7$ haloalkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl substituted with 0-2 substituents independently selected from fluoro, chloro, $C_1$-$C_3$ alkyl, $C_1$-$C_3$ fluoroalkyl, $C_1$-$C_3$ alkoxyalkyl, and $OR^5$; wherein $R^5$ is hydrogen, $C_1$-$C_3$ alkyl, or $C_1$-$C_3$ fluoroalkyl; $R^{2a}$, $R^{2b}$, and $R^{2c}$ are each hydrogen; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; p is 0-2; q is 0-2; X, Y, and Z are each independently selected from a bond, $CR^{8e}R^{8f}$, O, S, $NR^{10}$, —C(O)—, —O—C(O)—, —C(O)—O—, —O—C(O)—$NR^{10}$—, —C(O)—$NR^{10}$—, —$NR^{10}$—C(O)—, —$NR^{10}$—C(O)—O—, —$NR^{10}$—C(O)—NR—, —$NR^{10}$—$SO_2$—, and —$SO_2$—; $R^{7a}$ and $R^{7b}$ are each independently selected from $C_1$-$C_7$ alkyl, $C_1$-$C_7$ haloalkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is heteroaryl substituted with 0-2 substituents independently selected from fluoro, chloro, $C_1$-$C_3$ alkyl, $C_1$-$C_3$ fluoroalkyl, and $C_1$-$C_3$ alkoxyalkyl; $R^{2a}$, $R^{2b}$, and $R^{2c}$ are each hydrogen; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; p is 0-2; q is 0-2; X, Y, and Z are each independently selected from a bond, $CR^{8e}R^{8f}$, O, S, $NR^{10}$, —C(O)—, —O—C(O)—, —C(O)—O—, —O—C(O)—$NR^{10}$—, —C(O)—$NR^{10}$—, —$NR^{10}$—C(O)—, —$NR^{10}$—C(O)—O—, —$NR^{10}$—C(O)—NR—, —$NR^{10}$—

$SO_2$—, and —$SO_2$—; $R^{7a}$ and $R^{7b}$ are each independently selected from $C_1$-$C_7$ alkyl, $C_1$-$C_7$ haloalkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl, heteroaryl, heterocycle, or cycloalkyl; $R^{2a}$, $R^{2b}$, and $R^{2c}$ are each independently hydrogen, fluoro, or chloro; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl or heteroaryl; $R^{2a}$, $R^{2b}$, and $R^{2c}$ are each independently hydrogen, fluoro, or chloro; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl or heteroaryl, substituted with 0-3 substituents independently selected from fluoro, chloro, cyano, $C_1$-$C_6$ alkyl, $C_1$-$C_6$ fluoroalkyl, $C_1$-$C_6$ alkoxyalkyl, cyclopropyl, fluorocyclopropyl, $OR^5$, and $NR^{6a}R^{6b}$; wherein $R^5$ is hydrogen, $C_1$-$C_6$ alkyl or $C_1$-$C_6$ fluoroalkyl; and $R^{6a}$ and $R^{6b}$ are each independently hydrogen, $C_1$-$C_6$ alkyl, cyclopropyl, cyclobutyl, or $C_1$-$C_6$ heteroalkyl; or $R^{6a}$ and $R^{6b}$ together with the nitrogen atom to which they are attach form a heterocycle; wherein each $R^{6a}$ and $R^{6b}$ are substituted with 0-3 fluorine atoms; $R^{2a}$, $R^{2b}$, and $R^{2c}$ are each independently hydrogen, fluoro, or chloro; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl substituted with 0-2 substituents independently selected from fluoro, chloro, $C_1$-$C_3$ alkyl, $C_1$-$C_3$ fluoroalkyl, $C_1$-$C_3$ alkoxyalkyl, and $OR^5$; wherein $R^5$ is hydrogen, $C_1$-$C_3$ alkyl, or $C_1$-$C_3$ fluoroalkyl; $R^{2a}$, $R^{2b}$, and $R^{2c}$ are each independently hydrogen, fluoro, or chloro; $R^{2a}$, $R^{2b}$, and $R^{2c}$ are each independently hydrogen, fluoro, or chloro; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is heteroaryl substituted with 0-2 substituents independently selected from fluoro, chloro, $C_1$-$C_3$ alkyl, $C_1$-$C_3$ fluoroalkyl, and $C_1$-$C_3$ alkoxyalkyl; $R^{2a}$, $R^{2b}$, and $R^{2c}$ are each independently hydrogen, fluoro, or chloro; $R^3$ is —X—$(CR^{8a}R^{8b})_p$—Z—$(CR^{8c}R_{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$ O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl, heteroaryl, heterocycle, or cycloalkyl; $R^{2a}$, $R^{2b}$, and $R^{2c}$ are each hydrogen; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl or heteroaryl; $R^{2a}$, $R^{2b}$, and $R^{2c}$ are each hydrogen; $R^3$ is —X—$(CR^{8a}R^{8b})_p$—Z—$(CR^{8c}R^{8d})_q$—$N(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—$N(R^{7a})(R^{7b})$, or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$;

$R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl or heteroaryl, substituted with 0-3 substituents independently selected from fluoro, chloro, cyano, $C_1$-$C_6$ alkyl, $C_1$-$C_6$ fluoroalkyl, $C_1$-$C_6$ alkoxyalkyl, cyclopropyl, fluorocyclopropyl, $OR^5$, and $NR^{6a}R^{6b}$; wherein $R^5$ is hydrogen, $C_1$-$C_6$ alkyl or $C_1$-$C_6$ fluoroalkyl; and $R^{6a}$ and $R^{6b}$ are each independently hydrogen, $C_1$-$C_6$ alkyl, cyclopropyl, cyclobutyl, or $C_1$-$C_6$ heteroalkyl; or $R^{6a}$ and $R^{6b}$ together with the nitrogen atom to which they are attach form a heterocycle; wherein each $R^{6a}$ and $R^{6b}$ are substituted with 0-3 fluorine atoms; $R^{2a}$, $R^{2b}$, and $R^{2c}$ are each hydrogen; $R^3$ is —X—$(CR^{8a}R^{8b})_p$—Z—$(CR^{8c}R^{8d})_q$—N$(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—N$(R^{7a})(R^{7b})$, or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl substituted with 0-2 substituents independently selected from fluoro, chloro, $C_1$-$C_3$ alkyl, $C_1$-$C_3$ fluoroalkyl, $C_1$-$C_3$ alkoxyalkyl, and $OR^5$; wherein $R^5$ is hydrogen, $C_1$-$C_3$ alkyl, or $C_1$-$C_3$ fluoroalkyl; $R^{2a}$, $R^{2b}$, and $R^{2c}$ are each hydrogen; $R^3$ is —X—$(CR^{8a}R^{8b})_p$—Z—$(CR^{8c}R^{8d})_q$—N$(R^{7a})(R^{7b})$, —X—$(CR^{8c}R^{8d})_q$—Y-A, -A'—X—$(CR^{8a}R^{8b})_p$—N$(R^{7a})(R^{7b})$, or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is heteroaryl substituted with 0-2 substituents independently selected from fluoro, chloro, $C_1$-$C_3$ alkyl, $C_1$-$C_3$ fluoroalkyl, and $C_1$-$C_3$ alkoxyalkyl; $R^{2a}$, $R^{2b}$, and $R^{2c}$ are each hydrogen; $R^3$ is —X—$(CR^{8a}R^{8b})_p$—Z—$(CR^{8c}R^{8d})_q$—N$(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—N$(R^{7a})(R^{7b})$, or -A'—X—$(CR^{8a}R^{8b})_p$—Y- A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl, heteroaryl, heterocycle, or cycloalkyl; $R^{2a}$, $R^{2b}$, and $R^{2c}$ are each independently hydrogen, fluoro, or chloro; $R^3$ is —X—$(CR^{8a}R^{8b})_p$—Z—$(CR^{8c}R^{8d})_q$—N$(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—N$(R^{7a})(R^{7b})$, or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is cycloalkyl or heterocycle; and $R^4$ is —$CONH_2$.

In certain embodiments, $R^1$ is aryl or heteroaryl; $R^{2a}$, $R^{2b}$, and $R^{2c}$ are each independently hydrogen, fluoro, or chloro; $R^3$ is —X—$(CR^{8a}R^{8b})_p$—Z—$(CR^{8c}R^{8d})_q$—N$(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—N$(R^{7a})(R^{7b})$, or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is cycloalkyl or heterocycle; and $R^4$ is —$CONH_2$.

In certain embodiments, $R^1$ is aryl or heteroaryl, substituted with 0-3 substituents independently selected from fluoro, chloro, cyano, $C_1$-$C_6$ alkyl, $C_1$-$C_6$ fluoroalkyl, $C_1$-$C_6$ alkoxyalkyl, cyclopropyl, fluorocyclopropyl, $OR^5$, and $NR^{6a}R^{6b}$; wherein $R^5$ is hydrogen, $C_1$-$C_6$ alkyl or $C_1$-$C_6$ fluoroalkyl; and $R^{6a}$ and $R^{6b}$ are each independently hydrogen, $C_1$-$C_6$ alkyl, cyclopropyl, cyclobutyl, or $C_1$-$C_6$ heteroalkyl; or $R^{6a}$ and $R^{6b}$ together with the nitrogen atom to which they are attach form a heterocycle; wherein each $R^{6a}$ and $R^{6b}$ are substituted with 0-3 fluorine atoms; $R^{2a}$, $R^{2b}$, and $R^{2c}$ are each independently hydrogen, fluoro, or chloro; $R^3$ is —X—$(CR^{8a}R^{8b})_p$—Z—$(CR^{8c}R^{8d})_q$—N$(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—N$(R^{7a})(R^{7b})$, or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$ 0, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is cycloalkyl or heterocycle; and $R^4$ is —$CONH_2$.

In certain embodiments, $R^1$ is aryl substituted with 0-2 substituents independently selected from fluoro, chloro, $C_1$-$C_3$ alkyl, $C_1$-$C_3$ fluoroalkyl, $C_1$-$C_3$ alkoxyalkyl, and $OR^5$; wherein $R^5$ is hydrogen, $C_1$-$C_3$ alkyl, or $C_1$-$C_3$ fluoroalkyl; $R^{2a}$, $R^{2b}$, and $R^{2c}$ are each independently hydrogen, fluoro, or chloro; $R^{2a}$, $R^{2b}$, and $R^{2c}$ are each independently hydrogen, fluoro, or chloro; $R^3$ is —X—$(CR^{8a}R^{8b})_p$—Z—$(CR^{8c}R^{8d})_q$—N($R^{7a}$)($R^{7b}$), —X—$(CR^{8a}R^{8b})_p$—Z—$(CR^{8c}R^{8d})_q$—Y-A, -A'—X—$(CR^{8a}R^{8b})_p$—N($R^{7a}$)($R^{7b}$), or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is cycloalkyl or heterocycle; and $R^4$ is —$CONH_2$.

In certain embodiments, $R^1$ is heteroaryl substituted with 0-2 substituents independently selected from fluoro, chloro, $C_1$-$C_3$ alkyl, $C_1$-$C_3$ fluoroalkyl, and $C_1$-$C_3$ alkoxyalkyl; $R^{2a}$, $R^{2b}$, and $R^{2c}$ are each independently hydrogen, fluoro, or chloro; $R^3$ is —X—$(CR^{8a}R^{8b})_p$—Z—$(CR^{8c}R^{8d})_q$—N($R^{7a}$)($R^{7b}$), —X—$(CR^{8a}R^{8b})_p$—Z—$(CR^{8c}R^{8d})_q$—Y-A, -A'—X—$(CR^{8a}R^{8b})_p$—N($R^{7a}$)($R^{7b}$), or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$ O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is cycloalkyl or heterocycle; and $R^4$ is —$CONH_2$.

In certain embodiments, $R^1$ is aryl, heteroaryl, heterocycle, or cycloalkyl; $R^{2a}$, $R^{2b}$, and $R^{2c}$ are each hydrogen; $R^3$ is —X—$(CR^{8a}R^{8b})_p$—Z—$(CR^{8c}R^{8d})_q$—N($R^{7a}$)($R^{7b}$), —X—$(CR^{8a}R^{8b})_p$—Z—$(CR^{8c}R^{8d})_q$—Y-A, -A'—X—$(CR^{8a}R^{8b})_p$—N($R^{7a}$)($R^{7b}$), or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is aryl, heteroaryl, cycloalkyl, or heterocycle; and $R^4$ is —$CONH_2$.

In certain embodiments, $R^1$ is aryl or heteroaryl; $R^{2a}$, $R^{2b}$, and $R^{2c}$ are each hydrogen; $R^3$ is —X—$(CR^{8a}R^{8b})_p$—Z—$(CR^{8c}R^{8d})_q$—N($R^{7a}$)($R^{7b}$), —X—$(CR^{8a}R^{8b})_p$—Z—$(CR^{8c}R^{8d})_q$—Y-A, -A'—X—$(CR^{8a}R^{8b})_p$—N($R^{7a}$)($R^{7b}$), or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is cycloalkyl or heterocycle; and $R^4$ is —$CONH_2$.

In certain embodiments, $R^1$ is aryl or heteroaryl, substituted with 0-3 substituents independently selected from fluoro, chloro, cyano, $C_1$-$C_6$ alkyl, $C_1$-$C_6$ fluoroalkyl, $C_1$-$C_6$ alkoxyalkyl, cyclopropyl, fluorocyclopropyl, $OR^5$, and $NR^{6a}R^{6b}$; wherein $R^5$ is hydrogen, $C_1$-$C_6$ alkyl or $C_1$-$C_6$ fluoroalkyl; and $R^{6a}$ and $R^{6b}$ are each independently hydrogen, $C_1$-$C_6$ alkyl, cyclopropyl, cyclobutyl, or $C_1$-$C_6$ heteroalkyl; or $R^{6a}$ and $R^{6b}$ together with the nitrogen atom to which they are attach form a heterocycle; wherein each $R^{6a}$ and $R^{6b}$ are substituted with 0-3 fluorine atoms; $R^{2a}$, $R^{2b}$, and $R^{2c}$ are each hydrogen; $R^3$ is —X—$(CR^{8a}R^{8b})_p$—Z—$(CR^{8c}R^{8d})_q$—N($R^{7a}$)($R^{7b}$), —X—$(CR^{8a}R^{8b})_p$—Z—$(CR^{8c}R^{8d})_q$—Y-A, -A'—X—$(CR^{8a}R^{8b})_p$—N($R^{7a}$)($R^{7b}$), or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is cycloalkyl or heterocycle; and $R^4$ is —$CONH_2$.

In certain embodiments, $R^1$ is aryl substituted with 0-2 substituents independently selected from fluoro, chloro, $C_1$-$C_3$ alkyl, $C_1$-$C_3$ fluoroalkyl, $C_1$-$C_3$ alkoxyalkyl, and $OR^5$; wherein $R^5$ is hydrogen, $C_1$-$C_3$ alkyl, or $C_1$-$C_3$ fluoroalkyl; $R^{2a}$, $R^{2b}$, and $R^{2c}$ are each hydrogen; $R^3$ is —X—$(CR^{8a}R^{8b})_p$—Z—$(CR^{8c}R^{8d})_q$—N($R^{7a}$)($R^{7b}$), —X—$(CR^{8a}R^{8b})_p$—Z—$(CR^{8c}R^{8d})_q$—Y-A, -A'—X—$(CR^{8a}R^{8b})_p$—N($R^{7a}$)($R^{7b}$), or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is cycloalkyl or heterocycle; and $R^4$ is —$CONH_2$.

In certain embodiments, $R^1$ is heteroaryl substituted with 0-2 substituents independently selected from fluoro, chloro, $C_1$-$C_3$ alkyl, $C_1$-$C_3$ fluoroalkyl, and $C_1$-$C_3$ alkoxyalkyl; $R^{2a}$, $R^{2b}$, and $R^{2c}$ are each hydrogen; $R^3$ is —X—$(CR^{8a}R^{8b})_p$—Z—$(CR^{8c}R^{8d})_q$—N($R^{8a}$)($R^{8b}$), —X—$(CR^{8a}R^{8b})_p$—Z—$(CR^{8c}R^{8d})_q$—Y-A, -A'—X—$(CR^{8a}R^{8b})_p$—N($R^{7a}$)($R^{7b}$), or -A'—X—$(CR^{8a}R^{8b})_p$—Y-A; wherein p is 0-2; q is 0-2; X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy; $R^{10}$ at each occurrence is independently selected from hydrogen, $C_1$-$C_4$ alkyl, and $C_1$-$C_4$ haloalkyl; A is aryl, heteroaryl, cycloalkyl, or heterocycle; A' is cycloalkyl or heterocycle; and $R^4$ is —$CONH_2$.

In certain embodiments, $R^1$ is aryl, heteroaryl, heterocycle, or cycloalkyl; $R^{2a}$, $R^{2b}$, and $R^{2c}$ are each independently hydrogen, fluoro, or chloro; $R^3$ is

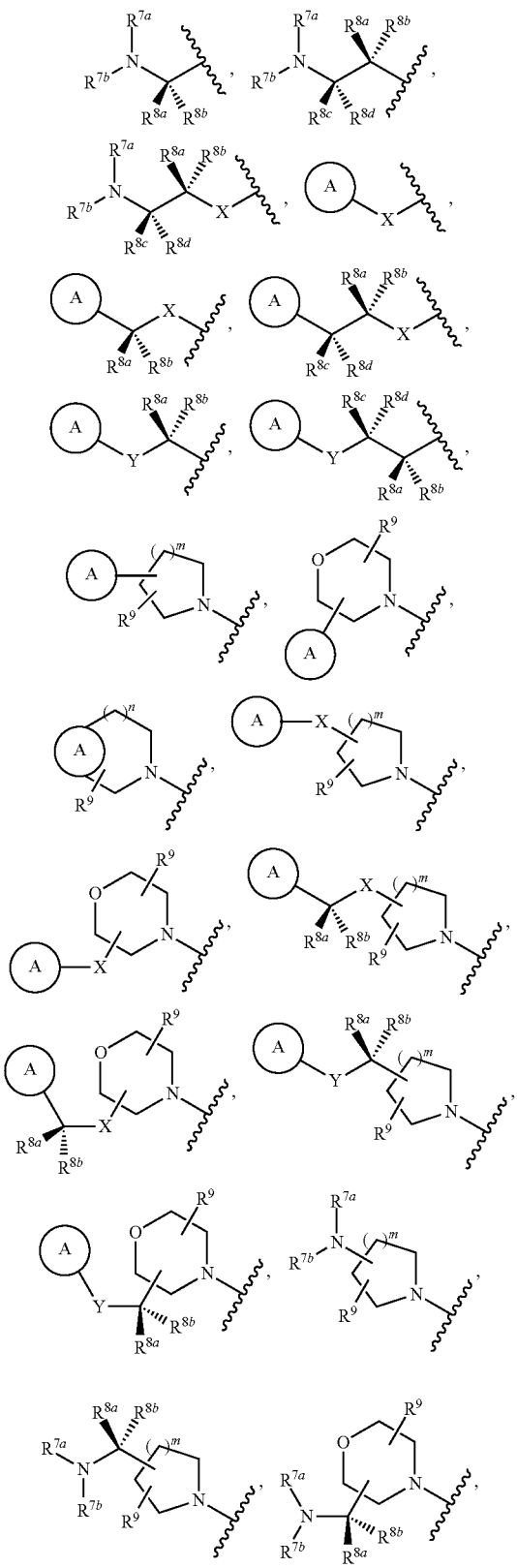

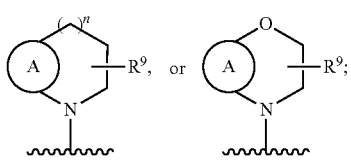

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; n is 0-2; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^1$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl or heteroaryl; $R^{2a}$, $R^{2b}$, and $R^{2c}$ are each independently hydrogen, fluoro, or chloro; $R^3$ is

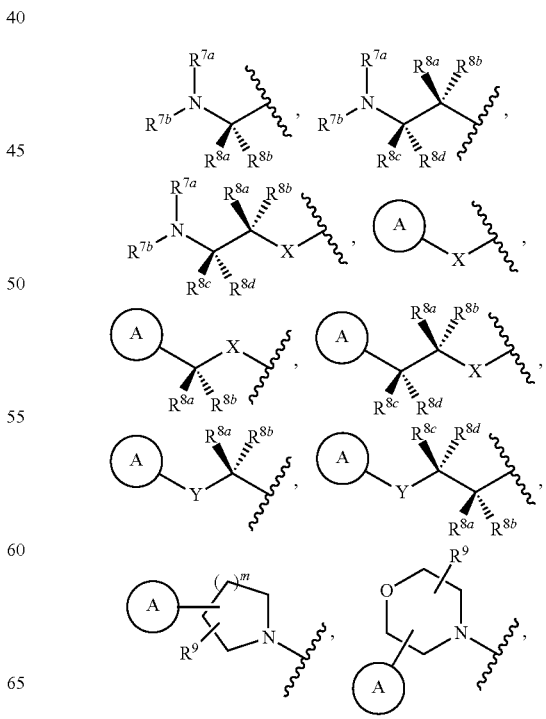

-continued

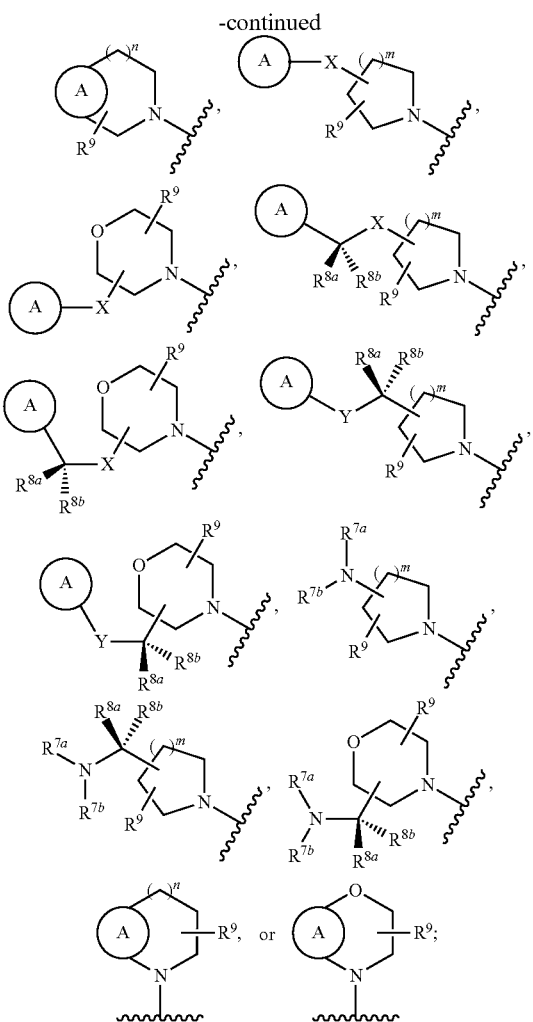

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; n is 0-2; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^1$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl or heteroaryl, substituted with 0-3 substituents independently selected from fluoro, chloro, cyano, $C_1$-$C_6$ alkyl, $C_1$-$C_6$ fluoroalkyl, $C_1$-$C_6$ alkoxyalkyl, cyclopropyl, fluorocyclopropyl, $OR^5$, and $NR^{6a}R^{6b}$; wherein $R^5$ is hydrogen, $C_1$-$C_6$ alkyl or $C_1$-$C_6$ fluoroalkyl; and $R^{6a}$ and $R^{6b}$ are each independently hydrogen, $C_1$-$C_6$ alkyl, cyclopropyl, cyclobutyl, or $C_1$-$C_6$ heteroalkyl; or $R^{6a}$ and $R^{6b}$ together with the nitrogen atom to which they are attach form a heterocycle; wherein each $R^{6a}$ and $R^{6b}$ are substituted with 0-3 fluorine atoms; $R^{2a}$, $R^{2b}$, and $R^{2c}$ are each independently hydrogen, fluoro, or chloro; $R^3$ is

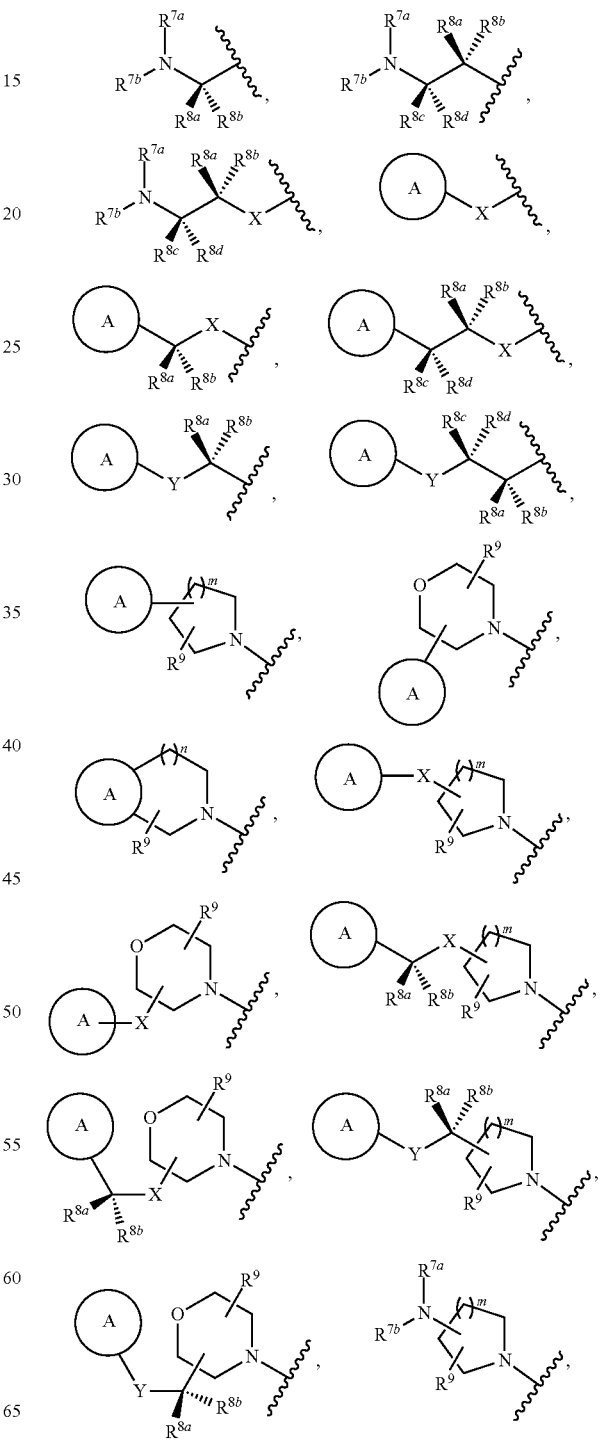

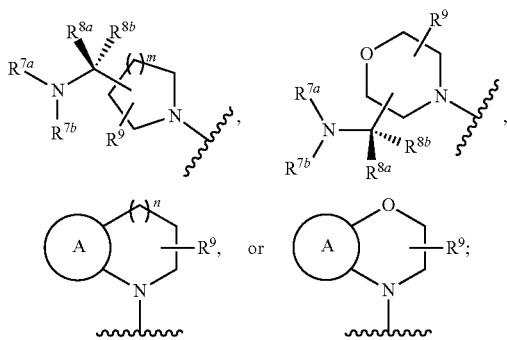

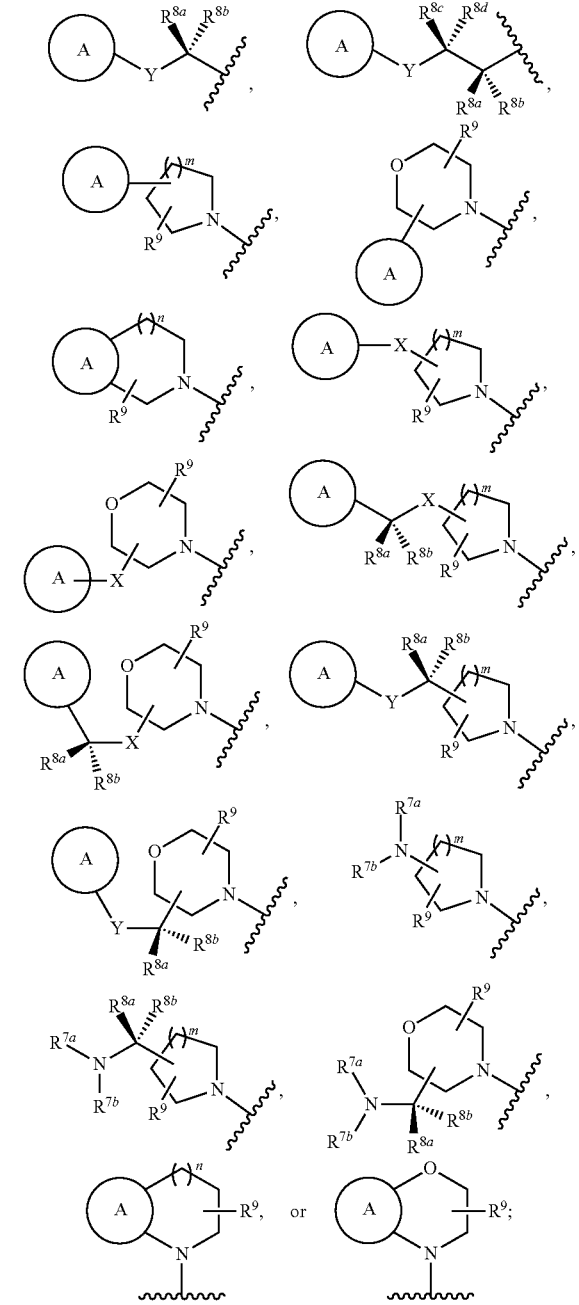

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; n is 0-2; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{2b}$ $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl substituted with 0-2 substituents independently selected from fluoro, chloro, $C_1$-$C_3$ alkyl, $C_1$-$C_3$ fluoroalkyl, $C_1$-$C_3$ alkoxyalkyl, and $OR^5$; wherein $R^5$ is hydrogen, $C_1$-$C_3$ alkyl, or $C_1$-$C_3$ fluoroalkyl; $R^{2a}$, $R^{2b}$, and $R^{2c}$ are each independently hydrogen, fluoro, or chloro; $R^{2a}$, $R^{2b}$, and $R^{2c}$ are each independently hydrogen, fluoro, or chloro; $R^3$ is

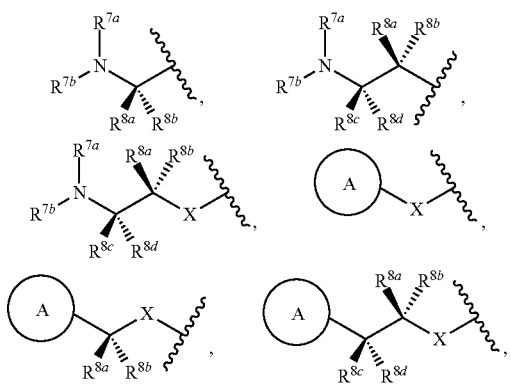

wherein X is a bond, $CR^{8e}R^{8f}$, O, or $NR^{10}$; Y is a bond $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ ands $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; n is 0-2; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$ $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is heteroaryl substituted with 0-2 substituents independently selected from fluoro, chloro, $C_1$-$C_3$ alkyl, $C_1$-$C_3$ fluoroalkyl, and $C_1$-$C_3$ alkoxyalkyl; $R^{2a}$, $R^{2b}$, and $R^{2c}$ are each independently hydrogen, fluoro, or chloro; $R^3$ is

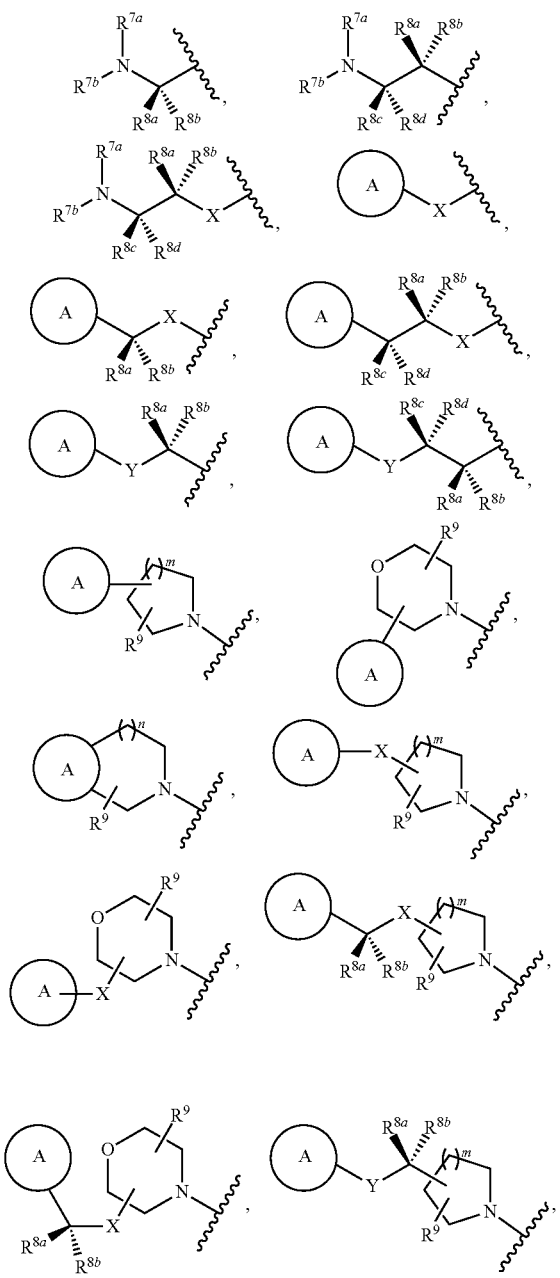

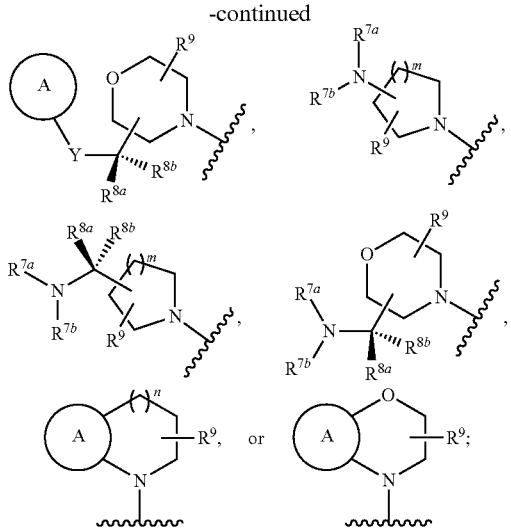

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0 -4 $R^9$ groups are present in each $R^3$; m is 0-3; n is 0-2; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$ $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl, heteroaryl, heterocycle, or cycloalkyl; $R^{2a}$, $R^{2b}$, and $R^{2c}$ are each hydrogen; $R^3$ is

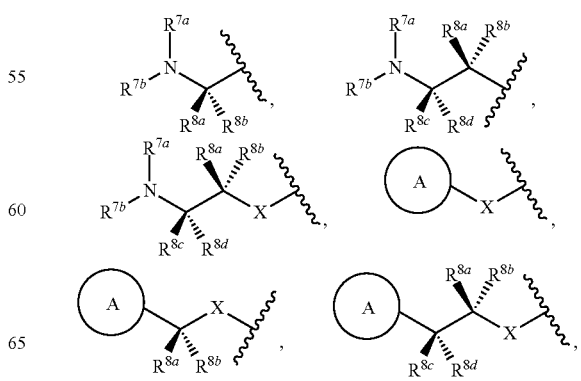

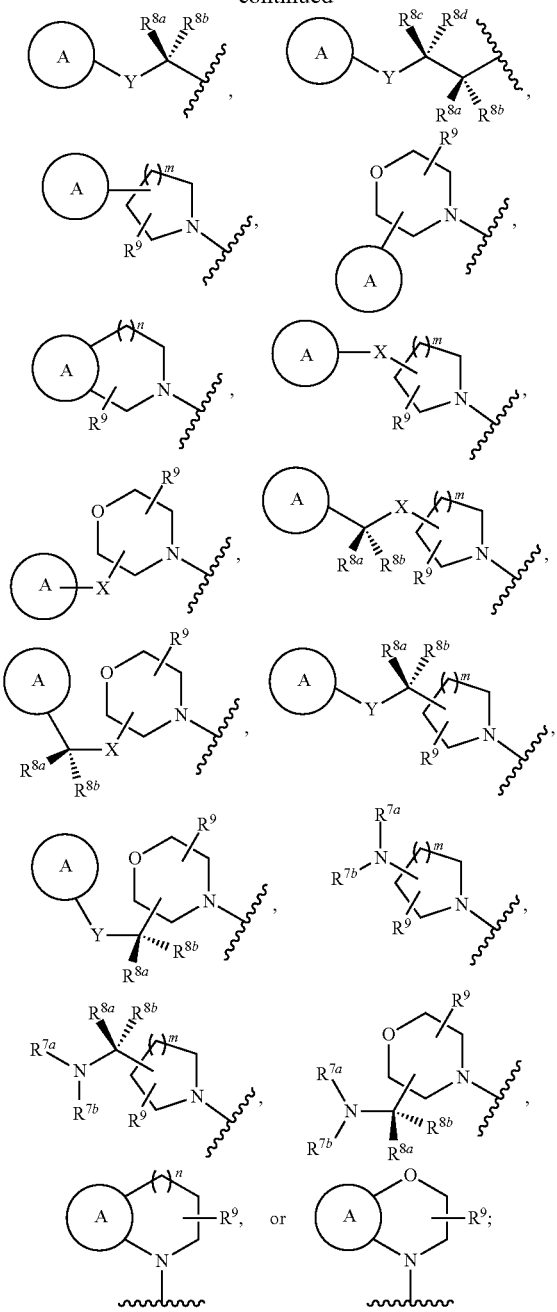

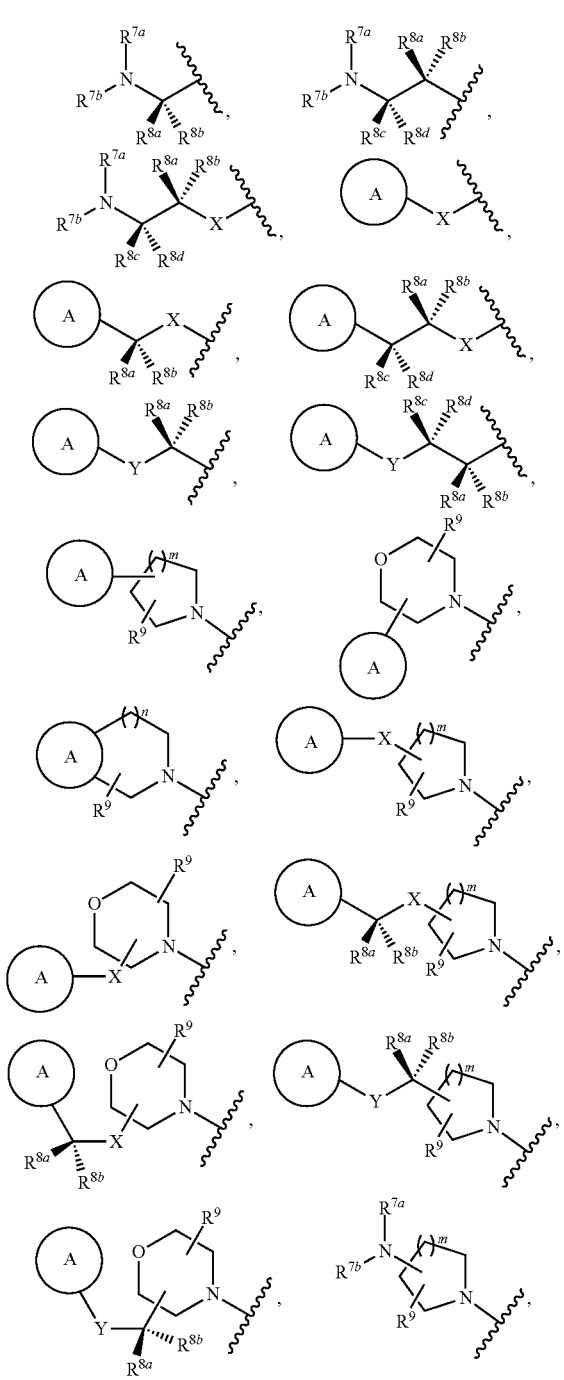

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; n is 0-2; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^1$, $NR^{12a}R^{12b}$ $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl or heteroaryl; $R^{2a}$, $R^{2b}$, and $R^{2c}$ are each hydrogen; $R^3$ is -continued

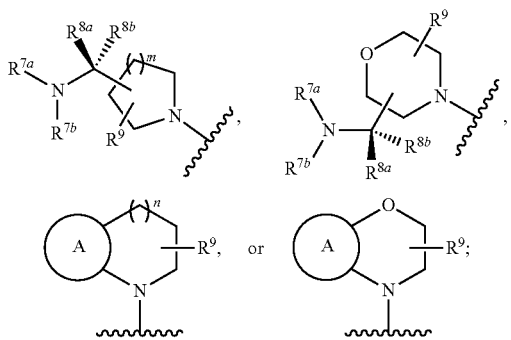

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; n is 0-2; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl or heteroaryl, substituted with 0-3 substituents independently selected from fluoro, chloro, cyano, $C_1$-$C_6$ alkyl, $C_1$-$C_6$ fluoroalkyl, $C_1$-$C_6$ alkoxyalkyl, cyclopropyl, fluorocyclopropyl, $OR^5$, and $NR^{6a}R^{6b}$; wherein $R^5$ is hydrogen, $C_1$-$C_6$ alkyl or $C_1$-$C_6$ fluoroalkyl; and $R^{6a}$ and $R^{6b}$ are each independently hydrogen, $C_1$-$C_6$ alkyl, cyclopropyl, cyclobutyl, or $C_1$-$C_6$ heteroalkyl; or $R^{6a}$ and $R^{6b}$ together with the nitrogen atom to which they are attach form a heterocycle; wherein each $R^{6a}$ and $R^{6b}$ are substituted with 0-3 fluorine atoms; $R^{2a}$, $R^{2b}$, and $R^{2c}$ are each hydrogen; $R^3$ is

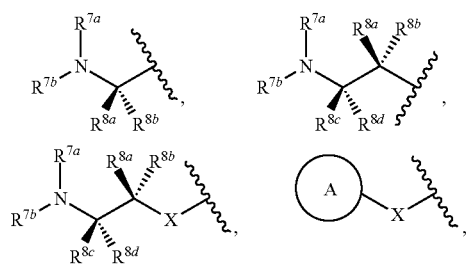

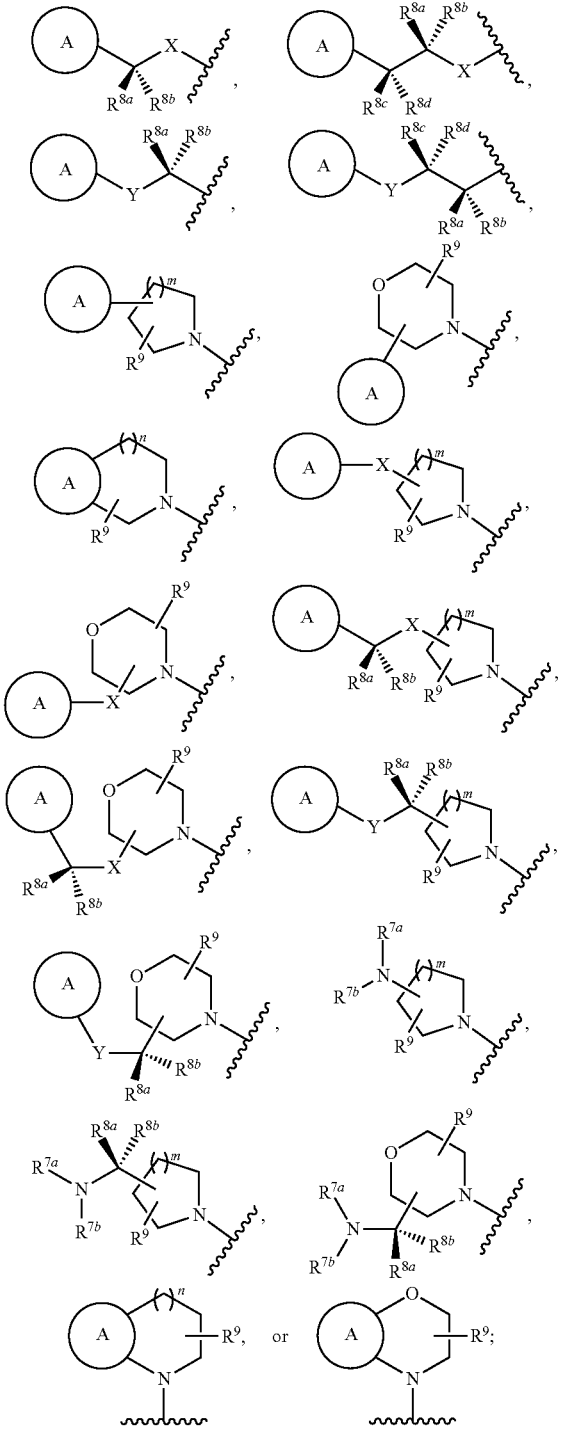

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; n is 0-2; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$ $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl substituted with 0-2 substituents independently selected from fluoro, chloro, $C_1$-$C_3$ alkyl, $C_1$-$C_3$ fluoroalkyl, $C_1$-$C_3$ alkoxyalkyl, and $OR^5$; wherein $R^5$ is hydrogen, $C_1$-$C_3$ alkyl, or $C_1$-$C_3$ fluoroalkyl; $R^{2a}$, $R^{2b}$, and $R^{2c}$ are each hydrogen; $R^3$ is

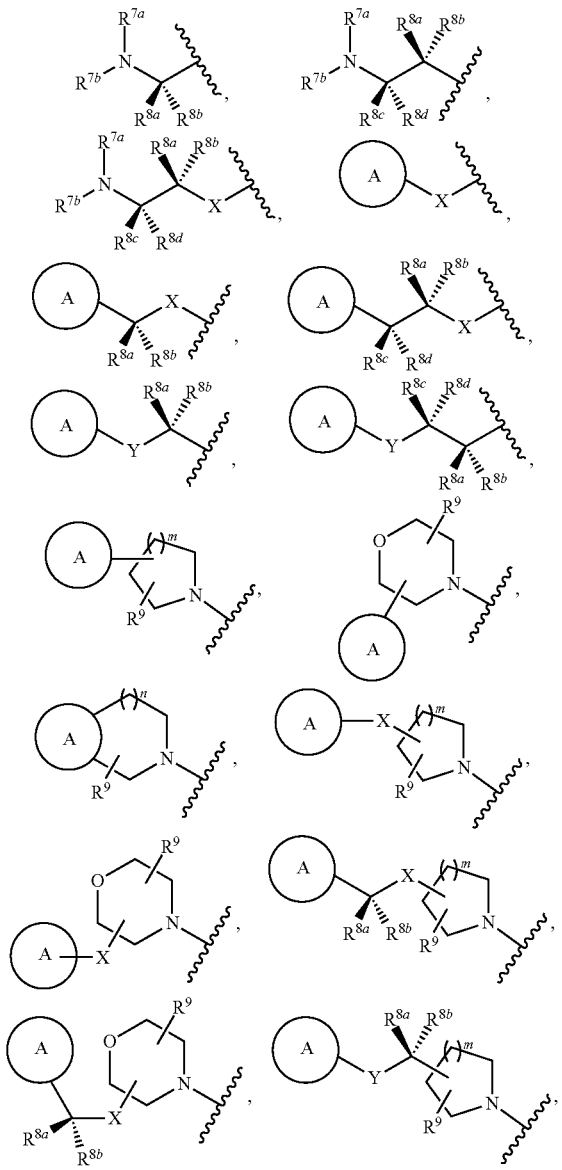

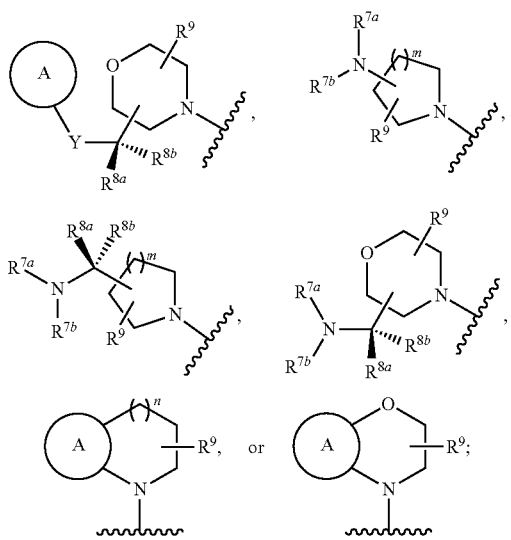

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; n is 0-2; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^1$, $NR^{12a}R^{12b}$ $SO_2R^{11}$, and $COR^1$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is heteroaryl substituted with 0-2 substituents independently selected from fluoro, chloro, $C_1$-$C_3$ alkyl, $C_1$-$C_3$ fluoroalkyl, and $C_1$-$C_3$ alkoxyalkyl; $R^{2a}$, $R^{2b}$, and $R^{2c}$ are each hydrogen; $R^3$ is

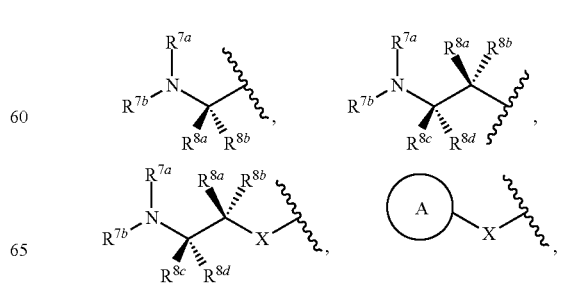

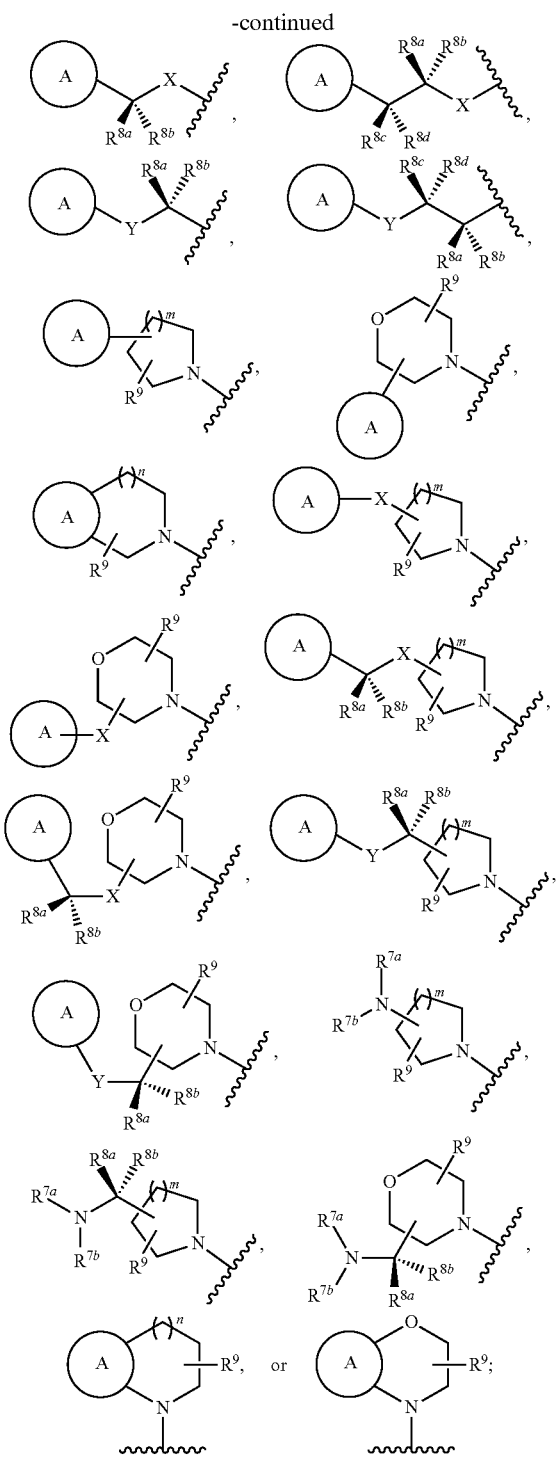

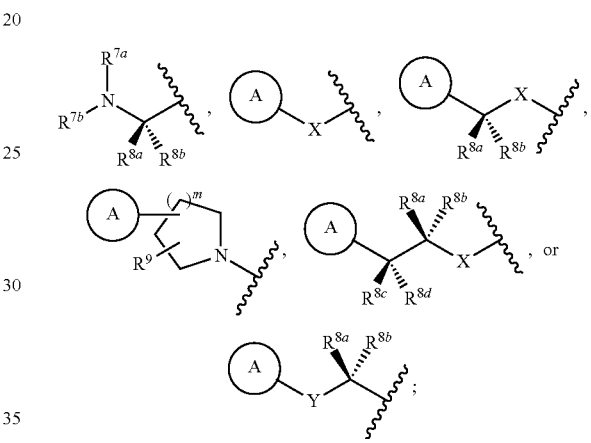

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; n is 0-2; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$ $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl, heteroaryl, heterocycle, or cycloalkyl; $R^{2a}$, $R^{2b}$, and $R^{2c}$ are each independently hydrogen, fluoro, or chloro; $R^3$ is wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl or heteroaryl; $R^{2a}$, $R^{2b}$, and $R^{2c}$ are each independently hydrogen, fluoro, or chloro; $R^3$ is

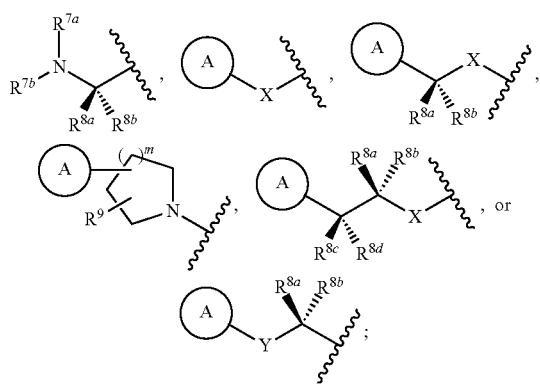

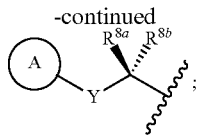

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl or heteroaryl, substituted with 0-3 substituents independently selected from fluoro, chloro, cyano, $C_1$-$C_6$ alkyl, $C_1$-$C_6$ fluoroalkyl, $C_1$-$C_6$ alkoxyalkyl, cyclopropyl, fluorocyclopropyl, $OR^5$, and $NR^{6a}R^{6b}$; wherein $R^5$ is hydrogen, $C_1$-$C_6$ alkyl or $C_1$-$C_6$ fluoroalkyl; and $R^{6a}$ and $R^{6b}$ are each independently hydrogen, $C_1$-$C_6$ alkyl, cyclopropyl, cyclobutyl, or $C_1$-$C_6$ heteroalkyl; or $R^{6a}$ and $R^{6b}$ together with the nitrogen atom to which they are attach form a heterocycle; wherein each $R^{6a}$ and $R^{6b}$ are substituted with 0-3 fluorine atoms; $R^{2a}$, $R^{2b}$, and $R^{2c}$ are each independently hydrogen, fluoro, or chloro; $R^3$ is

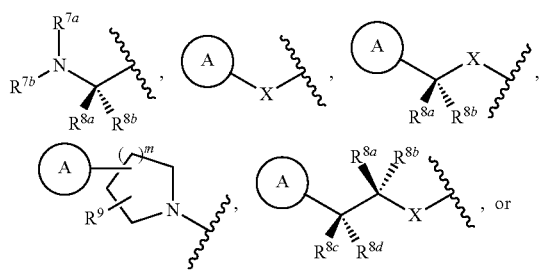

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl substituted with 0-2 substituents independently selected from fluoro, chloro, $C_1$-$C_3$ alkyl, $C_1$-$C_3$ fluoroalkyl, $C_1$-$C_3$ alkoxyalkyl, and $OR^5$; wherein $R^5$ is hydrogen, $C_1$-$C_3$ alkyl, or $C_1$-$C_3$ fluoroalkyl; $R^{2a}$, $R^{2b}$, and $R^{2c}$ are each independently hydrogen, fluoro, or chloro; $R^{2a}$, $R^{2b}$, and $R^{2c}$ are each independently hydrogen, fluoro, or chloro; $R^3$ is

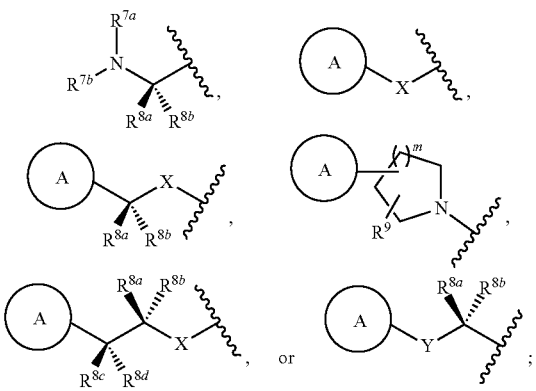

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is heteroaryl substituted with 0-2 substituents independently selected from fluoro, chloro, $C_1$-$C_3$ alkyl, $C_1$-$C_3$ fluoroalkyl, and $C_1$-$C_3$ alkoxyalkyl; $R^{2a}$, $R^{2b}$, and $R^{2c}$ are each independently hydrogen, fluoro, or chloro; $R^3$ is

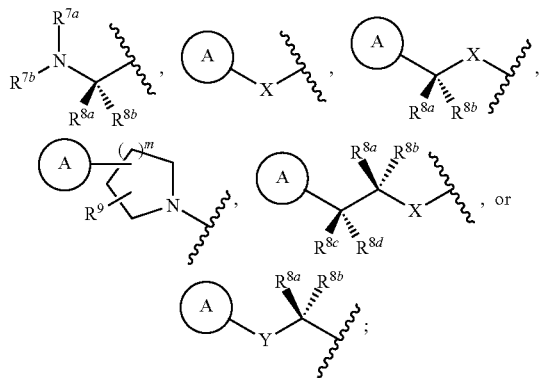

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^1$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl, heteroaryl, heterocycle, or cycloalkyl; $R^{2a}$, $R^{2b}$, and $R^{2c}$ are each hydrogen; $R^3$ is

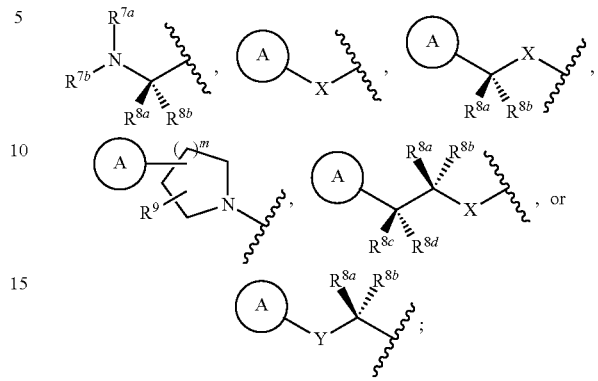

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl or heteroaryl; $R^{2a}$, $R^{2b}$, and $R^{2c}$ are each hydrogen; $R^3$ is

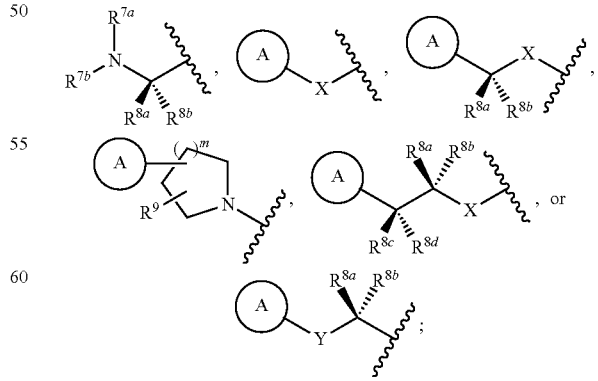

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl or heteroaryl, substituted with 0-3 substituents independently selected from fluoro, chloro, cyano, $C_1$-$C_6$ alkyl, $C_1$-$C_6$ fluoroalkyl, $C_1$-$C_6$ alkoxyalkyl, cyclopropyl, fluorocyclopropyl, $OR^5$, and $NR^{6a}R^{6b}$; wherein $R^5$ is hydrogen, $C_1$-$C_6$ alkyl or $C_1$-$C_6$ fluoroalkyl; and $R^{6a}$ and $R^{6b}$ are each independently hydrogen, $C_1$-$C_6$ alkyl, cyclopropyl, cyclobutyl, or $C_1$-$C_6$ heteroalkyl; or $R^{6a}$ and $R^{6b}$ together with the nitrogen atom to which they attach form a heterocycle; wherein each $R^{6a}$ and $R^{6b}$ are substituted with 0-3 fluorine atoms; $R^{2a}$, $R^{2b}$, and $R^{2c}$ are each hydrogen; $R^3$ is

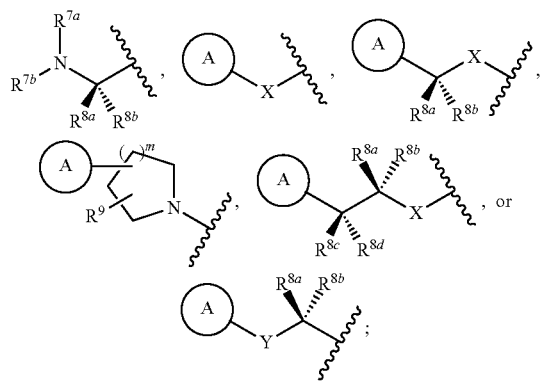

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is aryl substituted with 0-2 substituents independently selected from fluoro, chloro, $C_1$-$C_3$ alkyl, $C_1$-$C_3$ fluoroalkyl, $C_1$-$C_3$ alkoxyalkyl, and $OR^5$; wherein $R^5$ is hydrogen, $C_1$-$C_3$ alkyl, or $C_1$-$C_3$ fluoroalkyl; $R^{2a}$, $R^{2b}$, and $R^{2c}$ are each hydrogen; R3 is

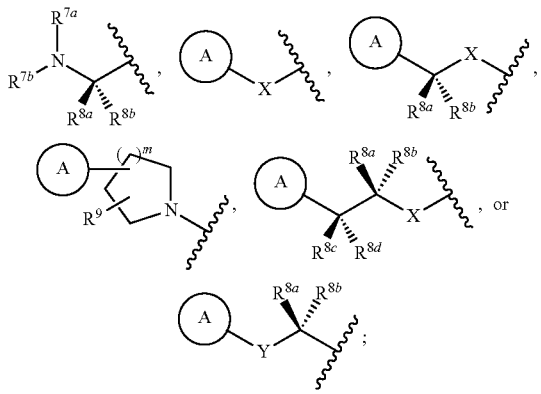

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is —$CONH_2$.

In certain embodiments, $R^1$ is heteroaryl substituted with 0-2 substituents independently selected from fluoro, chloro, $C_1$-$C_3$ alkyl, $C_1$-$C_3$ fluoroalkyl, and $C_1$-$C_3$ alkoxyalkyl; $R^{2a}$, $R^{2b}$, and $R^{2c}$ are each hydrogen; $R^3$ is

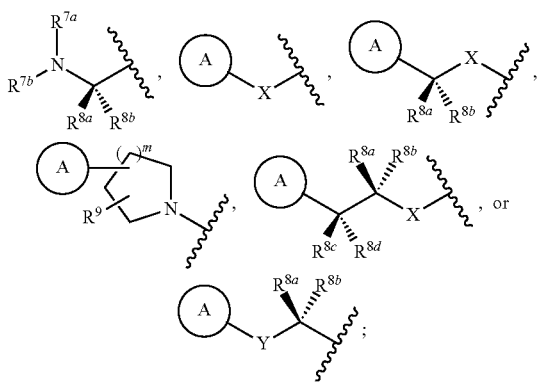

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms; $R^{8a}$, $R^{8b}$, $R^{8c}$, $R^{8d}$, $R^{8e}$ and $R^{8f}$ are each independently selected from hydrogen, fluoro, and methyl; $R^9$ at each occurrence is independently selected from fluoro, methyl, heterocycle, and heteroaryl; wherein 0-4 $R^9$ groups are present in each $R^3$; m is 0-3; $R^{10}$ is hydrogen, $C_1$-$C_3$ alkyl, or $C_1$-$C_3$ fluoroalkyl; A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^{11}$; wherein $R^{11}$ is independently selected from hydrogen, $C_1$-$C_3$ alkyl, and $C_1$-$C_3$ fluoroalkyl; $R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms; and $R^4$ is $—CONH_2$.

In certain embodiments, $R^1$ is phenyl substituted with 0-2 substituents independently selected from fluoro and methoxy; $R^{2a}$ is hydrogen; $R^{2b}$ and $R^{2c}$ are each independently hydrogen or fluoro; $R^3$ is

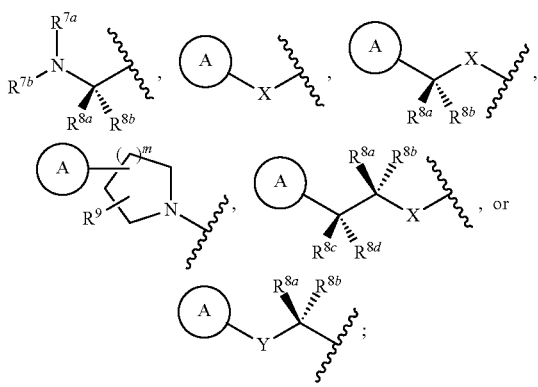

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_3$ alkyl and $C_3$-$C_5$ cycloalkyl, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$ are each independently selected from hydrogen and methyl; $R^9$ at each occurrence is independently selected from pyridyl and morpholinyl; wherein 0-1 $R^9$ groups are present in each $R^3$; m is 0 -1; $R^{10}$ is hydrogen or $C_1$-$C_3$ alkyl; A is pyridyl, pyrimidinyl, morpholinyl, pyrrolidinyl, piperidinyl, pyrazolinyl, tetrahydropyranyl, piperazinyl, 1,1-dioxothiomorpholinyl, 1,1-dioxo-1,4-thiazepanyl, 1,4-diazepanyl, 1,4-thiazepanyl, 1,4-oxazepanyl, azepanyl, 2-azaspiro[3.3]heptan-2-yl, decahydroquinolyl; wherein A is substituted with 0-2 substituents independently selected from fluoro, chloro, cyano, methyl, $—CH_2CF_3$, methoxy, $SO_2Me$, acyl, and cyclopropyl; and $R^4$ is $—CONH_2$.

In certain embodiments, $R^1$ is heteroaryl substituted with 0-1 substituents independently selected from $C_1$-$C_3$ alkyl; $R^{2a}$ is hydrogen; $R^{2b}$ and $R^{2c}$ are each independently hydrogen or fluoro; $R^3$ is

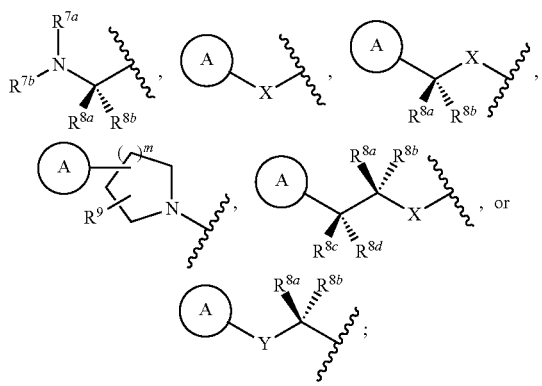

wherein X is a bond, $CR^{8e}R^{8f}$, O, or $NR^{10}$; Y is a bond, $CR^{8e}R^{8f}$, O, or $NR^{10}$; $R^{7a}$ and $R^{7b}$ are each independently selected from $C_1$-$C_3$ alkyl and $C_3$-$C_5$ cycloalkyl, or $R^{7a}$ and $R^{7b}$ together with the nitrogen atom to which they attach form a heterocycle; $R^{8a}$, $R^{8b}$, $R^{8c}$, $R^{8d}$, $R^{8e}$ and $R^{8f}$ are each independently selected from hydrogen and methyl; $R^9$ at each occurrence is independently selected from pyridyl and morpholinyl; wherein 0-1 $R^9$ groups are present in each $R^3$; m is 0 -1; $R^{10}$ is hydrogen or $C_1$-$C_3$ alkyl; A is pyridyl, pyrimidinyl, morpholinyl, pyrrolidinyl, piperidinyl, pyrazolinyl, tetrahydropyranyl, piperazinyl, 1,1-dioxothiomorpholinyl, 1,1-dioxo-1,4-thiazepanyl, 1,4-diazepanyl, 1,4-thiazepanyl, 1,4-oxazepanyl, azepanyl, 2-azaspiro[3.3]heptan-2-yl, decahydroquinolyl; wherein A is substituted with 0-2 substituents independently selected from fluoro, chloro, cyano, methyl, $—CH_2CF_3$, methoxy, $SO_2Me$, acyl, and cyclopropyl; and $R^4$ is $—CONH_2$.

Representative compounds of formula (I) include, but are not limited to:

1-(4-fluorophenyl)-4-oxo-6-(thiomorpholinomethyl)-1,4-dihydroquinoline-3-carboxamide;

1-(4-fluorophenyl)-6-(morpholinomethyl)-4-oxo-1,4-dihydroquinoline-3-carboxamide;

1-(4-fluorophenyl)-4-oxo-6-(piperidin-1-ylmethyl)-1,4-dihydroquinoline-3-carboxamide;

1-(4-fluorophenyl)-4-oxo-6-phenethyl-1,4-dihydroquinoline-3-carboxamide;

1-(4-fluorophenyl)-6-(4-methylphenethyl)-4-oxo-1,4-dihydroquinoline-3-carboxamide;

1-(4-fluorophenyl)-6-(3-methylphenethyl)-4-oxo-1,4-dihydroquinoline-3-carboxamide;

1-(4-fluorophenyl)-6-(2-methylphenethyl)-4-oxo-1,4-dihydroquinoline-3-carboxamide;
1-(4-fluorophenyl)-4-oxo-6-(2-(pyridin-4-yl)ethyl)-1,4-dihydroquinoline-3-carboxamide;
1-(4-fluorophenyl)-4-oxo-6-(2-(pyridin-3-yl)ethyl)-1,4-dihydroquinoline-3-carboxamide;
1-(4-fluorophenyl)-4-oxo-6-(2-(pyridin-2-yl)ethyl)-1,4-dihydroquinoline-3-carboxamide;
1-(4-fluorophenyl)-6-(methyl(pyridin-3-ylmethyl)amino)-4-oxo-1,4-dihydroquinoline-3-carboxamide;
1-(4-fluorophenyl)-4-oxo-6-(pyridin-3-yloxy)-1,4-dihydroquinoline-3-carboxamide;
1-(4-fluorophenyl)-6-(2-(2-methylpyrimidin-5-yl)ethyl)-4-oxo-1,4-dihydroquinoline-3-carboxamide;
1-(2-fluoro-4-methoxyphenyl)-6-(2-(2-methylpyrimidin-5-yl)ethyl)-4-oxo-1,4-dihydroquinoline-3-carboxamide;
1-(3-fluoro-4-methoxyphenyl)-6-(2-(2-methylpyrimidin-5-yl)ethyl)-4-oxo-1,4-dihydroquinoline-3-carboxamide;
1-(4-methoxyphenyl)-6-(2-(2-methylpyrimidin-5-yl)ethyl)-4-oxo-1,4-dihydroquinoline-3-carboxamide;
1-(4-fluorophenyl)-4-oxo-6-(pyridin-3-ylamino)-1,4-dihydroquinoline-3-carboxamide;
1-(4-fluorophenyl)-4-oxo-6-((pyridin-3-ylmethyl)amino)-1,4-dihydroquinoline-3-carboxamide;
1-(4-fluorophenyl)-6-(methyl(pyridin-4-yl)amino)-4-oxo-1,4-dihydroquinoline-3-carboxamide;
1-(4-fluorophenyl)-6-(methyl(pyridin-4-ylmethyl)amino)-4-oxo-1,4-dihydroquinoline-3-carboxamide;
1-(4-fluorophenyl)-6-((2-methylpyrimidin-5-yl)oxy)-4-oxo-1,4-dihydroquinoline-3-carboxamide;
1-(4-fluorophenyl)-6-((6-fluoropyridin-3-yl)oxy)-4-oxo-1,4-dihydroquinoline-3-carboxamide;
1-(4-fluorophenyl)-6-((5-fluoropyridin-3-yl)oxy)-4-oxo-1,4-dihydroquinoline-3-carboxamide;
1-(4-fluorophenyl)-6-((6-methylpyridin-3-yl)oxy)-4-oxo-1,4-dihydroquinoline-3-carboxamide;
1-(4-fluorophenyl)-6-(methyl(pyridin-3-yl)amino)-4-oxo-1,4-dihydroquinoline-3-carboxamide;
6-((6,6-difluoro-2-azaspiro[3.3]heptan-2-yl)methyl)-1-(4-fluorophenyl)-4-oxo-1,4-dihydroquinoline-3-carboxamide;
6-((4-cyclopropylpiperazin-1-yl)methyl)-1-(4-fluorophenyl)-4-oxo-1,4-dihydroquinoline-3-carboxamide;
1-(4-fluorophenyl)-6-((octahydroquinolin-1 (2H)-yl)methyl)-4-oxo-1,4-dihydroquinoline-3-carboxamide;
6-((4,7-dimethyl-1,4-diazepan-1-yl)methyl)-1-(4-fluorophenyl)-4-oxo-1,4-dihydroquinoline-3-carboxamide;
6-((cyclopentyl(methyl)amino)methyl)-1-(4-fluorophenyl)-4-oxo-1,4-dihydroquinoline-3-carboxamide;
6-((cyclopropyl(methyl)amino)methyl)-1-(4-fluorophenyl)-4-oxo-1,4-dihydroquinoline-3-carboxamide;
6-((1,4-thiazepan-4-yl)methyl)-1-(4-fluorophenyl)-4-oxo-1,4-dihydroquinoline-3-carboxamide;
6-((1,4-oxazepan-4-yl)methyl)-1-(4-fluorophenyl)-4-oxo-1,4-dihydroquinoline-3-carboxamide;
6-(azepan-1-ylmethyl)-1-(4-fluorophenyl)-4-oxo-1,4-dihydroquinoline-3-carboxamide;
1-(4-fluorophenyl)-6-((4-methoxypiperidin-1-yl)methyl)-4-oxo-1,4-dihydroquinoline-3-carboxamide;
6-((4-cyanopiperidin-1-yl)methyl)-1-(4-fluorophenyl)-4-oxo-1,4-dihydroquinoline-3-carboxamide;
1-(4-fluorophenyl)-6-((4-(methyl sulfonyl)piperidin-1-yl)methyl)-4-oxo-1,4-dihydroquinoline-3-carboxamide;
1-(4-fluorophenyl)-4-oxo-6-((4-(trifluoromethyl)piperidin-1-yl)methyl)-1,4-dihydroquinoline-3-carboxamide;
6-((4,4-difluoropiperidin-1-yl)methyl)-1-(4-fluorophenyl)-4-oxo-1,4-dihydroquinoline-3-carboxamide;
1-(4-fluorophenyl)-6-((2-methylmorpholino)methyl)-4-oxo-1,4-dihydroquinoline-3-carboxamide;
6-(((3,3-difluorocyclobutyl)(methyl)amino)methyl)-1-(4-fluorophenyl)-4-oxo-1,4-dihydroquinoline-3-carboxamide;
6-((cis-2,6-dimethylmorpholino)methyl)-1-(4-fluorophenyl)-4-oxo-1,4-dihydroquinoline-3-carboxamide
1-(4-fluorophenyl)-4-oxo-6-((4-(2,2,2-trifluoroethyl)piperazin-1-yl)methyl)-1,4-dihydroquinoline-3-carboxamide;
6-((4-acetylpiperazin-1-yl)methyl)-1-(4-fluorophenyl)-4-oxo-1,4-dihydroquinoline-3-carboxamide;
1-(4-fluorophenyl)-6-((4-(methylsulfonyl)piperazin-1-yl)methyl)-4-oxo-1,4-dihydroquinoline-3-carboxamide;
6-((1,1-dioxidothiomorpholino)methyl)-1-(4-fluorophenyl)-4-oxo-1,4-dihydroquinoline-3-carboxamide;
6-((1,1-dioxido-1,4-thiazepan-4-yl)methyl)-1-(4-fluorophenyl)-4-oxo-1,4-dihydroquinoline-3-carboxamide;
6-((3,3-difluoropyrrolidin-1-yl)methyl)-1-(4-fluorophenyl)-4-oxo-1,4-dihydroquinoline-3-carboxamide;
1-(4-fluorophenyl)-6-((4-methylpiperazin-1-yl)methyl)-4-oxo-1,4-dihydroquinoline-3-carboxamide;
1-(4-fluorophenyl)-6-((6-methylpyridin-3-yl)methoxy)-4-oxo-1,4-dihydroquinoline-3-carboxamide;
1-(3-methylisothiazol-5-yl)-6-(2-(2-methylpyrimidin-5-yl)ethyl)-4-oxo-1,4-dihydroquinoline-3-carboxamide;
1-(4-fluorophenyl)-4-oxo-6-(1-(pyridin-4-yl)ethoxy)-1,4-dihydroquinoline-3-carboxamide;
1-(4-fluorophenyl)-6-((2-methylpyridin-4-yl)methoxy)-4-oxo-1,4-dihydroquinoline-3-carboxamide;
1-(4-fluorophenyl)-4-oxo-6-(pyridin-4-ylmethoxy)-1,4-dihydroquinoline-3-carboxamide;
1-(4-fluorophenyl)-4-oxo-6-((2-(pyridin-4-yl)ethyl)amino)-1,4-dihydroquinoline-3-carboxamide;
1-(4-fluorophenyl)-4-oxo-6-((2-(pyridin-3-yl)ethyl)amino)-1,4-dihydroquinoline-3-carboxamide;
1-(4-fluorophenyl)-6-((2-morpholinoethyl)amino)-4-oxo-1,4-dihydroquinoline-3-carboxamide;
1-(4-fluorophenyl)-6-((2-methylpyrimidin-5-yl)methoxy)-4-oxo-1,4-dihydroquinoline-3-carboxamide;
1-(4-fluorophenyl)-4-oxo-6-(1-(pyridin-3-yl)ethoxy)-1,4-dihydroquinoline-3-carboxamide;
1-(4-fluorophenyl)-6-(methyl((2-methylpyrimidin-5-yl)methyl)amino)-4-oxo-1,4-dihydroquinoline-3-carboxamide;
1-(4-fluorophenyl)-6-(((3-fluoropyridin-4-yl)oxy)methyl)-4-oxo-1,4-dihydroquinoline-3-carboxamide;
1-(4-fluorophenyl)-6-(((2-methylpyridin-4-yl)oxy)methyl)-4-oxo-1,4-dihydroquinoline-3-carboxamide;
1-(4-fluorophenyl)-4-oxo-6-(((2-(trifluoromethyl)pyridin-4-yl)oxy)methyl)-1,4-dihydroquinoline-3-carboxamide;
1-(4-fluorophenyl)-6-(((2-methylpyrimidin-5-yl)oxy)methyl)-4-oxo-1,4-dihydroquinoline-3-carboxamide;
1-(4-fluorophenyl)-4-oxo-6-(((6-(trifluoromethyl)pyridin-3-yl)oxy)methyl)-1,4-dihydroquinoline-3-carboxamide;
1-(4-fluorophenyl)-4-oxo-6-(((tetrahydro-2H-pyran-4-yl)methyl)amino)-1,4-dihydroquinoline-3-carboxamide;
6-(((6-chloropyridin-3-yl)oxy)methyl)-1-(4-fluorophenyl)-4-oxo-1,4-dihydroquinoline-3-carboxamide;
1-(4-fluorophenyl)-4-oxo-6-(2-(pyridin-3-yl)piperidin-1-yl)-1,4-dihydroquinoline-3-carboxamide;
1-(4-fluorophenyl)-6-(((2-fluoropyridin-3-yl)oxy)methyl)-4-oxo-1,4-dihydroquinoline-3-carboxamide;
1-(4-fluorophenyl)-4-oxo-6-(2-(pyridin-3-yl)pyrrolidin-1-yl)-1,4-dihydroquinoline-3-carboxamide;
1-(4-fluorophenyl)-6-(((6-methylpyridin-3-yl)oxy)methyl)-4-oxo-1,4-dihydroquinoline-3-carboxamide;
6-(ethyl(pyridin-3-ylmethyl)amino)-1-(4-fluorophenyl)-4-oxo-1,4-dihydroquinoline-3-carboxamide;

1-(4-fluorophenyl)-4-oxo-6-(5H-pyrrolo[3,4-b]pyridin-6 (7H)-yl)-1,4-dihydroquinoline-3-carboxamide;
1-(4-fluorophenyl)-4-oxo-6-(pyridin-3-ylmethoxy)-1,4-dihydroquinoline-3-carboxamide;
1-(4-fluorophenyl)-6-(methyl(pyridin-3-ylmethyl)amino)-4-oxo-1,4-dihydroquinoline-3-carbonitrile;
1-(4-fluorophenyl)-6-(((6-fluoropyridin-3-yl)oxy)methyl)-4-oxo-1,4-dihydroquinoline-3-carboxamide;
1-(4-fluorophenyl)-4-oxo-6-(2-(2-(trifluoromethyl)pyridin-4-yl)ethyl)-1,4-dihydroquinoline-3-carboxamide;
1-(4-fluorophenyl)-4-oxo-6-(2-(6-(trifluoromethyl)pyridin-3-yl)ethyl)-1,4-dihydroquinoline-3-carboxamide;
1-(4-fluorophenyl)-6-(2-(5-fluoropyridin-3-yl)ethyl)-4-oxo-1,4-dihydroquinoline-3-carboxamide;
8-fluoro-1-(4-fluorophenyl)-6-(2-(2-methylpyrimidin-5-yl)ethyl)-4-oxo-1,4-dihydroquinoline-3-carboxamide;
1-(4-fluorophenyl)-6-(3-morpholinopyrrolidin-1-yl)-4-oxo-1,4-dihydroquinoline-3-carboxamide;
8-fluoro-1-(4-fluorophenyl)-6-(methyl(pyridin-3-ylmethyl)amino)-4-oxo-1,4-dihydroquinoline-3-carboxamide;
1-(4-fluorophenyl)-6-(1-methyl-1H-pyrazol-4-yl)-4-oxo-1,4-dihydroquinoline-3-carboxamide;
1-(4-fluorophenyl)-6-(2-methylpyrimidin-5-yl)-4-oxo-1,4-dihydroquinoline-3-carboxamide;
1-(4-fluorophenyl)-4-oxo-6-(pyridin-4-yl)-1,4-dihydroquinoline-3-carboxamide;
1-(4-fluorophenyl)-4-oxo-6-(pyridin-3-yl)-1,4-dihydroquinoline-3-carboxamide;
(S)-1-(4-fluorophenyl)-6-((2-methylmorpholino)methyl)-4-oxo-1,4-dihydroquinoline-3-carboxamide;
(R)-1-(4-fluorophenyl)-6-((2-methylmorpholino)methyl)-4-oxo-1,4-dihydroquinoline-3-carboxamide;
6-((2,2-dimethylmorpholino)methyl)-1-(4-fluorophenyl)-4-oxo-1,4-dihydroquinoline-3-carboxamide;
6-(((3,3-difluorocyclobutyl)(methyl)amino)methyl)-8-fluoro-1-(4-fluorophenyl)-4-oxo-1,4-dihydroquinoline-3-carboxamide;
6-((cis-2,6-dimethylmorpholino)methyl)-8-fluoro-1-(4-fluorophenyl)-4-oxo-1,4-dihydroquinoline-3-carboxamide;
8-fluoro-1-(4-fluorophenyl)-6-((2-methylmorpholino)methyl)-4-oxo-1,4-dihydroquinoline-3-carboxamide;
6-((4,4-difluoropiperidin-1-yl)methyl)-8-fluoro-1-(4-fluorophenyl)-4-oxo-1,4-dihydroquinoline-3-carboxamide;
6-((3,3-difluoropyrrolidin-1-yl)methyl)-8-fluoro-1-(4-fluorophenyl)-4-oxo-1,4-dihydroquinoline-3-carboxamide;
7-fluoro-1-(4-fluorophenyl)-6-(methyl(pyridin-3-ylmethyl)amino)-4-oxo-1,4-dihydroquinoline-3-carboxamide; and
7-fluoro-1-(4-fluorophenyl)-6-(2-(2-methylpyrimidin-5-yl)ethyl)-4-oxo-1,4-dihydroquinoline-3-carboxamide;
and pharmaceutically acceptable salt thereof.

Compound names are assigned by using Struct=Name naming algorithm as part of CHEMDRAW® ULTRA v. 12.0.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

It should be understood that the compound may possess tautomeric forms, as well as geometric isomers, and that these also constitute an aspect of the invention.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}C$, $^{13}N$ $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A. Allosteric Modulation of mGlu$_2$

The disclosed compounds may act or function as non-competitive antagonists, allosteric inhibitors, allosteric antagonists, or negative allosteric modulators (NAM) of mGlu$_2$. The compounds may be procognitive and neuroprotective even in the presence of mGlu$_2$ dysfunction.

Compounds of formula (I) can inhibit mGlu$_2$ with an IC$_{50}$ ranging from about 1 nM to about 30 µM. The compounds may have an IC$_{50}$ of about 30 µM, about 29 µM, about 28 µM, about 27 µM, about 26 µM, about 25 µM, about 24 µM, about 23 µM, about 22 µM, about 21 µM, about 20 µM, about 19 µM, about 18 µM, about 17 µM, about 16 µM, about 15 µM, about 14 µM, about 13 µM, about 12 µM, about 11 µM, about 10 µM, about 9 µM, about 8 µM, about 7 µM, about 6 µM, about 5 µM, about 4 µM, about 3 µM, about 2 µM, about 1 µM, about 950 nM, about 900 nM, about 850 nM, about 800 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 50 nM, about 10 nM, about 5 nM, or about 1 nM. Compounds of formula (I) can inhibit mGlu$_2$ with an IC50 of less than 30 µM, less than 29 µM, less than 28 µM, less than 27 µM, less than 26 µM, less than 25 µM, less than 24 µM, less than 23 µM, less than 22 µM, less than 21 µM, less than 20 µM, less than 19 µM, less than 18 µM, less than 17 µM, less than 16 µM, less than 15 µM, less than 14 µM, less than 13 µM, less than 12 µM, less than 11 µM, less than 10 µM, less than 9 µM, less than 8 µM, less than 7 µM, less than 6 µM, less than 5 µM, less than 4 µM, less than 3 µM, less than 2 µM, less than 1 µM, less than 950 nM, less than 900 nM, less than 850 nM, less than 800 nM, less than 850 nM, less than 800 nM, less than 750 nM, less than 700 nM, less than 650 nM, less than 600 nM, less than 550 nM, less than 500 nM, less than 450 nM, less than 400 nM, less than 350 nM, less than 300 nM, less than 250 nM, less than 200 nM, less than 150 nM, less than 100 nM, less than 50 nM, less than 10 nM, less than 5 nM, or less than 1 nM.

Compounds of formula (I) may be selective modulators of mGlu$_2$ over mGlu$_3$. The compounds may have a ratio of mGlu$_2$ IC$_{50}$ to mGlu$_3$ EC$_{50}$ of at least 100, at least 95, at least 90, at least 85, at least 80, at least 75, at least 70, at least 64, at least 60, at least 55, at least 50, at least 45, at least 40, at least 35, at least 33, at least 31, at least 30, at least 29, at least 28, at least 27, at least 26, at least 25, at least 24, at least 23, at least 22, at least 21, at least 20, at least 19, at least 18, at least 17, at least 16, at least 15, at least 14, at least 13, at least 12, at least 11, at least 10, at least 9, at least 8, at least 7, at least 6, at least 5, at least 4, at least 3, or at least 2. Compounds of formula (I) may have a ratio of mGlu$_2$ IC$_{50}$ to mGlu$_3$ EC$_{50}$ of about 100, about 95, about 90, about 85, about 80, about 75, about 70, about 64, about 60, about 55, about 50, about 45, about 40, about 35, about 33, about 31, about 30, about 29, about 28, about 27, about 26, about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, or about 2.

Compounds of formula (I) may be selective modulators of mGlu$_2$ over mGlu$_5$. The compounds may have a ratio of mGlu$_2$ IC$_{50}$ to mGlu$_5$ EC$_{50}$ of at least 100, at least 95, at least 90, at least 85, at least 80, at least 75, at least 70, at least 64, at least 60, at least 55, at least 50, at least 45, at least 40, at least 35, at least 33, at least 31, at least 30, at least 29, at least 28, at least 27, at least 26, at least 25, at least 24, at least 23, at least 22, at least 21, at least 20, at least 19, at least 18, at least 17, at least 16, at least 15, at least 14, at least 13, at least 12, at least 11, at least 10, at least 9, at least 8, at least 7, at least 6, at least 5, at least 4, at least 3, or at least 2. Compounds of formula (I) may have a ratio of mGlu$_2$ IC$_{50}$ to mGlu$_5$ EC$_{50}$ of about 100, about 95, about 90, about 85, about 80, about 75, about 70, about 64, about 60, about 55, about 50, about 45, about 40, about 35, about 33, about 31, about 30, about 29, about 28, about 27, about 26, about 25, about 24, about 23, about 22, about 21, about 20, about 19, about 18, about 17, about 16, about 15, about 14, about 13, about 12, about 11, about 10, about 9, about 8, about 7, about 6, about 5, about 4, about 3, or about 2.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, thrichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

B. General Synthesis

Compounds of formula (I) may be prepared by synthetic processes or by metabolic processes. Preparation of the compounds by metabolic processes includes those occurring in the human or animal body (in vivo) or processes occurring in vitro.

Compounds of formula (I), wherein the groups $R^1$, $R^{2a}$, $R^{2b}$, $R^{2c}$, $R^3$, and $R^4$ have the meanings as set forth in the Summary of the Invention section unless otherwise noted, can be synthesized as shown in Schemes 1-18.

Abbreviations which have been used in the descriptions of the Schemes that follow are: D$^t$BAD for di-tert-butylazodicarboxylate; BuLi for butyllithium; dba for dibenzylideneacetone; DIEA for diisopropylethylamine; DME for dimethoxyethane; DMF for dimethylformamide; dppf for 1,1'-bis(diphenylphosphino)ferrocene; EDC for N-(3-dimethylaminopropyl)-N'-ethylcarbodiimide hydrochloride; HATU for N-[(dimethylamino)-1H-1,2,3-triazolo-[4,5-b]pyridin-1-ylmethylene]-N-methylmethanaminium hexafluorophosphate N-oxide; HOBt for 1-hydroxybenzotriazole; Me$_2$CO for acetone; MeOH for methanol; NEt$_3$ for triethylamine; n-PrOH for n-propanol; PhMe for toluene; tBuXPhos for 2-di-tert-butylphosphino-2',4',6'-triisopropylbiphenyl; THF for tetrahydrofuran; XantPhos for 4,5-bis(diphenylphosphino)-9,9-dimethylxanthene.

Scheme 1. Synthesis of intermediate v

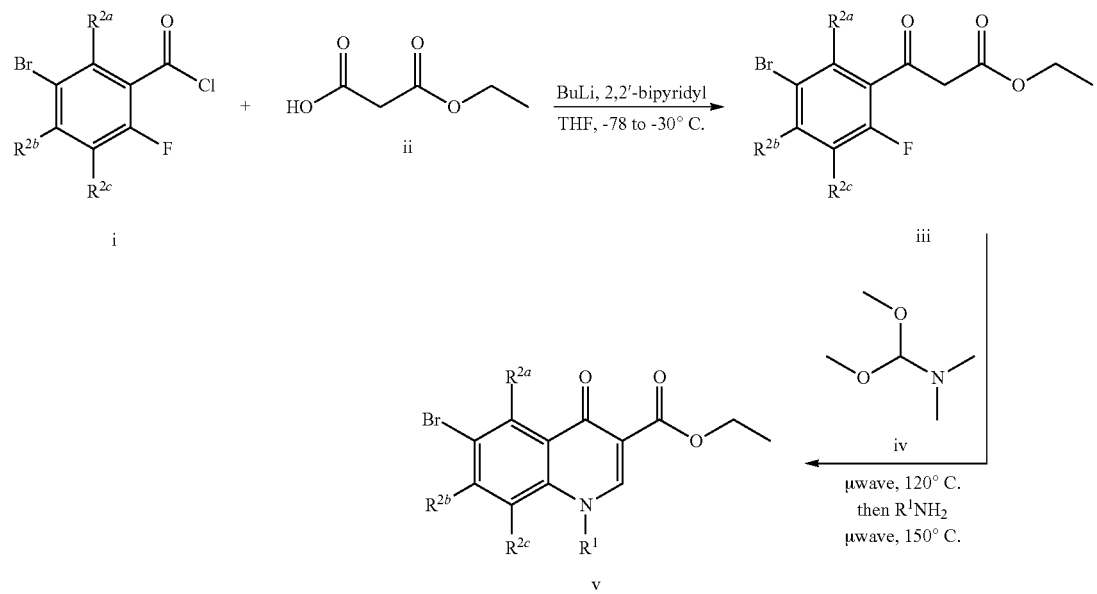

As shown in Scheme 1, intermediate v, wherein each $R^2$ is as defined in the Summary of the Invention, can be prepared from substituted benzoyl chloride i. Treatment of 3-ethoxy-3-oxopropanoic acid ii with butyllithium, followed by addition of i, can result in formation of β-ketoester iii. β-ketoester iii can be treated with DMF-DMA (iv), followed by addition of $R^1NH_2$, wherein $R^1$ is as defined in the Summary of the Invention, to provide intermediate v.

Scheme 2. Synthesis of intermediate vi

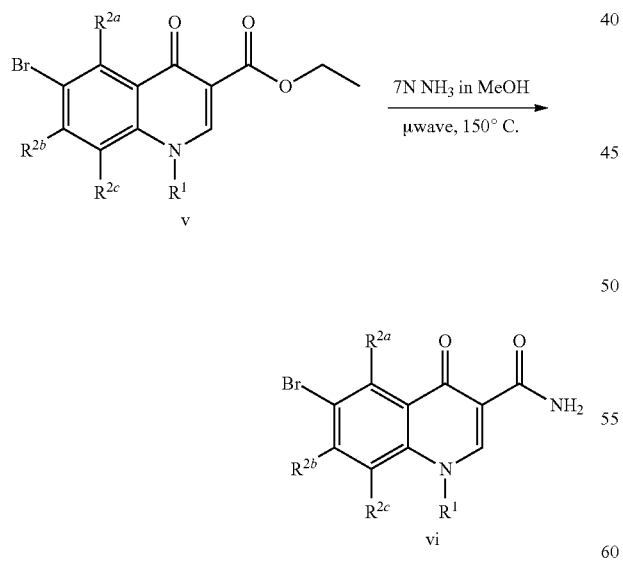

Scheme 3. Synthesis of intermediates x and xi

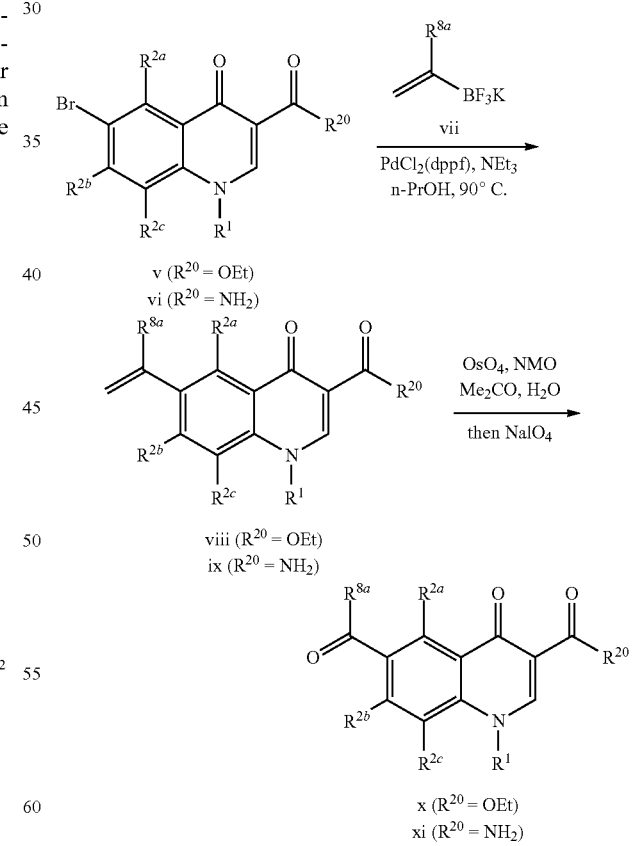

Scheme 2 illustrates the conversion of intermediate v to intermediate vi. Intermediate v can be treated with a solution of ammonia in methanol with heating to give intermediate vi.

Scheme 3 illustrates the preparation of intermediate x from intermediate v and the preparation of intermediate xi from intermediate vi. Bromides v and vi may be converted to alkenes viii and ix, respectively, via a palladium catalyzed coupling reaction with potassium vinyltrifluoroborate vii, wherein $R^{8a}$ is as defined in the Summary of the Invention. Treatment of intermediates viii and ix with osmium tetroxide and 4-methylmorpholine N-oxide (NMO) can form the corresponding diols, which can be reacted in situ with sodium (meta)periodate to afford intermediates x and xi, respectively.

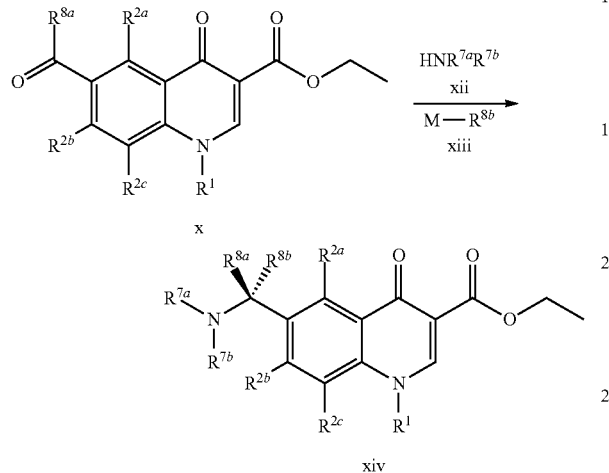

Scheme 4. Synthesis of intermediate xiv

Scheme 4 illustrates the conversion of intermediate x to intermediate xiv. Intermediate x can be treated with an amine xii, wherein $R^{7a}$ and $R^{7b}$ are as defined in the Summary of the Invention, and a reagent xiii, wherein M is a group that renders $R^{8b}$ nucleophilic, wherein $R^{8b}$ is as defined in the Summary of the Invention, to provide intermediate xiv.

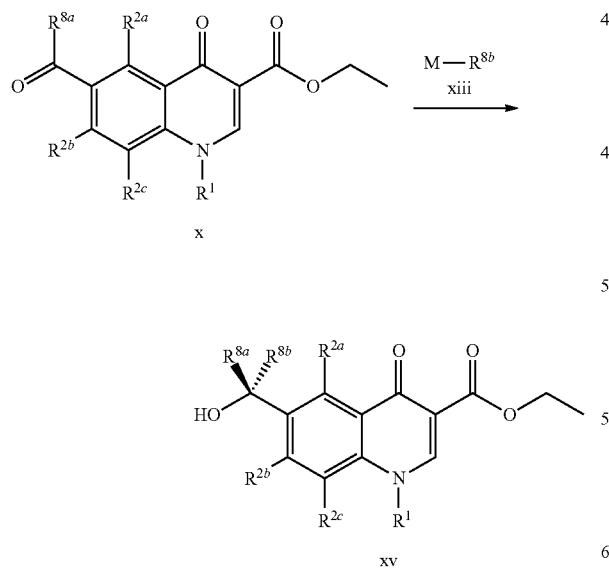

Scheme 5. Synthesis of intermediate xv

Scheme 5 illustrates the conversion of intermediate x to intermediate xv. Intermediate x can be treated with a reagent xiii, wherein M is a group that renders $R^{8b}$ nucleophilic, wherein $R^{8b}$ is as defined in the Summary of the Invention, to provide intermediate xv.

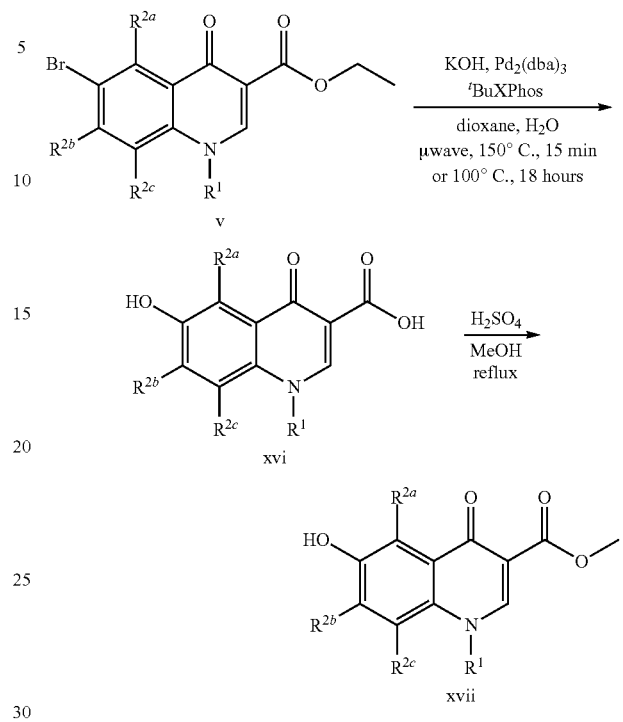

Scheme 6. Synthesis of intermediate xvii

Scheme 6 illustrates the conversion of intermediate v to intermediate xvii. Intermediate v can be converted to intermediate xvi via a palladium catalyzed hydroxylation. Intermediate xvi can be treated with acid in methanol with heating to afford intermediate xvii.

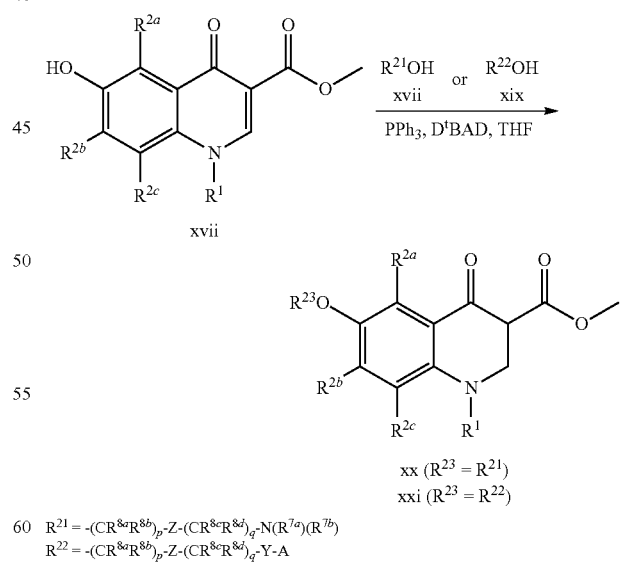

Scheme 7. Synthesis of intermediates xx and xxi $R^{21}$ = -(CR$^{8a}$R$^{8b}$)$_p$-Z-(CR$^{8c}$R$^{8d}$)$_q$-N(R$^{7a}$)(R$^{7b}$)
$R^{22}$ = -(CR$^{8a}$R$^{8b}$)$_p$-Z-(CR$^{8c}$R$^{8d}$)$_q$-Y-A Scheme 7 illustrates the preparation of intermediate xx from intermediate xvii and the preparation of intermediate xxi from intermediate xvii. Intermediate xvii can be reacted in a Mitsunobu reaction with alcohols xviii and xix, wherein $R^{7a}$, $R^{7b}$, $R^{8a}$, $R^{8b}$, $R^{8c}$, $R^{8d}$, Z, p, q, Y, and A are as defined in the Summary of the Invention, to produce intermediates xx and xxi, respectively.

Scheme 8. Synthesis of intermediate xxiii

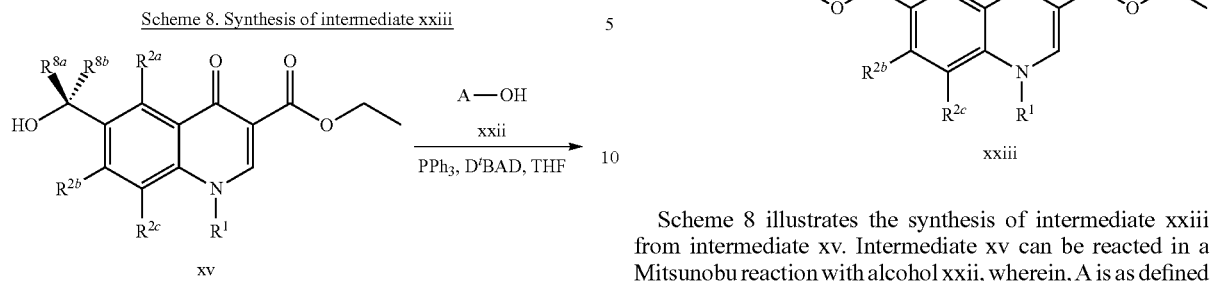

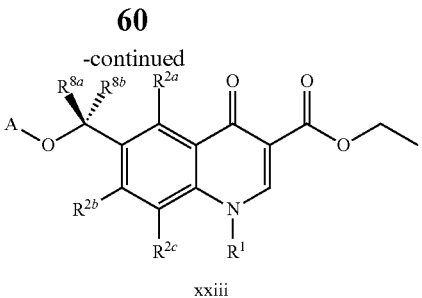

xxiii

Scheme 8 illustrates the synthesis of intermediate xxiii from intermediate xv. Intermediate xv can be reacted in a Mitsunobu reaction with alcohol xxii, wherein, A is as defined in the Summary of the Invention, to produce intermediate xxiii, respectively.

Scheme 9. Synthesis of intermediates xxviii, xxix, xxx and xxxi

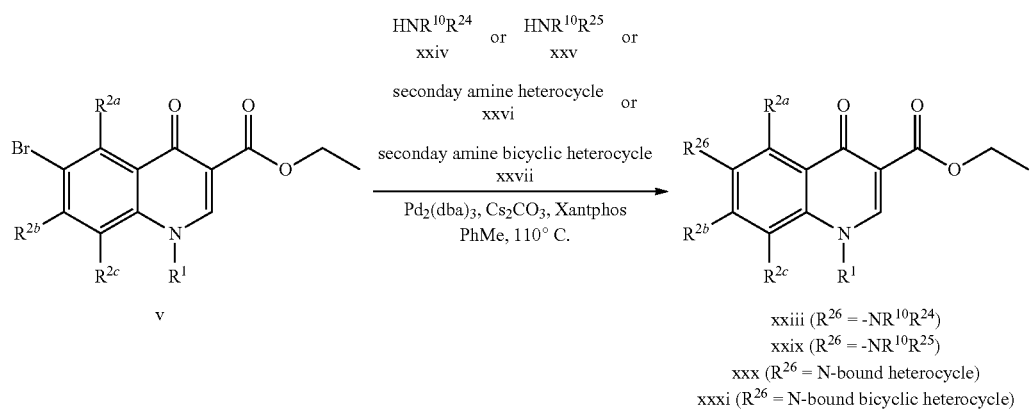

$R^{24}$ = -$(CR^{8a}R^{8b})_p$-Z-$(CR^{8c}R^{8d})_q$-N$(R^{7a})(R^{7b})$
$R^{25}$ = -$(CR^{8a}R^{8b})_p$-Z-$(CR^{8c}R^{8d})_q$-Y-A

Scheme 9 illustrates the preparation of intermediate xxviii from intermediate v, the preparation of intermediate xxix from intermediate v, the preparation of intermediate xxx from intermediate v, and the preparation of intermediate xxxi from intermediate v. Intermediate v may be reacted with amines xxiv, xxv, xxvi, and xxvii, wherein $R^{7a}$, $R^{7b}$, $R^{8a}$, $R^{8b}$, $R^{8c}$, $R^{8d}$, Z, p, q, Y, and A are as defined in the Summary of the Invention, in a Buchwald-Hartwig palladium catalyzed coupling to produce intermediates xxviii, xxix, xxx, and xxxi, respectively.

Scheme 10. Synthesis of intermediates xxxiv and xxxv

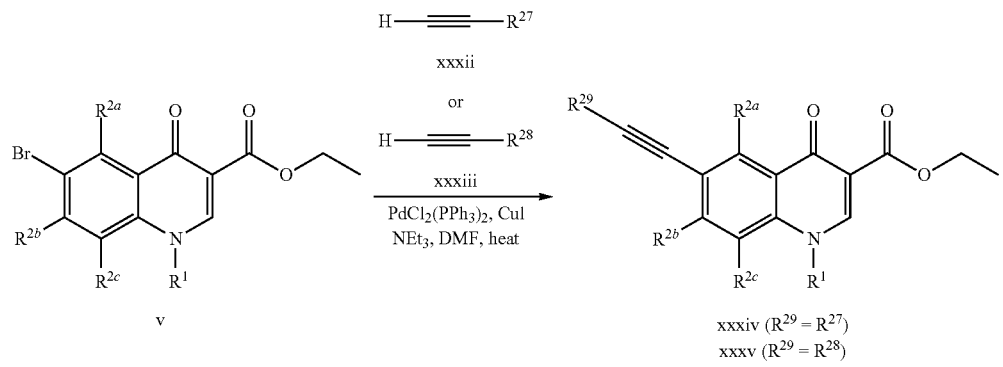

$R^{27}$ = -$(CR^{8a}R^{8b})_p$-Z-$(CR^{8c}R^{8d})_q$-N$(R^{7a})(R^{7b})$
$R^{28}$ = -$(CR^{8a}R^{8b})_p$-Z-$(CR^{8c}R^{8d})_q$-Y-A

Scheme 10 illustrates the synthesis of intermediate xxxiv from intermediate v and the preparation of intermediate xxxv from intermediate v. Intermediate v can be reacted with alkynes xxxii and xxxiii, wherein $R^{7a}$, $R^{7b}$, $R^{8a}$, $R^{8b}$, $R^{8c}$, $R^{8d}$, Z, q, Y, and A are as defined in the Summary of the Invention and wherein p is 0 or 1, in a Sonogashira coupling to provide intermediates xxxiv and xxxv, respectively.

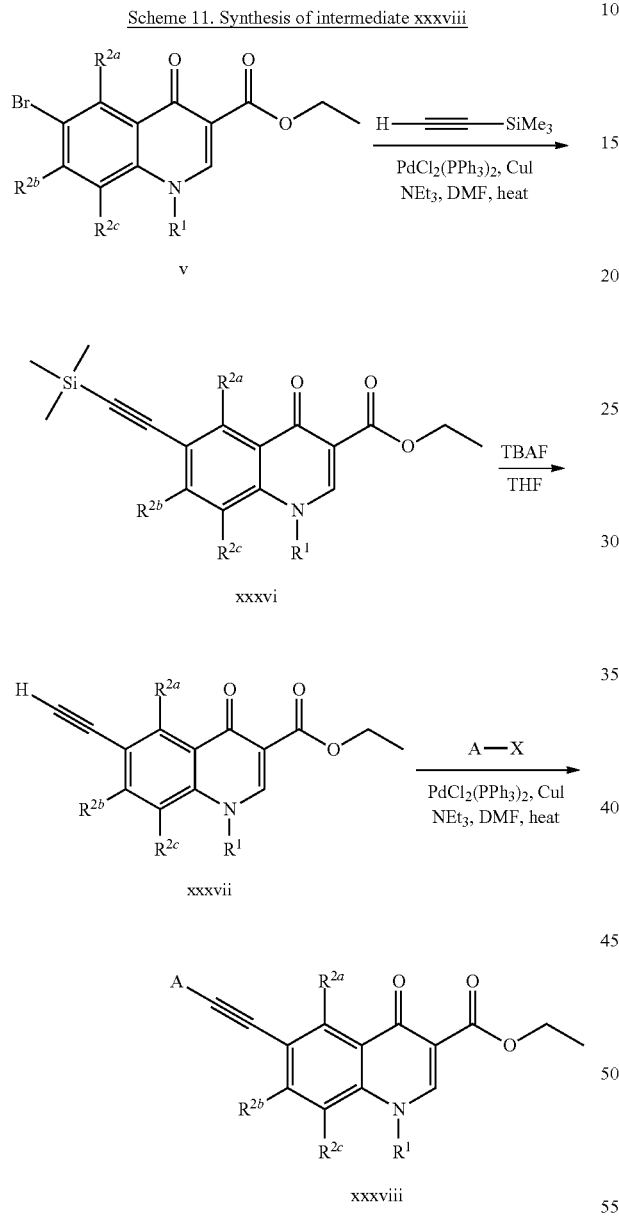

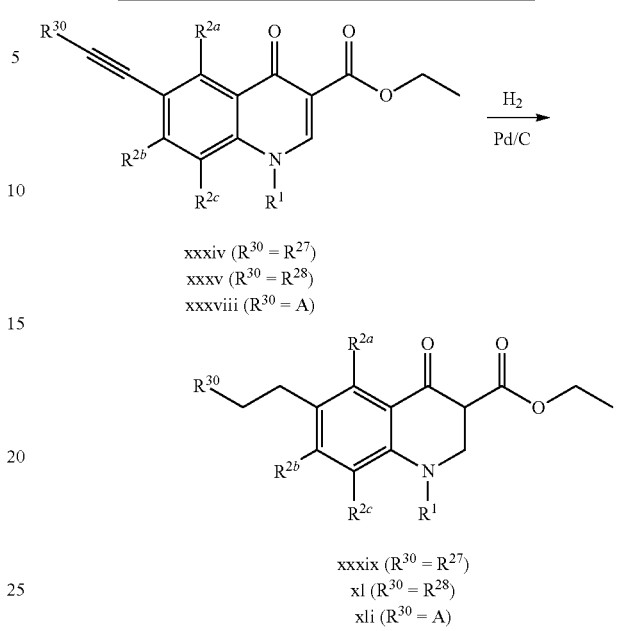

Scheme 12 illustrates the synthesis of intermediate xxxix from intermediate xxxiv, the preparation of intermediate xl from intermediate xxxv, and the preparation of intermediate xli from intermediate xxxviii. Intermediates xxxiv, xxxv, and xxxviii can be reduced via a palladium catalyzed hydrogenation to afford intermediates xxxix, xl, and xli, respectively.

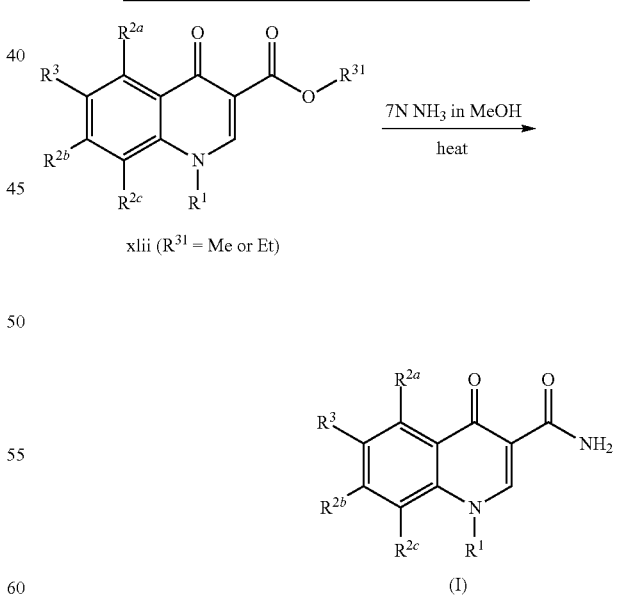

Scheme 11 illustrates the conversion of intermediate v to intermediate xxxviii. Reaction of intermediate v with ethynyltrimethylsilane in a Sonogashira coupling can provide intermediate xxxvi. Treatment of intermediate xxxvi with tetrabutylammonium fluoride can yield intermediate xxxvii. Coupling of intermediate xxxvii with A—X, wherein A is as defined in the Summary of the Invention and wherein X is chloride, bromide, iodide, or trifluoromethanesulfonate, under Sonogashira conditions can afford intermediate xxxviii.

As illustrated in Scheme 13, the compound of formula (I) can be prepared from intermediate xlii. Treatment of intermediate xlii, wherein $R^3$ is as defined in the Summary of the invention, with ammonia in methanol with heating can provide the compound of formula (I).

Scheme 14. Sythesis of the compound of fomula (I)

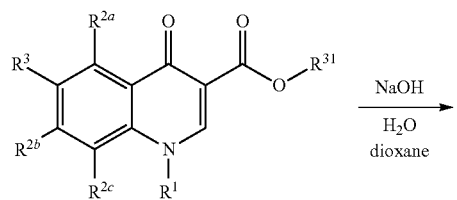

xlii (R³¹ = Me or Et)

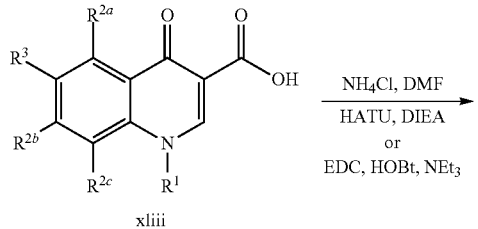

xliii (I)

Alternatively, the compound of formula (I) can be prepared from intermediate xlii, as illustrated in Scheme 14, by a two-step process. Hydrolysis of intermediate xlii, wherein $R^3$ is as defined in the Summary of the invention, with aqueous hydroxide can provide intermediate acid xliii. Intermediate xliii can be converted to the compound of formula (I) using ammonium chloride and a suitable coupling reagent.

Scheme 15. Synthesis of the compound of formula (I)

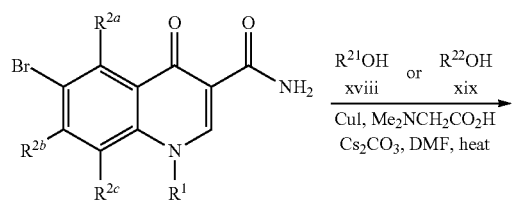

vi

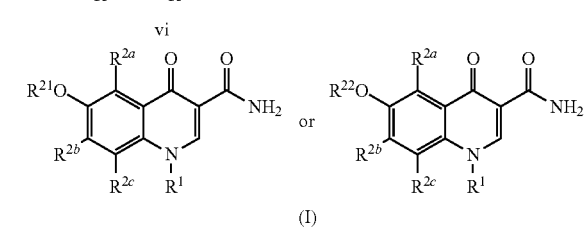

(I)

$R^{21} = -(CR^{8a}R^{8b})_p-Z-(CR^{8c}R^{8d})_q-N(R^{7a})(R^{7b})$
$R^{22} = -(CR^{8a}R^{8b})_p-Z-(CR^{8c}R^{8d})_q-Y-A$

As illustrated in Scheme 15, the compound of formula (I) can also be prepared from intermediate vi. Reaction of intermediate vi with alcohols such as xviii and xix, wherein $R^{7a}$, $R^{7b}$, $R^{8a}$, $R^{8b}$, $R^{8c}$, $R^{8d}$, Z, q, Y, and A are as defined in the Summary of the Invention, in an Ullmann coupling can afford the compound of formula (I).

Scheme 16. Synthesis of the compound of formula (I)

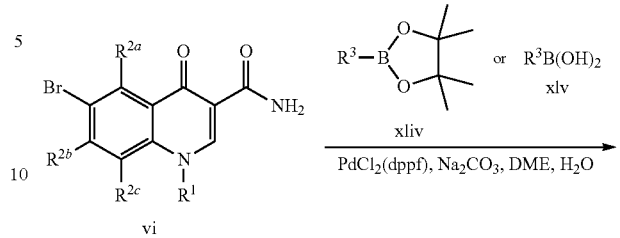

vi

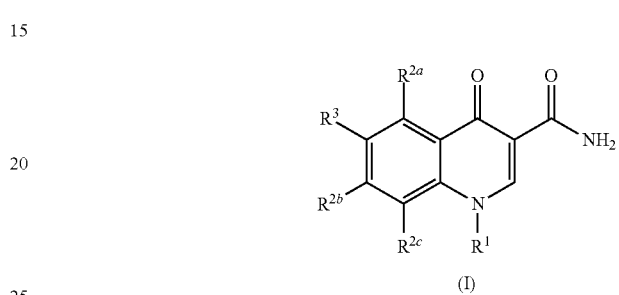

(I)

Alternatively, as illustrated in Scheme 16, the compound of formula (I) can be prepared from intermediate vi. Intermediate vi can be reacted in a palladium catalyzed Suzuki coupling reaction with reagents such as xliv or xlv, wherein $R^3$ is as defined in the Summary of the invention, to yield the compound of formula (I).

Scheme 17. Synthesis of the compound of formula (I)

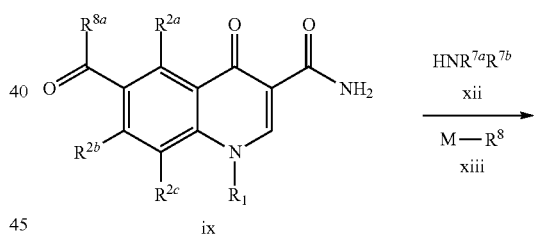

ix

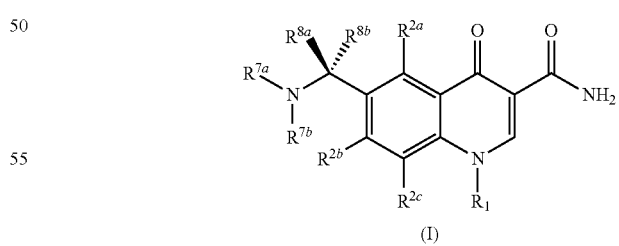

(I)

As illustrated in Scheme 17, the compound of formula (I) can also be prepared from intermediate ix. Intermediate ix can be treated with an amine xii, wherein $R^{7a}$ and $R^{7b}$ are as defined in the Summary of the Invention, and a reagent xiii, wherein M is a group that renders $R^{8b}$ nucleophilic, wherein $R^{8b}$ is as defined in the Summary of the Invention, to provide the compound of formula (I).

Scheme 18. Synthesis of the compound of formula (I)

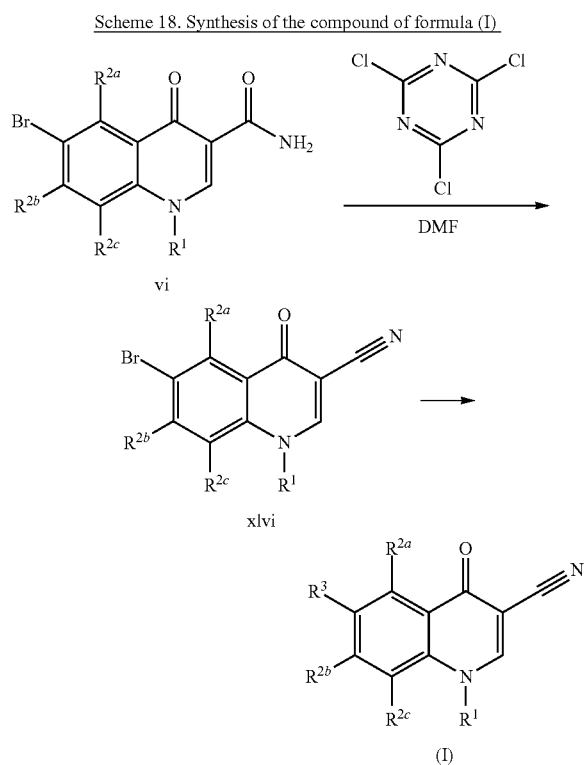

As illustrated in Scheme 18, the compound of formula (I), wherein $R^4$ is cyano, can be prepared from intermediate vi. The primary amide of vi can be dehydrated through treatment with an appropriate reagent such as cyanuric chloride to afford intermediate xlvi. Conversion of intermediate xlvi into the compound of formula (I) can be accomplished using methods analogous to those described in Schemes 3-12 and Schemes 15-17.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. Pharmaceutical Compositions

The disclosed compounds may be incorporated into pharmaceutical compositions suitable for administration to a subject (such as a patient, which may be a human or non-human).

The pharmaceutical compositions may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention [e.g., a compound of formula (I)] are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eyedrop, in a topical oil-based formulation, injection, inhalation (either through the mouth or the nose), implants, or oral, buccal, parenteral, or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of *theobroma*. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active [e.g., compound of formula (I)] and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound [e.g., a compound of formula (I)], and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound [e.g., a compound of formula (I)], and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the medicament. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified Montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

4. Methods of Treatment

The disclosed compounds and compositions may be used in methods for treatment of $mGlu_2$ related medical disorders and/or diseases. The methods of treatment may comprise administering to a subject in need of such treatment a composition comprising a therapeutically effective amount of the compound of formula (I).

The compositions can be administered to a subject in need thereof to modulate $mGlu_2$, for a variety of diverse biological processes. The present disclosure is directed to methods for administering the composition to inhibit $mGlu_2$, a GPCR that plays a role in synaptic plasticity, which directly effects cognitive function and memory, for example.

The compositions may be useful for treating and preventing certain diseases and disorders in humans and animals related to $mGlu_2$ dysfunction. Treatment or prevention of such diseases and disorders can be effected by modulating $mGlu_2$ in a subject, by administering a compound or composition of the invention, either alone or in combination with another active agent as part of a therapeutic regimen to a subject in need thereof.

a. Depression

Antidepressant-like effects of the $mGlu_{2/3}$ receptor antagonists, MGS0039 and LY341495, were first demonstrated in the rat forced swim test (FST) and mouse tail-suspension test (TST) using normal animals (Chaki et al. *Neuropharmacology,* 2004, 46, 457-467). More recently, studies have attempted to evaluate the effects of these drugs in paradigms implicated in the etiology of human depression. MGS0039 exhibited antidepressant effects in the learned helplessness test where treatment with MGS0039 for 7 days significantly reduced the number of escape failures (Yoshimizu et al. *Psychopharmacology,* 2006, 186, 587-593). Palucha-Poniewiera et al. *Psychopharmacology,* 2010, 212, 523-535 evaluated a potential antidepressant-like effect of MGS0039 in the olfactory bulbectomy (OB) model of depression in rats. A surgical lesion of the olfactory bulbs in animals is known to induce significant behavioral, physiological, endocrine and immune changes, many of which are qualitatively similar to those observed in depressive patients. Repeated administration of MGS0039 for 14 days attenuated the hyperactivity of olfactory bulbectomized rats in the open field test and attenuated the learning deficit in the passive avoidance test.

Kawasaki et al. *Neuropharmacology,* 2011, 60, 397-404 also examined the effect of MGS0039 on behaviors of social isolation-reared mice in the FST. Rearing rodents in isolation after weaning is known to lead to changes in brain neurochemistry that produce perturbations in behavior. Post-weaning chronic social isolation for more than 6 weeks increased immobility in the FST, suggesting that isolation rearing caused depression-like behavior. MGS0039 reversed the increased immobility of social isolation reared mice in the test.

Campo, B. et al. *J. Neurogenetics* 2011, 25, 152-166, demonstrated a selective group II ($mGlu_2$ and $mGlu_3$) negative allosteric modulator (RO4491533) to be effective in several in vitro biochemical assays and in vivo models of depression. RO4491533 was shown to engage the central $mGlu_2$ and $mGlu_3$ receptors as the compound reversed the hypolocomotor effect of an $mGlu_{2/3}$ agonist (LY379268) in a target-specific manner. The known group II $mGlu_{2/3}$ antagonist LY341495 achieved the same result. RO4491533 and LY341495 dose-dependently reduced immobility time of C57B16/J mice in the FST. RO4491533 and LY341495 were also active in the tail suspension test in a line of Helpless (H) mice, a putative genetic model of depression.

Blockade of $mGlu_{2/3}$ receptors and ketamine may converge to the same neuronal circuits, which include activation of AMPA receptor and mTOR signaling. Because both AMPA receptor stimulation and subsequent mTOR signaling activation are presumed to be involved in rapid action of ketamine for patients with treatment-resistant depression (TRD), $mGlu_{2/3}$ receptor antagonists could exert the same effects in humans. This assumption is underpinned by several animal studies. First, the $mGlu_{2/3}$ receptor antagonist MGS0039 exhibited antidepressant effects in an animal model (the learned helplessness paradigm) which is refractory to currently prescribed antidepressants (Yoshimizu et al. *Psychopharmacology,* 2006, 186, 587-593). Second, although evidence of rapid onset of action with $mGlu_{2/3}$ receptor antagonists are absent, an AMPA receptor potentiator (AMPA receptor potentiation mediates antidepressant effects of $mGlu_{2/3}$ receptor antagonists) showed faster effects (during the first week of treatment) compared to fluoxetine (after two weeks) in a dominant-submissive test (Knapp et al. *Eur. J. Pharmacol.* 2002, 440, 121-125). Moreover, LY341495 exhibited a potent antidepressant effect in helpless mice following acute administration, while fluoxetine exerted a full antidepressant effect following chronic (21 days) treatment (Campo, B. et al. *J. Neurogenetics* 2011, 25, 152-166; El Yacoubi et al. *PNAS,* 2003, 100, 6227-6232). Therefore, blockade of $mGlu_{2/3}$ receptors may show rapid and potent antidepressant effects in humans.

b. Cognitive Disorders

Woltering et al. *Bioorg. Med. Chem. Lett.* 2010, 20, 6969-74, demonstrated that a negative allosteric modulator of $mGlu_{2/3}$ reversed $mGlu_{2/3}$ agonist or scopolamine-induced working memory deficits in the delayed match to position (DMTP) task in rodents, a measure of working memory. Additionally, Woltering demonstrated a synergistic reversal of scopolamine-induced deficits in DMTP when low doses of a negative allosteric modulator of mGlu$_{2/3}$ were combined with a threshold dose of the acetylcholinesterase inhibitor donezepil. Given the efficacy of donepezil and other acetylcholinesterase inhibitors in the treatment of the cognitive impairments in Alzheimer's disease, negative allosteric modulators of mGlu$_2$ may have efficacy as cognitive enhancers.

c. Obsessive-Compulsive Disorder

Shimazaki, T. et al. *Eur. J. Pharmacol.* 2004, 501, 121-125, demonstrated that MGS0039 induced glutamatergic change in mice, resulting in anti-obsessive-compulsive disorder activity. In these studies, a marble-burying behavioral test was utilized as a model for obsessive-compulsive disorder. The marble-burying behavior test is recognized as a useful model for evaluating the clinical potential of anti-obsessive-compulsive disorder drugs. Specifically, MGS0039 treated mice exhibited reduced marble-burying behavior in a significant and dose dependent manner, while no significant change was observed in spontaneous locomotor activity. In addition, LY341495, another potent antagonist of group II mGlu receptors, was also shown to significantly reduce marble-burying behavior in treated mice.

d. Alzheimer's Disease

Kim, S. H. et al. *Moecular Psychiatry* 2014, 1-8, have assessed the therapeutic potential of chronic pharmacological inhibition of group II mGlu receptors (mGlu$_2$ and mGlu$_3$) with a group II mGlu receptor antagonist in an APP transgenic mouse model that develops impaired learning behavior in relation to accumulation of mutant Aβ oligomers that never form amyloid plaques. Once-daily dosing of the orally bioavailable prodrug, BCI-838, delivered a sufficient brain concentration of its active metabolite BCI-632 to inhibit group II mGlu receptors for 22 hours. Three months of treatment with BCI-838 provided anxiolytic effects, reversed Dutch APP transgene-associated learning and memory impairment, and decreased the levels of monomeric and oAβ peptides in the hippocampus and cortex of the two different AD mouse models. Notably, BCI-838 administration stimulated hippocampal progenitor cell proliferation in both wild-type and Alzheimer's diseased mice for 3 months, which resulted in significantly increased numbers of newborn neurons in the hippocampi of Dutch APP transgenic mice. In addition to treatment, the proneurogenic properties make the compound attractive for potential use in reversing some of the early symptoms of Alzheimer's disease (AD), possibly through reparative effects of the newborn neurons. These findings suggest that chronic pharmacological inhibition of group II mGlu receptors has the potential to be a disease-modifying treatment for AD that targets cognitive/emotional defects and modulates neurogenesis.

Additional studies by Caraci, F. et al *Mol. Pharmacol.* 2011, 79, 618-626, showed that a positive allosteric modulator of mGlu$_2$ (LY566332) amplified Aβ-induced neurodegeneration, but this effect was prevented by the mGlu$_{2/3}$ receptor antagonist, LY341495.

e. Anxiety

Yoshimizu et al. *Psychopharmacology,* 2006, 186, 587-593 also demonstrated the anxiolytic effects of MGS0039, a potent antagonist of group II mGlu receptors (mGlu$_2$ and mGlu$_3$), by use of a conditioned fear stress (CFS) model, which represents emotional abnormality, including anxiety. The CFS model reflects psychological stress without physical stimuli, and is useful in predicting the clinical efficacy of anxiolytic drugs. In these studies, MGS0039 significantly decreased freezing behavior, as did diazepam and fluvoxamine, indicating the anxiolytic-like potential of MGS0039. The mGlu$_{23}$ receptors inhibit neurotransmitter release as autoreceptors located on glutamatergic terminals and treatment with mGlu$_{2/3}$ antagonists such as MGS0039 in vivo led to an increase in extracellular glutamate. Therefore, the moderate elevation of glutamate levels in specific areas of the brain by MGS0039 may cause the anxiolytic-like effects seen in the CFS model. These results suggest that the blockade of mGlu$_{2/3}$ with MGS0039 may be effective in the treatment of anxiety disorders.

f. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, crosslinking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

g. Combination Therapies

Additional therapeutic agent(s) may be administered simultaneously or sequentially with the disclosed compounds and compositions. Sequential administration includes administration before or after the disclosed compounds and compositions. In some embodiments, the additional therapeutic agent or agents may be administered in the same composition as the disclosed compounds. In other embodiments, there may be an interval of time between administration of the additional therapeutic agent and the disclosed compounds. In some embodiments, administration of an additional therapeutic agent with a disclosed compound may allow lower doses of the other therapeutic agents and/or administration at less frequent intervals. When used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula (I). The above combinations include combinations of a compound of the present invention not only with one other active compound, but also with two or more other active compounds. For example, the compound of Formula (I) can be combined with a variety of antidepressants, Alzheimer's disease medications, and anxiolytics.

The compound of Formula (I) can be combined with the following antidepressants, but not limited to: Selective serotonin reuptake inhibitors (SSRIs) such as citalopram, dapoxetine, escitalopram, fluoxetine, fluvoxamine, indalpine, paroxetine, sertraline, and zimelidine; Serotonin-norepinephrine reuptake inhibitors (SNRIs) such as venlafaxine, desvenlafaxine, duloxetine, milnacipran, levomilnacipran, and sibutramine; Noradrenergic and specific serotonergic antidepressants (NaSSAs) or tetracyclic antidepressants (TeCAs) such as aptazapine, esmirtazapine, mianserin, mirtazapine, and setiptiline; Serotonin antagonist and reuptake inhibitors (SARIs) such as etoperidone, lorpiprazole, mepiprazole, nefazodone, trazodone, vilazodone, and niaprazine; Norepinephrine-dopamine reuptake inhibitors (NDRIs) such as armodafinil, bupropion, desoxypipradrol, dexmethylphenidate, methylphenidate, modafinil, prolintane, and tametraline; Serotonin-norepinephrine-dopamine reuptake inhibitors (SNDRIs) such as nefopam, amitifadine, tesofensine, and tedatioxetine; Tricyclic antidepressants (TCAs) such as clomipramine, desipramine, imipramine, dibenzepin, lofepramine, nortriptyline, protriptyline, amitriptyline, amitriptylinoxide, amoxapine, butriptyline, demexiptiline, dimetacrine, dosulepin, doxepin, imipraminoxide, melitracen, metapramine, nitroxazepine, noxiptiline, pipofezine, propizepine, quinupramine, amineptine, iprindole, opipramol, tianeptine, and trimipramine; and Negative allosteric modulators of metabotropic glutamate receptor 5 (mGlus) such as mavoglurant, basimglurant, dipraglurant, STX107, and N-(5-fluoropyridin-2-yl)-6-methyl-4-(pyrimidin-5-yloxy)picolinamide.

The compound of Formula (I) can be combined with the following Alzheimer's disease medications, but not limited to: Acetylcholinesterase inhibitors such as tacrine, rivastigmine, galantamine, donepezil, edrophonium, physostigmine, pyridostigmine, ambenonium, rivastigmine, ladostigil, and ungeremine; and NMDA receptor antagonists such as memantine, amantadine, delucemine, and ketamine.

The compound of Formula (I) can be combined with the following anxiolytics, but not limited to: buspirone, tandospirone, gepirone, adaptol, afobazole, hyroxyzine, validol, melatonin, and benzodiazepines such as alprazolam, chlordiazepoxide, clonazepam, diazepam, etizolam, lorazepam, oxazepam, and tofisopam.

The disclosed compounds may be included in kits comprising the compound [e.g., one or more compounds of formula (I)], a systemic or topical composition described above, or both; and information, instructions, or both that use of the kit will provide treatment for medical conditions in mammals (particularly humans). The information and instructions may be in the form of words, pictures, or both, and the like. In addition or in the alternative, the kit may include the medicament, a composition, or both; and information, instructions, or both, regarding methods of application of medicament, or of composition, preferably with the benefit of treating or preventing medical conditions in mammals (e.g., humans).

The compounds and processes of the invention will be better understood by reference to the following examples, which are intended as an illustration of and not a limitation upon the scope of the invention.

6. Examples

Examples 1-12 below give representative experimental procedures for the syntheses of intermediates useful for the synthesis of compounds of formula (I). Examples 13-18 give representative experimental procedures for completion of the syntheses of compounds of formula (I). Example 19 reports the biological activity of compounds of formula (I).

All NMR spectra were recorded on a 400 MHz AMX Bruker NMR spectrometer. $^1$H chemical shifts are reported in δ values in ppm downfield with the deuterated solvent as the internal standard. Data are reported as follows: chemical shift, multiplicity (s=singlet, bs=broad singlet, d=doublet, t=triplet, q=quartet, dd=doublet of doublets, m=multiplet, ABq=AB quartet), coupling constant, integration. Reversed-phase LCMS analysis was performed using an Agilent 1200 system comprised of a binary pump with degasser, high-performance autosampler, thermostatted column compartment, C18 column, diode-array detector (DAD) and an Agilent 6150 MSD with the following parameters. The gradient conditions were 5% to 95% acetonitrile with the aqueous phase 0.1% TFA in water over 1.4 minutes. Samples were separated on a Waters Acquity UPLC BEH C18 column (1.7 μm, 1.0×50 mm) at 0.5 mL/min, with column and solvent temperatures maintained at 55° C. The DAD was set to scan from 190 to 300 nm, and the signals used were 220 nm and 254 nm (both with a band width of 4 nm). The MS detector was configured with an electrospray ionization source, and the low-resolution mass spectra were acquired by scanning from 140 to 700 AMU with a step size of 0.2 AMU at 0.13 cycles/second, and peak width of 0.008 minutes. The drying gas flow was set to 13 liters per minute at 300° C. and the nebulizer pressure was set to 30 psi. The capillary needle voltage was set at 3000 V, and the fragmentor voltage was set at 100V. Data acquisition was performed with Agilent Chemstation and Analytical Studio Reviewer software.

Example 1

Ethyl 6-bromo-1-(4-fluorophenyl)-4-oxo-1,4-dihydroquinoline-3-carboxylate (D)

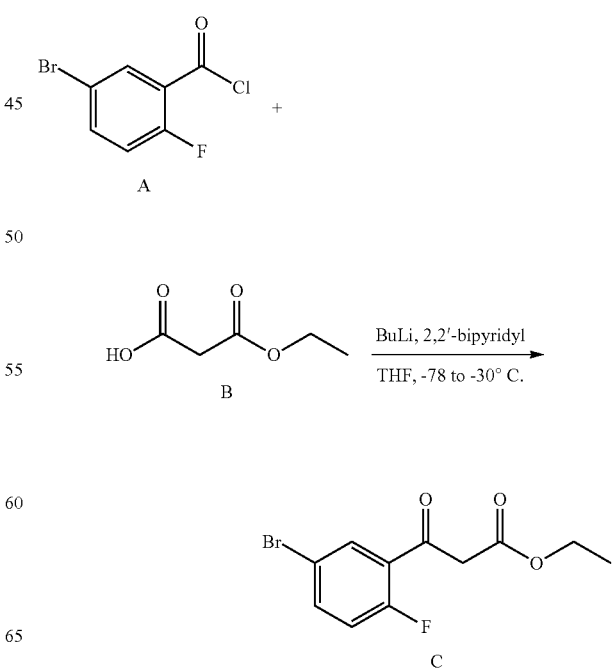

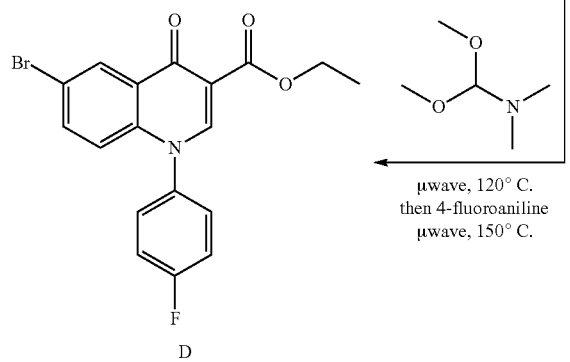

Ethyl 3-(5-bromo-2-fluorophenyl)-3-oxopropanoate (C)

3-Ethoxy-3-oxopropanoic acid (B) (2.16 mL, 18.3 mmol, 2.00 eq) was dissolved in THF (91 mL) in an oven dried round-bottom flask and 2,2'-bipyridyl (8.00 mg, 0.0512 mmol, 0.0056 eq) was added as an indicator. The reaction was cooled to −30° C. and n-butyllithium (1.6 M in hexanes) (29.0 mL, 45.6 mmol, 4.00 eq) was added dropwise over 20 minutes. Upon final addition the reaction turned red at which point it was allowed to warm to −5° C. The reaction was allowed to stir at −5° C. for 15 minutes, during which time the red color began to dissipate. Enough n-butyllithium was added to cause the red color to persist. The reaction was then cooled to −78° C. and 5-bromo-2-fluoro-benzoyl chloride (A) (2.17 g, 9.14 mmol, 1.00 eq) was added dropwise as a solution in THF (6.9 mL). The reaction was allowed to stir at −78° C. for 30 minutes and then allowed to warm to −30° C. and stirred for an additional 30 minutes. The reaction was poured onto ice-cold 1N HCl (92 mL) and the mixture was extracted with ethyl acetate (1x) and DCM (2x). The combined organics were dried (MgSO$_4$), filtered and concentrated in vacuo. Purification by flash chromatography on silica gel using 0-10% hexanes/ethyl acetate afforded 1.78 g (67%) of the title compound as an off-white solid. $^1$H NMR (400 MHz, DMSO-d$_6$) δ 7.97 (dd, J=6.5, 2.6 Hz, 1H), 7.91-7.86 (m, 1H), 7.40-7.34 (m, 1H), 4.13-4.07 (m, 4H), 1.15 (t, J=7.1 Hz, 3H); ES-MS [M+1]$^+$: 289.0.

Ethyl 6-bromo-1-(4-fluorophenyl)-4-oxo-1,4-dihydroquinoline-3-carboxylate (D)

Compound C (2.87 g, 9.93 mmol, 1.00 eq) and N,N-dimethylformamide dimethyl acetal (1.87 mL, 14.9 mmol, 1.50 eq) were dissolved in DMF (33 mL) in a microwave vial and heated in a microwave reactor at 120° C. for 15 minutes. To this mixture was then added 4-fluoroaniline (1.41 mL, 14.9 mmol, 1.50 eq) and the reaction was heated in a microwave reactor at 150° C. for 20 minutes. The reaction mixture was diluted with ethyl acetate and washed with water (2x). The aqueous layers were back-extracted with ethyl acetate and the combined organics were dried (MgSO$_4$), filtered and concentrated in vacuo. Purification by flash chromatography on silica gel using 0-45% hexanes/ethyl acetate afforded 3.79 g (98%) of the title compound as yellow solid. $^1$H NMR (400 MHz, DMSO-d$_6$) δ 8.47 (s, 1H), 8.31 (d, J=2.4 Hz, 1H), 7.81 (dd, J=9.1, 2.4 Hz, 1H), 7.77-7.73 (m, 2H), 7.54-7.50 (m, 2H), 6.92 (d, J=9.0 Hz, 1H), 4.20 (q, J=7.1 Hz, 2H), 1.25 (t, J=7.1 Hz, 3H); ES-MS [M+1]$^+$: 390.2.

Example 2
6-Bromo-1-(4-fluorophenyl)-4-oxo-1,4-dihydroquinoline-3-carboxamide (E)

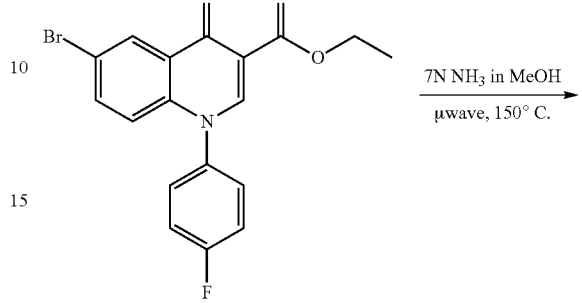

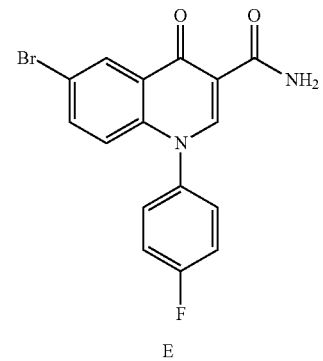

6-Bromo-1-(4-fluorophenyl)-4-oxo-1,4-dihydroquinoline-3-carboxamide (E)

Compound D (1.00 g, 2.56 mmol, 1.00 eq) was suspended in 7N ammonia in methanol (30 mL) in a microwave vial and the reaction was heated in a microwave reactor at 150° C. for 60 minutes. The reaction was concentrated to afford 881 mg (95%) of the title compound as a brown solid that was used without further purification. $^1$H NMR (400 MHz, DMSO-d$_6$) δ 9.08 (d, J=4.0 Hz, 1H), 8.57 (s, 1H), 8.43 (d, J=2.4 Hz, 1H), 7.85 (dd, J=9.1, 2.4 Hz, 1H), 7.77-7.73 (m, 2H), 7.66 (d, J=4.1 Hz, 1H), 7.56-7.50 (m, 2H), 7.02 (d, J=9.1 Hz, 1H); ES-MS [M+1]$^+$: 361.2.

Example 3
1-(4-Fluorophenyl)-6-formyl-4-oxo-1,4-dihydroquinoline-3-carboxamide (G)

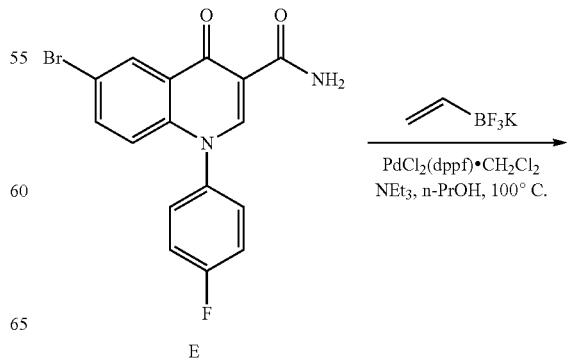

-continued

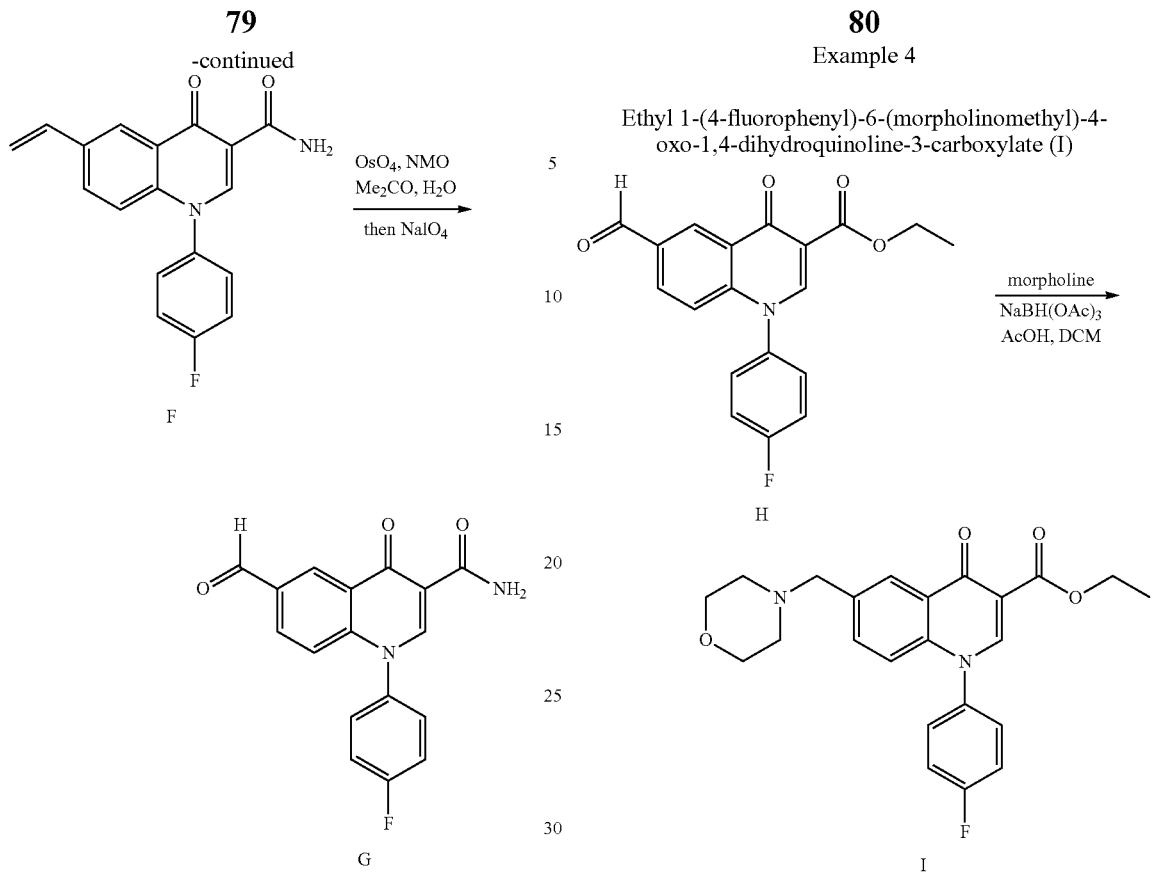

Example 4

Ethyl 1-(4-fluorophenyl)-6-(morpholinomethyl)-4-oxo-1,4-dihydroquinoline-3-carboxylate (I)

1-(4-Fluorophenyl)-4-oxo-6-vinyl-1,4-dihydroquinoline-3-carboxamide (F)

To a solution of compound E (450 mg, 1.25 mmol), triethylamine (174 µL, 1.25 mmol), and Pd(dppf)Cl$_2$ CH$_2$Cl$_2$ (18.2 mg, 0.025 mmol) in 1-propanol (8.3 mL) was added potassium vinyltrifluoroborate (200 mg, 1.50 mmol). The reaction was purged with argon and stirred at 100° C. for 16 hours. The reaction was filtered over Celite® and washed very well with a 5% MeOH in DCM solution and concentrated in vacuo to give 385 mg (100%) of the title compound that was used without further purification. ES-MS [M+1]$^+$: 309.2.

1-(4-Fluorophenyl)-6-formyl-4-oxo-1,4-dihydroquinoline-3-carboxamide (G)

To a solution of compound F (385 mg, 1.25 mmol) in 3:1 acetone/water (8 mL) was added N-oxide-4-methylmorpholine (220 mg, 1.87 mmol) and osmium tetroxide (254 µL, 0.025 mmol). After the reaction stirred for one hour, sodium periodate (294 mg, 1.37 mmol) was added. After another two hours, the reaction was diluted with EtOAc and washed well with a 10% NaS$_2$O$_3$ solution. The organic layer was dried (MgSO4), filtered and concentrated in vacuo to give 365 mg (94%) of the title compound that was used without further purification. ES-MS [M+1]$^+$: 311.2.

Ethyl 1-(4-fluorophenyl)-6-(morpholinomethyl)-4-oxo-1,4-dihydroquinoline-3-carboxylate (I)

Ethyl 1-(4-fluorophenyl)-6-formyl-4-oxo-1,4-dihydroquinoline-3-carboxylate (H) was prepared from compound D via a method analogous to that described in Example 3. After stirring for two hours, a solution of compound H (10 mg, 0.030 mmol), morpholine (3.1 µL, 0.035 mmol), and acetic acid (4.2 µL, 0.074 mmol) in dichloromethane (1 mL) was treated with sodium triacetoxyborohydride (9.4 mg, 0.044 mmol). After stirring 16 hours, the reaction was concentrated to dryness to give 12 mg (99%) of the title compound that was used without further purification. ES-MS [M+1]$^+$: 411.3.

Example 5

Ethyl 1-(4-fluorophenyl)-6-(hydroxymethyl)-4-oxo-1,4-dihydroquinoline-3-carboxylate (J)

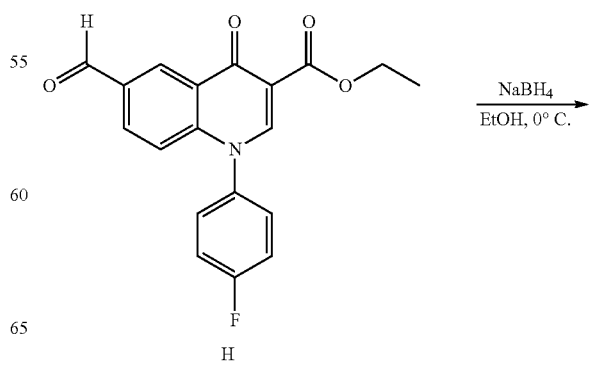

-continued

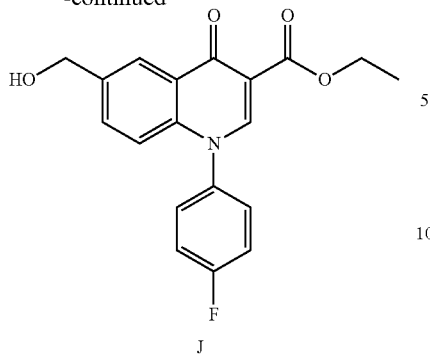

J

-continued

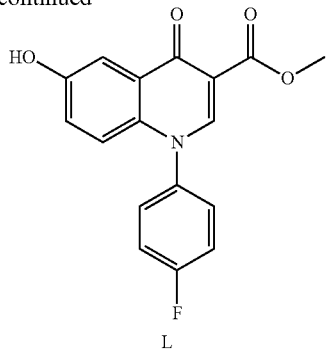

L

Ethyl 1-(4-fluorophenyl)-6-(hydroxymethyl)-4-oxo-1,4-dihydroquinoline-3-carboxylate (J):

To compound H (335 mg, 0.99 mmol) in ethanol (5 mL) cooled to 0° C. was added sodium borohydride (18.7 mg, 0.49 mmol). After ten minutes, the reaction was diluted with EtOAc and washed well with water. The organic layer was dried (MgSO$_4$), filtered and concentrated in vacuo. Purification by flash chromatography on silica gel afforded 192 mg (57%) of the title compound. $^1$H NMR (400 MHz, DMSO-d$_6$) δ 8.44 (s, 1H), 8.25 (s, 1H), 7.76-7.72 (m, 2H), 7.61 (d, J=6 Hz, 1H), 7.54 (t, J=8.64, 8.68 Hz, 2H), 6.94 (d, J=8.68, 1H), 5.42 (t, J=5.68, 5.64 Hz, 1H), 4.62 (d, J=5.48 Hz, 2H), 4.23 (q, J=7.08 Hz, 2H), 1.27 (t, J=7.12, 7.04 Hz, 3H); ES-MS [M+1]$^+$: 342.3.

Example 6

Methyl 1-(4-fluorophenyl)-6-hydroxy-4-oxo-1,4-dihydroquinoline-3-carboxylate (L)

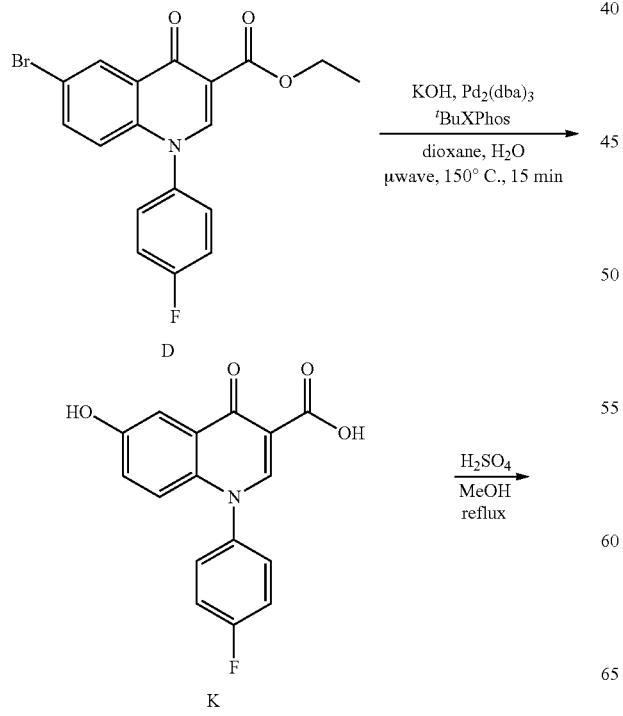

1-(4-Fluorophenyl)-6-hydroxy-4-oxo-1,4-dihydroquinoline-3-carboxylic acid (K)

Compound D (500 mg, 1.28 mmol, 1.00 eq), potassium hydroxide (216 mg, 3.84 mmol, 3.00 eq), tris(dibenzylideneacetone)dipalladium(0) (70.4 mg, 0.0769 mmol, 0.0600 eq) and 2-di-tert-butylphosphino-2',4',6'-triisopropylbiphenyl (65.3 mg, 0.154 mmol, 0.120 eq) were suspended in a mixture of 1,4-dioxane (3.2 mL) and water (3.2 mL) in a microwave vial and heated in a microwave reactor at 150° C. for 15 minutes. The reaction was neutralized with 2N HCl and the mixture was diluted with ethyl acetate and washed with water. The organic phase was dried (MgSO4), filtered and concentrated in vacuo to afford 383 mg (99%) of the title compound as a brown solid that was used without further purification. $^1$H NMR (400 MHz, DMSO-d6) δ 8.56 (s, 1H), 7.75-7.72 (m, 2H), 7.67 (d, J=2.7 Hz, 1H), 7.51 (t, J=8.7 Hz, 2H), 7.26 (d, J=9.1 Hz, 1H), 6.99 (d, J=9.2 Hz, 1H); ES-MS [M+1]$^+$: 300.2.

Methyl 1-(4-fluorophenyl)-6-hydroxy-4-oxo-1,4-dihydroquinoline-3-carboxylate (L)

Compound K (383 mg, 1.28 mmol, 1.00 eq) was dissolved in methanol (6.4 mL) and concentrated sulfuric acid (0.64 mL) was added dropwise. The reaction was heated to reflux for 3 hours at which point it was cooled and neutralized with a saturated solution of sodium bicarbonate. The mixture was extracted with a solution of 3:1 CHCl$_3$:IPA (2×) and the combined organics were dried (MgSO$_4$), filtered and concentrated in vacuo. Purification by flash chromatography on silica gel using 0-20% 89:10:1 DCM:methanol:NH$_{4O}$H afforded 296 mg (74%) of the title compound as yellow solid. $^1$H NMR (400 MHz, DMSO-d$_6$) δ 10.03 (s, 1H), 8.36 (s, 1H), 7.72-7.68 (m, 2H), 7.61 (d, J=2.8 Hz, 1H), 7.49 (t, J=8.7 Hz, 2H), 7.11 (dd, J=9.0, 2.8 Hz, 1H), 6.84 (d, J=9.1 Hz, 1H), 3.71 (s, 3H); ES-MS [M+1]$^+$: 314.2.

Example 7

Methyl 1-(4-fluorophenyl)-4-oxo-6-(pyridin-3-yl-methoxy)-1,4-dihydroquinoline-3-carboxylate (M)

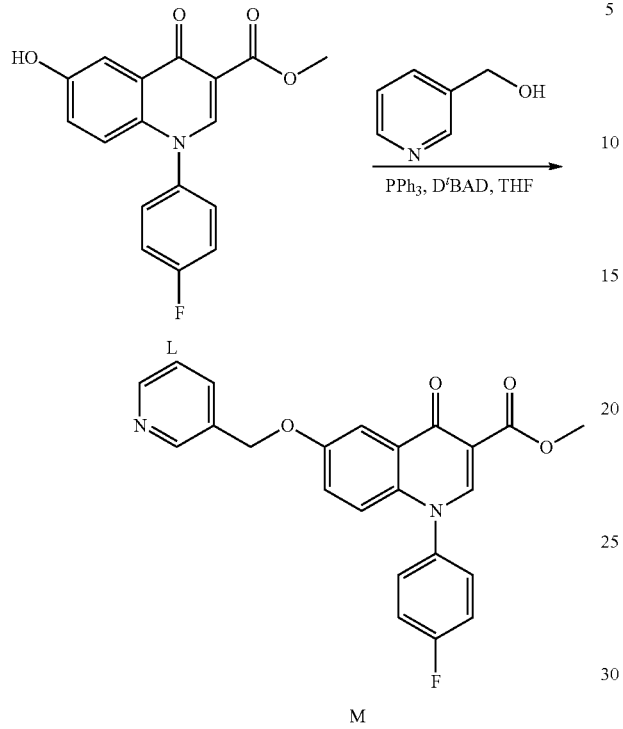

Methyl 1-(4-fluorophenyl)-4-oxo-6-(pyridin-3-yl-methoxy)-1,4-dihydroquinoline-3-carboxylate (M)

Compound L (15 mg, 0.048 mmol, 1.0 eq) and 3-pyridinemethanol (10 mg, 0.096 mmol, 2.0 eq) were dissolved in THF (0.5 mL) and cooled to 0° C. Triphenylphosphine (28 mg, 0.11 mmol, 2.2 eq) and di-tert-butylazodicarboxylate (18 mg, 0.077 mmol, 1.6 eq) were added and the reaction was stirred at room temperature until complete by LCMS. The reaction was concentrated and purified using reverse phase chromatography to afford 15 mg (77%) of the title compound as a white solid. $^1$H NMR (400 MHz, DMSO-$d_6$) δ 8.69 (d, J=1.7 Hz, 1H), 8.54 (dd, J=4.7, 1.3 Hz, 1H), 8.41 (s, 1H), 7.90-7.88 (m, 1H), 7.79 (d, J=3.0 Hz, 1H), 7.73-7.70 (m, 2H), 7.50 (t, J=8.8 Hz, 2H), 7.43 (dd, J=7.8, 4.8 Hz, 1H), 7.37 (dd, J=9.3, 3.0 Hz, 1H) 6.94 (d, J=9.2 Hz, 1H), 5.28 (s, 2H), 3.72 (s, 3H); ES-MS [M+1]$^+$: 405.2.

Example 8

Ethyl 1-(4-fluorophenyl)-6-(((2-methylpyrimidin-5-yl)oxy)methyl)-4-oxo-1,4-dihydroquinoline-3-carboxylate (N)

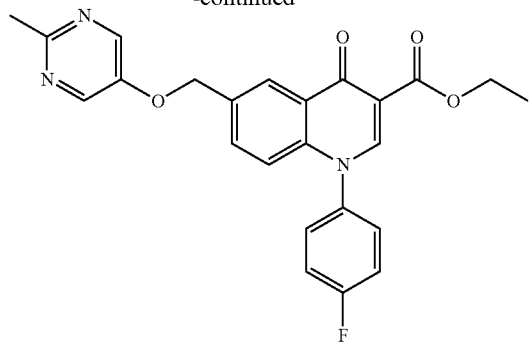

Ethyl 1-(4-fluorophenyl)-6-(((2-methylpyrimidin-5-yl)oxy)methyl)-4-oxo-1,4-dihydroquinoline-3-carboxylate (N)

To a solution of compound J (16 mg, 0.047 mmol) and 5-hydroxy-2-methylpyrimidine (6.2 mg, 0.056 mmol) in THF (1 mL) cooled to 0° C. was added triphenylphosphine (27.1 mg, 0.10 mmol) and di-tert-butylazodicarboxylate (17.3 mg, 0.075 mmol). The reaction was concentrated to dryness after 16 hours of stirring. Purification by reverse phase HPLC afforded 20 mg (98%) of the title compound. ES-MS [M+1]$^+$: 434.3.

Example 9

Ethyl 1-(4-fluorophenyl)-6-(methyl(pyridin-3-ylmethyl)amino)-4-oxo-1,4-dihydroquinoline-3-carboxylate (O)

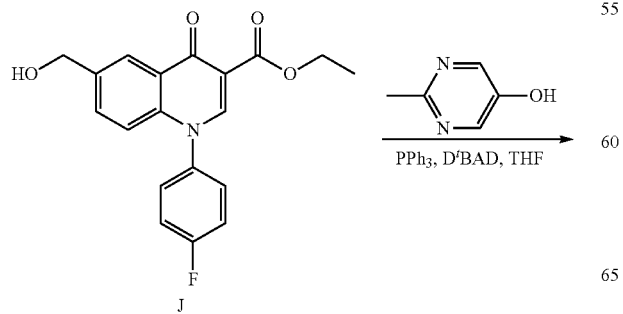

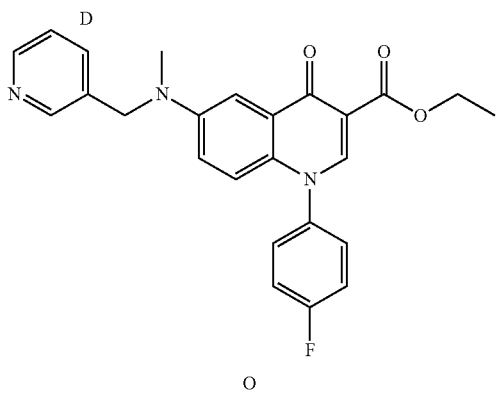

Ethyl 1-(4-fluorophenyl)-6-(methyl(pyridin-3-ylmethyl)amino)-4-oxo-1,4-dihydroquinoline-3-carboxylate (O)

Compound D (75 mg, 0.19 mmol, 1.0 eq), N-methyl-N-(3-pyridylmethyl)amine (47 mg, 0.38 mmol, 2.0 eq), cesium carbonate (88 mg, 0.27 mmol, 1.4 eq), tris(dibenzylideneacetone)dipalladium(0) (14 mg, 0.015 mmol, 0.080 eq) and 4,5-bis(diphenylphosphino)-9,9-dimethylxanthene (13 mg, 0.023 mmol, 0.12 eq) were dissolved in toluene (1.9 mL) in a sealed vial and heated at 110° C. overnight. The reaction was cooled, filtered over Celite® and washed with 5% methanol in DCM. The organics were concentrated and purified using reverse phase chromatography to afford 27 mg (33%) of the title compound as a yellow solid. $^1$H NMR (400 MHz, DMSO-$d_6$) δ 8.44 (s, 2H), 8.28 (s, 1H), 7.68 (dd, J=6.9, 4.9 Hz, 2H), 7.58 (d, J=7.8 Hz, 1H), 7.47 (t, J=8.7 Hz, 2H), 7.40 (d, J=3.0 Hz, 1H), 7.34-7.30 (m, 1H), 7.21 (dd, J=9.3, 3.0 Hz, 1H), 6.80 (d, J=9.3 Hz, 1H), 4.70 (s, 2H), 4.17 (q, J=7.1 Hz, 2H), 3.12 (s, 3H), 1.23 (t, J=7.1 Hz, 3H); ES-MS [M+1]$^+$: 432.3.

Example 10

Ethyl 1-(4-fluorophenyl)-6-((2-methylpyrimidin-5-yl)ethynyl)-4-oxo-1,4-dihydroquinoline-3-carboxylate (P)

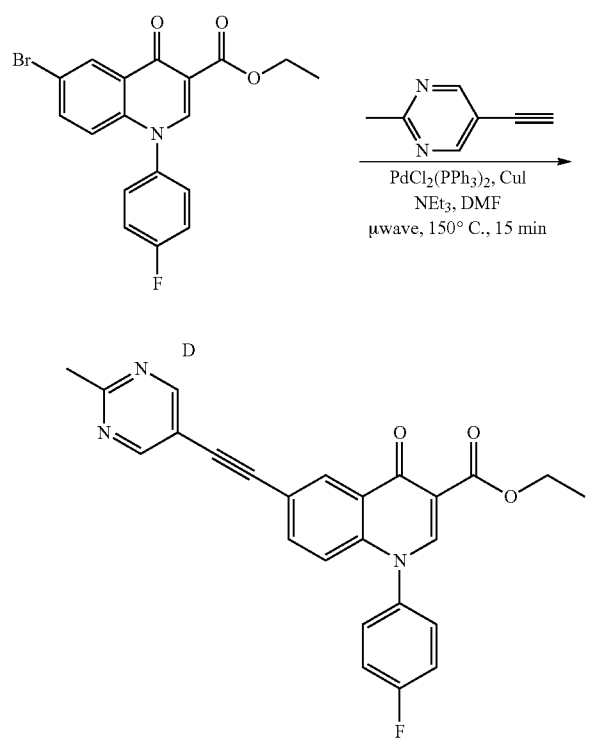

Ethyl 1-(4-fluorophenyl)-6-((2-methylpyrimidin-5-yl)ethynyl)-4-oxo-1,4-dihydroquinoline-3-carboxylate (P)

Compound D (50 mg, 0.13 mmol, 1.0 eq), 5-ethynyl-2-methyl-pyrimidine (30 mg, 0.26 mmol, 2.0 eq), copper(I) iodide (2.5 mg, 0.013 mmol, 0.010 eq), bis(triphenylphosphine)palladium(II) dichloride (4.5 mg, 0.0064 mmol, 0.050 eq) and triethylamine (53.6 µL, 0.38 mmol, 3.0 eq) were dissolved in DMF (1.3 mL) in a microwave vial and heated in a microwave reactor at 150° C. for 15 minutes. The reaction was purified directly using reverse phase chromatography to afford 30 mg (55%) of the title compound as white solid. $^1$H NMR (400 MHz, DMSO-$d_6$) δ 8.93 (s, 2H), 8.47 (s, 1H), 8.40 (d, J=2.0 Hz, 1H), 7.81-7.76 (m, 3H), 7.53 (t, J=8.7 Hz, 2H), 7.02 (d, J=8.80 Hz, 1H), 4.21 (q, J=7.1 Hz, 2H), 2.66 (s, 3H), 1.25 (t, J=7.1 Hz, 3H); ES-MS [M+1]$^+$: 428.2.

Example 11

Ethyl 1-(4-fluorophenyl)-4-oxo-6-((2-(trifluoromethyl)pyridin-4-yl)ethynyl)-1,4-dihydroquinoline-3-carboxylate (S)

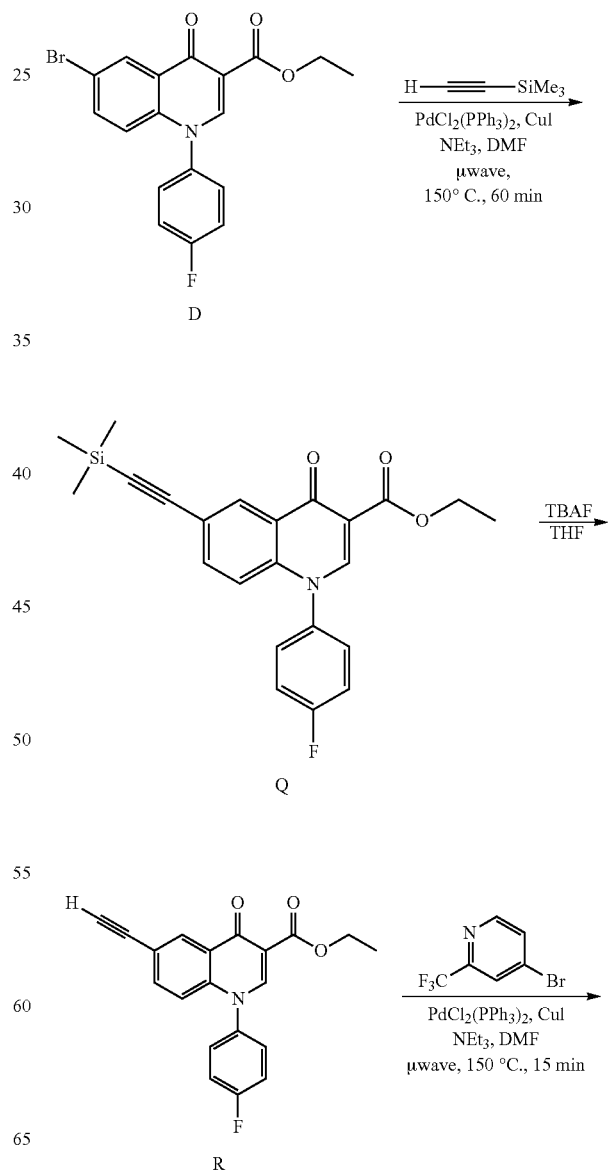

-continued

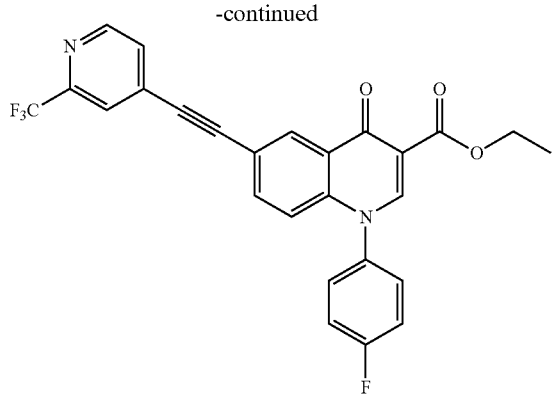

S

Ethyl 1-(4-fluorophenyl)-4-oxo-6-((trimethylsilyl)ethynyl)-1,4-dihydroquinoline-3-carboxylate (Q)

Compound D (450 mg, 1.15 mmol), trimethylsilylacetylene (179 μL, 1.27 mmol), PdCl$_2$(PPh$_3$)$_2$ (40.5 mg, 0.058 mmol), CuI (22 mg, 0.12 mmol), triethylamine (321 μL, 2.31 mmol) and DMF (5.8 mL) were added to a microwave vial. The vial was capped and place in a microwave reactor at 150° C. for one hour. The reaction was washed with water and brine and extracted with EtOAc (2×). The organics were combined, dried (MgSO$_4$), and concentrated to dryness. Purification by flash chromatography on silica gel afforded 205 mg (44%) of the title compound. $^1$H NMR (400 MHz, DMSO-d$_6$) δ 8.45 (s, 1H), 8.24 (d, J=1.84 Hz, 1H), 7.76-7.73 (m, 2H), 7.68 (dd, J=8.8 Hz, 1H), 7.52 (t, J=8.64, 8.72 Hz, 2H), 6.93 (d, J=8.8 Hz, 1H), 4.22 (q, J=7.08 Hz, 2H), 1.25 (t, J=7.12, 7.04 Hz, 3H), 0.24 (s, 9H); ES-MS [M+1]$^+$: 408.2.

Ethyl 6-ethynyl-1-(4-fluorophenyl)-4-oxo-1,4-dihydroquinoline-3-carboxylate (R)

To a solution of Compound Q (205 mg, 0.5 mmol) in THF (2.5 mL) was added a 1M solution of TBAF in THF (554 μL, 0.55 mmol). After thirty minutes the reaction was concentrated in vacuo. Purification by flash chromatography on silica gel afforded 110 mg (65%) of the title compound. $^1$H NMR (400 MHz, DMSO-d$_6$) δ 8.47 (s, 1H), 8.28 (d, J=1.84 Hz, 1H), 7.77-7.69 (m, 3H), 7.54-7.5 (m, 2H), 6.67 (d, J=8.8 Hz, 1H), 4.22-4.19 (m, 3H), 1.28-1.23 (m, 3H); ES-MS [M+1]$^+$: 336.3.

Ethyl 1-(4-fluorophenyl)-4-oxo-6-((2-(trifluoromethyl)pyridin-4-yl)ethynyl)-1,4-dihydroquinoline-3-carboxylate (S)

Compound R (20 mg, 0.06 mmol), 4-bromo-2-(trifluoromethyl)pyridine (16.2 mg, 0.07 mmol), CuI (1.1 mg, 0.006 mmol), triethylamine (25 μL, 0.18 mmol), PdCl$_2$(PPh$_3$)$_2$ (2.7 mg, 0.003 mmol), and DMF (600 μL) were added to a small microwave vial. The vial was capped and placed in microwave reactor at 150° C. for fifteen minutes. The reaction was filtered over Celite®, washed very well with a 5% MeOH in DCM solution and concentrated to dryness. Purification by reverse phase HPLC afforded 13 mg (45%) of the title compound. $^1$H NMR (400 MHz, DMSO-d$_6$) δ 8.84 (d, J=4.96 Hz, 1H), 8.52-8.5 (m, 2H), 8.17 (s, 1H), 7.93 (d, J=5.04 Hz, 1H), 7.87 (dd, J=8.8 Hz, 1H), 7.81-7.77 (m, 2H), 7.55 (t, J=8.64, 8.68 Hz, 2H), 7.07 (d, J=8.8 Hz, 1H), 4.24 (q, J=7.04, 7.08 Hz, 2H), 1.28 (t, J=7.12, 7.08 Hz, 3H); ES-MS [M+1]$^+$: 481.2.

Example 12

Ethyl 1-(4-fluorophenyl)-6-(2-(2-methylpyrimidin-5-yl)ethyl)-4-oxo-1,4-dihydroquinoline-3-carboxylate (T)

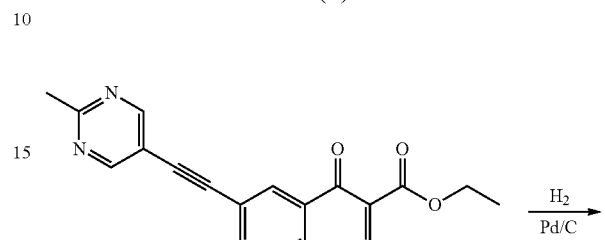

P

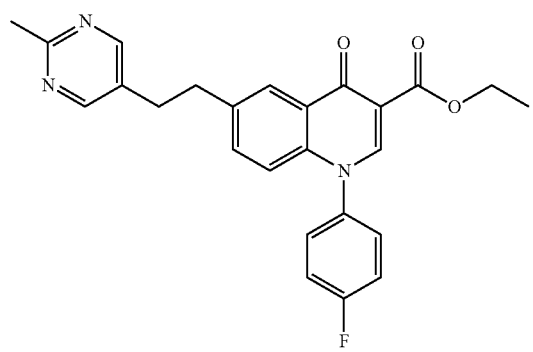

T

Ethyl 1-(4-fluorophenyl)-6-(2-(2-methylpyrimidin-5-yl)ethyl)-4-oxo-1,4-dihydroquinoline-3-carboxylate (T)

Compound P (25 mg, 0.059 mmol, 1.0 eq) was dissolved in methanol (2 mL) and palladium on carbon (1 mg) was added. The reaction was pumped and purged with hydrogen and allowed to stir overnight. The reaction was filtered over Celite® and washed with 5% methanol in DCM. The organics were concentrated and purified using reverse phase chromatography to afford 16 mg (63%) of title compound as a white solid. $^1$H NMR (400 MHz, DMSO-d$_6$) δ 8.54 (s, 2H), 8.41 (s, 1H), 8.09 (d, J=2.0 Hz, 1H), 7.74-7.71 (m, 2H), 7.55 (dd, J=8.7, 2.1 Hz, 1H), 7.50 (t, J=8.8 Hz, 2H), 6.89 (d, J=8.7 Hz, 1H), 4.20 (q, J=7.1 Hz, 2H), 3.04 (t, J=8.3 Hz, 2H), 2.89 (t, J=8.3 Hz, 2H), 2.53 (s, 3H), 1.24 (t, J=7.1 Hz, 3H); ES-MS [M+1]$^+$: 432.3.

Example 13

1-(4-Fluorophenyl)-6-(2-(2-methylpyrimidin-5-yl)ethyl)-4-oxo-1,4-dihydroquinoline-3-carboxamide (1)

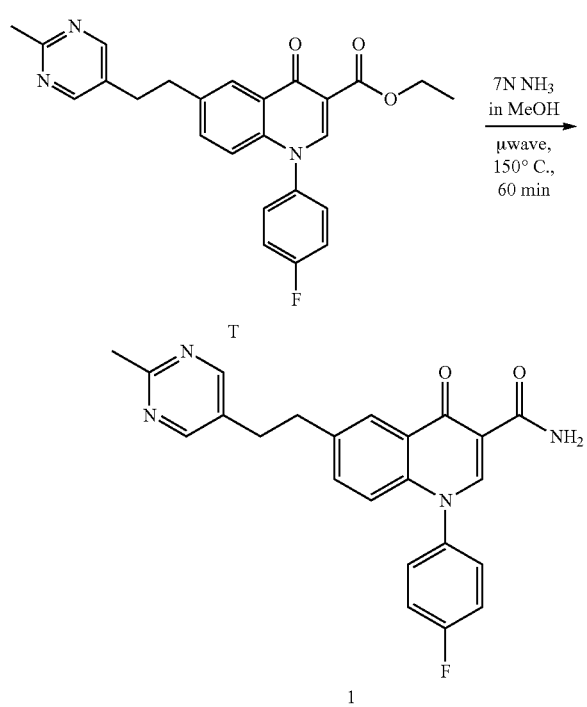

1-(4-Fluorophenyl)-6-(2-(2-methylpyrimidin-5-yl)ethyl)-4-oxo-1,4-dihydroquinoline-3-carboxamide (1)

Compound T (11 mg, 0.026 mmol, 1.0 eq) was dissolved in 7N ammonia in methanol (1 mL) in a microwave vial and heated in a microwave reactor at 150° C. for 60 minutes. The reaction was concentrated and purified by reverse phase chromatography to afford 6.7 mg (65%) of the title compound as a white solid. $^1$H NMR (400 MHz, DMSO-$d_6$) δ 9.24 (d, J=4.4 Hz, 1H), 8.55 (s, 2H), 8.53 (s, 1H), 8.20 (d, J=2.0 Hz, 1H), 7.76-7.71 (m, 2H), 7.62-7.58 (m, 2H), 7.51 (t, J=8.7 Hz, 2H), 6.99 (d, J=8.7 Hz, 1H), 3.06 (t, J=8.3 Hz, 2H), 2.90 (t, J=8.3 Hz, 2H), 2.53 (s, 3H); ES-MS [M+1]$^+$: 403.2.

The following compounds were prepared in an analogous manner by first preparing the appropriate synthetic intermediate by use of the synthetic procedures indicated next to each compound:

| No. | Name | Examples used to prepare intermediate compound | ES-MS [H + 1]$^+$ |
|---|---|---|---|
| 2 | 1-(4-fluorophenyl)-4-oxo-6-(thiomorpholinomethyl)-1,4-dihydroquinoline-3-carboxamide | 1, 3, 4 | 398.4 |
| 3 | 1-(4-fluorophenyl)-6-(morpholinomethyl)-4-oxo-1,4-dihydroquinoline-3-carboxamide | 1, 3, 4 | 382.2 |
| 4 | 1-(4-fluorophenyl)-4-oxo-6-(piperidin-1-ylmethyl)-1,4-dihydroquinoline-3-carboxamide | 1, 3, 4 | 380.4 |
| 5 | 1-(4-fluorophenyl)-4-oxo-6-phenethyl-1,4-dihydroquinoline-3-carboxamide | 1, 10, 12 | 387.2 |
| 6 | 1-(4-fluorophenyl)-6-(4-methylphenethyl)-4-oxo-1,4-dihydroquinoline-3-carboxamide | 1, 10, 12 | 401.2 |
| 7 | 1-(4-fluorophenyl)-6-(3-methylphenethyl)-4-oxo-1,4-dihydroquinoline-3-carboxamide | 1, 10, 12 | 401.3 |
| 8 | 1-(4-fluorophenyl)-6-(2-methylphenethyl)-4-oxo-1,4-dihydroquinoline-3-carboxamide | 1, 10, 12 | 401.3 |
| 9 | 1-(4-fluorophenyl)-4-oxo-6-(2-(pyridin-4-yl)ethyl)-1,4-dihydroquinoline-3-carboxamide | 1, 10, 12 | 388.2 |
| 10 | 1-(4-fluorophenyl)-4-oxo-6-(2-(pyridin-3-yl)ethyl)-1,4-dihydroquinoline-3-carboxamide | 1, 10, 12 | 388.2 |
| 11 | 1-(4-fluorophenyl)-4-oxo-6-(2-(pyridin-2-yl)ethyl)-1,4-dihydroquinoline-3-carboxamide | 1, 10, 12 | 388.3 |
| 12 | 1-(4-fluorophenyl)-6-(methyl(pyridin-3-ylmethyl)amino)-4-oxo-1,4-dihydroquinoline-3-carboxamide | 1, 9 | 403.2 |
| 13 | 1-(2-fluoro-4-methoxyphenyl)-6-(2-(2-methylpyrimidin-5-yl)ethyl)-4-oxo-1,4-dihydroquinoline-3-carboxamide | 1, 10, 12 | 433.3 |
| 14 | 1-(3-fluoro-4-methoxyphenyl)-6-(2-(2-methylpyrimidin-5-yl)ethyl)-4-oxo-1,4-dihydroquinoline-3-carboxamide | 1, 10, 12 | 433.2 |
| 15 | 1-(4-methoxyphenyl)-6-(2-(2-methylpyrimidin-5-yl)ethyl)-4-oxo-1,4-dihydroquinoline-3-carboxamide | 1, 10, 12 | 415.2 |
| 16 | 1-(4-fluorophenyl)-4-oxo-6-(pyridin-3-ylamino)-1,4-dihydroquinoline-3-carboxamide | 1, 9 | 375.2 |
| 17 | 1-(4-fluorophenyl)-4-oxo-6-((pyridin-3-ylmethyl)amino)-1,4-dihydroquinoline-3-carboxamide | 1, 9 | 389.3 |
| 18 | 1-(4-fluorophenyl)-6-(methyl(pyridin-4-yl)amino)-4-oxo-1,4-dihydroquinoline-3-carboxamide | 1, 9 | 389.2 |
| 19 | 1-(4-fluorophenyl)-6-(methyl(pyridin-4-ylmethyl)amino)-4-oxo-1,4-dihydroquinoline-3-carboxamide | 1, 9 | 403.2 |
| 20 | 1-(4-fluorophenyl)-6-(methyl(pyridin-3-yl)amino)-4-oxo-1,4-dihydroquinoline-3-carboxamide | 1, 9 | 389.2 |
| 21 | 1-(4-fluorophenyl)-6-((6-methylpyridin-3-yl)methoxy)-4-oxo-1,4-dihydroquinoline-3-carboxamide | 1, 6, 7 | 404.2 |

| No. | Name | Examples used to prepare intermediate compound | ES-MS [H + 1]+ |
|---|---|---|---|
| 22 | 1-(3-methylisothiazol-5-yl)-6-(2-(2-methylpyrimidin-5-yl)ethyl)-4-oxo-1,4-dihydroquinoline-3-carboxamide | 1, 10, 12 | 406.2 |
| 23 | 1-(4-fluorophenyl)-4-oxo-6-(1-(pyridin-4-yl)ethoxy)-1,4-dihydroquinoline-3-carboxamide | 1, 6, 7 | 404.2 |
| 24 | 1-(4-fluorophenyl)-6-((2-methylpyridin-4-yl)methoxy)-4-oxo-1,4-dihydroquinoline-3-carboxamide | 1, 6, 7 | 404.3 |
| 25 | 1-(4-fluorophenyl)-4-oxo-6-(pyridin-4-ylmethoxy)-1,4-dihydroquinoline-3-carboxamide | 1, 6, 7 | 390.2 |
| 26 | 1-(4-fluorophenyl)-4-oxo-6-((2-(pyridin-4-yl)ethyl)amino)-1,4-dihydroquinoline-3-carboxamide | 1, 9 | 403.2 |
| 27 | 1-(4-fluorophenyl)-4-oxo-6-((2-(pyridin-3-yl)ethyl)amino)-1,4-dihydroquinoline-3-carboxamide | 1, 9 | 403.2 |
| 28 | 1-(4-fluorophenyl)-6-((2-morpholinoethyl)amino)-4-oxo-1,4-dihydroquinoline-3-carboxamide | 1, 9 | 411.2 |
| 29 | 1-(4-fluorophenyl)-6-((2-methylpyrimidin-5-yl)methoxy)-4-oxo-1,4-dihydroquinoline-3-carboxamide | 1, 6, 7 | 405.2 |
| 30 | 1-(4-fluorophenyl)-4-oxo-6-(1-(pyridin-3-yl)ethoxy)-1,4-dihydroquinoline-3-carboxamide | 1, 6, 7 | 404.2 |
| 31 | 1-(4-fluorophenyl)-6-(methyl((2-methylpyrimidin-5-yl)methyl)amino)-4-oxo-1,4-dihydroquinoline-3-carboxamide | 1, 9 | 418.2 |
| 32 | 1-(4-fluorophenyl)-6-(((3-fluoropyridin-4-yl)oxy)methyl)-4-oxo-1,4-dihydroquinoline-3-carboxamide | 1, 3, 5, 8 | 408.3 |
| 33 | 1-(4-fluorophenyl)-6-(((2-methylpyridin-4-yl)oxy)methyl)-4-oxo-1,4-dihydroquinoline-3-carboxamide | 1, 3, 5, 8 | 404.3 |
| 34 | 1-(4-fluorophenyl)-4-oxo-6-(((2-(trifluoromethyl)pyridin-4-yl)oxy)methyl)-1,4-dihydroquinoline-3-carboxamide | 1, 3, 5, 8 | 458.2 |
| 35 | 1-(4-fluorophenyl)-6-(((2-methylpyrimidin-5-yl)oxy)methyl)-4-oxo-1,4-dihydroquinoline-3-carboxamide | 1, 3, 5, 8 | 405.4 |
| 36 | 1-(4-fluorophenyl)-4-oxo-6-(((6-(trifluoromethyl)pyridin-3-yl)oxy)methyl)-1,4-dihydroquinoline-3-carboxamide | 1, 3, 5, 8 | 458.2 |
| 37 | 6-(((6-chloropyridin-3-yl)oxy)methyl)-1-(4-fluorophenyl)-4-oxo-1,4-dihydroquinoline-3-carboxamide | 1, 3, 5, 8 | 424.2 |
| 38 | 1-(4-fluorophenyl)-4-oxo-6-(2-(pyridin-3-yl)piperidin-1-yl)-1,4-dihydroquinoline-3-carboxamide | 1, 9 | 443.2 |
| 39 | 1-(4-fluorophenyl)-6-(((2-fluoropyridin-3-yl)oxy)methyl)-4-oxo-1,4-dihydroquinoline-3-carboxamide | 1, 3, 5, 8 | 408.3 |
| 40 | 1-(4-fluorophenyl)-4-oxo-6-(2-(pyridin-3-yl)pyrrolidin-1-yl)-1,4-dihydroquinoline-3-carboxamide | 1, 9 | 429.2 |
| 41 | 1-(4-fluorophenyl)-6-(((6-methylpyridin-3-yl)oxy)methyl)-4-oxo-1,4-dihydroquinoline-3-carboxamide | 1, 3, 5, 8 | 404.3 |
| 42 | 6-(ethyl(pyridin-3-ylmethyl)amino)-1-(4-fluorophenyl)-4-oxo-1,4-dihydroquinoline-3-carboxamide | 1, 9 | 417.2 |
| 43 | 1-(4-fluorophenyl)-4-oxo-6-(5H-pyrrolo[3,4-b]pyridin-6(7H)-yl)-1,4-dihydroquinoline-3-carboxamide | 1, 9 | 401.2 |
| 44 | 1-(4-fluorophenyl)-4-oxo-6-(pyridin-3-ylmethoxy)-1,4-dihydroquinoline-3-carboxamide | 1, 6, 7 | 390.2 |
| 45 | 1-(4-fluorophenyl)-6-(((6-fluoropyridin-3-yl)oxy)methyl)-4-oxo-1,4-dihydroquinoline-3-carboxamide | 1, 3, 5, 8 | 408.3 |
| 46 | 1-(4-fluorophenyl)-4-oxo-6-(2-(2-(trifluoromethyl)pyridin-4-yl)ethyl)-1,4-dihydroquinoline-3-carboxamide | 1, 11, 12 | 456.4 |
| 47 | 1-(4-fluorophenyl)-4-oxo-6-(2-(6-(trifluoromethyl)pyridin-3-yl)ethyl)-1,4-dihydroquinoline-3-carboxamide | 1, 11, 12 | 456.2 |
| 48 | 1-(4-fluorophenyl)-6-(2-(5-fluoropyridin-3-yl)ethyl)-4-oxo-1,4-dihydroquinoline-3-carboxamide | 1, 11, 12 | 406.4 |
| 49 | 8-fluoro-1-(4-fluorophenyl)-6-(2-(2-methylpyrimidin-5-yl)ethyl)-4-oxo-1,4-dihydroquinoline-3-carboxamide | 1, 10, 12 | 421.2 |
| 50 | 1-(4-fluorophenyl)-6-(3-morpholinopyrrolidin-1-yl)-4-oxo-1,4-dihydroquinoline-3-carboxamide | 1, 9 | 437.2 |
| 51 | 8-fluoro-1-(4-fluorophenyl)-6-(methyl(pyridin-3-ylmethyl)amino)-4-oxo-1,4-dihydroquinoline-3-carboxamide | 1, 9 | 421.2 |

Example 14

7-Fluoro-1-(4-fluorophenyl)-6-(methyl(pyridin-3-ylmethyl)amino)-4-oxo-1,4-dihydroquinoline-3-carboxamide (52)

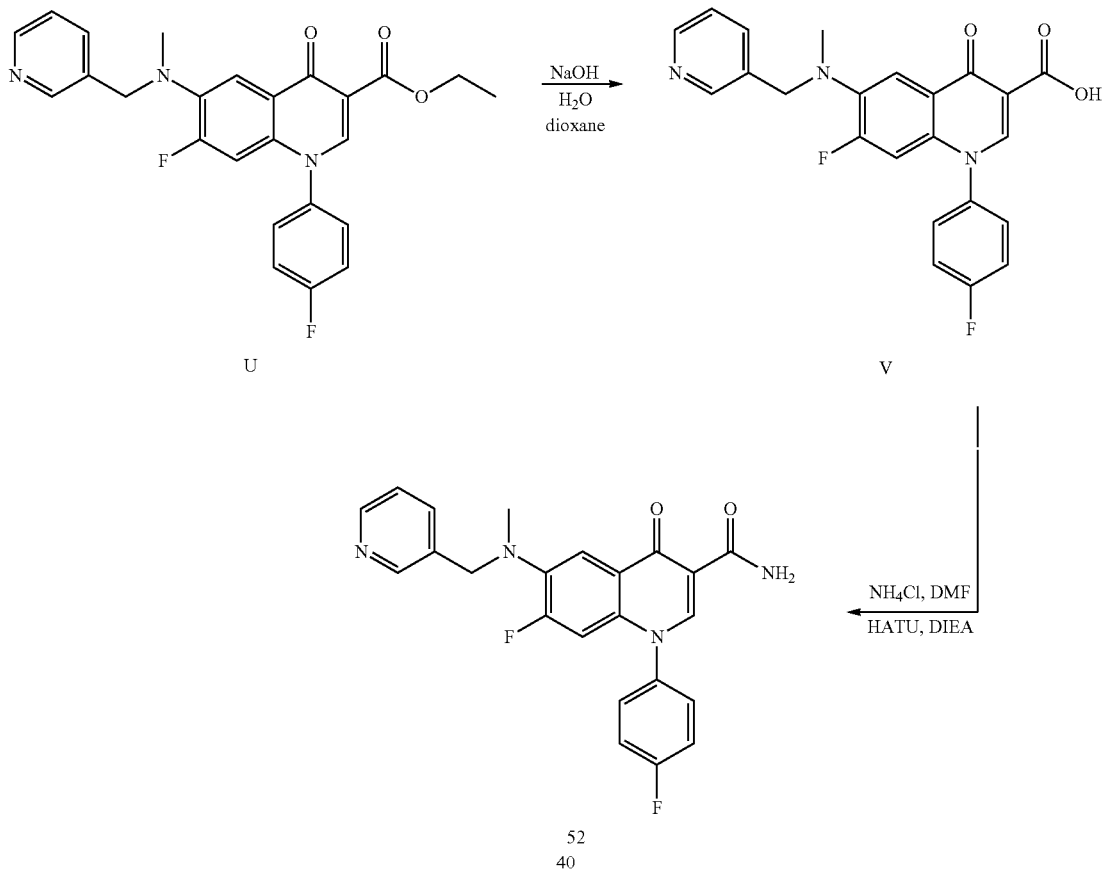

7-Fluoro-1-(4-fluorophenyl)-6-(methyl(pyridin-3-ylmethyl)amino)-4-oxo-1,4-dihydroquinoline-3-carboxylic acid (V)

Ethyl 7-fluoro-1-(4-fluorophenyl)-6-(methyl(pyridin-3-ylmethyl)amino)-4-oxo-1,4-dihydroquinoline-3-carboxylate (U) was prepared from 5-bromo-2,4-difluorobenzoyl chloride via a method analogous to that described in Examples 1 and 9. Compound U (27 mg, 0.060 mmol, 1.0 eq) was dissolved in 1,4-dioxane (0.5 mL) and 1N sodium hydroxide (0.12 mL, 0.12 mmol, 2.0 eq) was added. The reaction was stirred until complete by LCMS, at which time it was neutralized to pH 4-5 with 1N HCl and concentrated to dryness. The residue was suspended in 10% methanol in DCM and filtered. The organics were concentrated to afford 25 mg (99%) of the title compound as an off-white solid that was used without further purification. ES-MS [M+1]$^+$: 422.2.

7-Fluoro-1-(4-fluorophenyl)-6-(methyl(pyridin-3-ylmethyl)amino)-4-oxo-1,4-dihydroquinoline-3-carboxamide (52)

Compound U (26 mg, 0.062 mmol, 1.0 eq), ammonium chloride (6.6 mg, 0.12 mmol, 2.0 eq), (1-[bis(dimethylamino)methylene]-1H-1,2,3-triazolo[4,5-b]pyridinium 3-oxid hexafluorophosphate) (28 mg, 0.074 mmol, 1.2 eq) and N,N-diisopropylethylamine (43 µL, 0.25 mmol, 4.0 eq) were dissolved in DMF (0.5 mL) and stirred overnight. The reaction was diluted with ethyl acetate and washed with water (2×). The aqueous phase was back extracted with ethyl acetate and the combined organics were dried (MgSO$_4$), filtered and concentrated in vacuo. Purification by reverse phase chromatography afforded 7.0 mg (27%) of the title compound as white solid. $^1$H NMR (400 MHz, DMSO-d$_6$) δ 9.21 (d, J=4.4 Hz, 1H), 8.48-8.45 (m, 3H), 7.76-7.72 (m, 3H), 7.67 (dt, J=7.8, 1.7 Hz, 1H), 7.58 (d, J=4.4 Hz, 1H), 7.51 (t, J=8.7 Hz, 2H), 7.35 (dd, J=7.7, 4.9 Hz, 1H), 6.81 (d, J=14.0 Hz, 1H), 4.41 (s, 2H), 2.83 (s, 3H); ES-MS [M+1]$^+$: 421.2.

The following compounds were prepared in an analogous manner by first preparing the appropriate synthetic intermediate by use of the synthetic procedures indicated next to each compound:

| No. | Name | Examples used to prepare intermediate compound | ES-MS [M + 1]$^+$ |
|---|---|---|---|
| 53 | 1-(4-fluorophenyl)-4-oxo-6-((((tetrahydro-2H-pyran-4-yl)methyl)amino)-1,4-dihydroquinoline-3-carboxamide | 1, 9 | 396.2 |

| No. | Name | Examples used to prepare intermediate compound | ES-MS [M + 1]+ |
|---|---|---|---|
| 54 | 7-fluoro-1-(4-fluorophenyl)-6-(2-(2-methylpyrimidin-5-yl)ethyl)-4-oxo-1,4-dihydroquinoline-3-carboxamide | 1, 10, 12 | 421.2 |

Example 15

1-(4-Fluorophenyl)-6-((6-methylpyridin-3-yl)oxy)-4-oxo-1,4-dihydroquinoline-3-carboxamide (55)

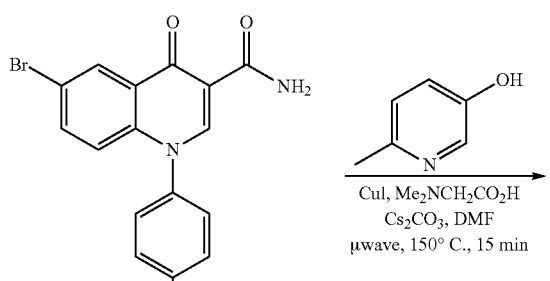

1-(4-Fluorophenyl)-6-((6-methylpyridin-3-yl)oxy)-4-oxo-1,4-dihydroquinoline-3-carboxamide (55)

Compound E (15 mg, 0.042 mmol, 1.0 eq), 5-hydroxy-2-methylpyridine (9.1 mg, 0.083 mmol, 2.0 eq), cesium carbonate (27 mg, 0.083 mmol, 2.0 eq), copper(I) iodide (0.79 mg, 0.0042 mmol, 0.10 eq) and N,N-dimethylglycine (1.3 mg, 0.013 mmol, 0.30 eq) were dissolved in DMF in a microwave vial and heated in a microwave reactor at 150° C. for 15 minutes. The reaction was filtered over Celite® and washed with 5% methanol in DCM. The organics were concentrated and purified using reverse phase chromatography to afford 9.1 mg (56%) of title compound as a white solid. $^1$H NMR (400 MHz, DMSO-d$_6$) δ 9.12 (d, J=4.3 Hz, 1H), 8.54 (s, 1H), 8.33 (d, J=2.8 Hz, 1H), 7.77-7.73 (m, 2H), 7.68 (d, J=3.0 Hz, 1H), 7.59 (d, J=4.3 Hz, 1H), 7.56-7.47 (m, 4H), 7.34 (d, J=8.5 Hz, 1H), 7.12 (d, J=9.2 Hz, 1H), 2.49 (s, 3H); ES-MS [M+1]$^+$: 390.4.

The following compounds were prepared in an analogous manner by first preparing the appropriate synthetic intermediate by use of the synthetic procedures indicated next to each compound:

| No. | Name | Examples used to prepare intermediate compound | ES-MS [M + 1]+ |
|---|---|---|---|
| 56 | 1-(4-fluorophenyl)-4-oxo-6-(pyridin-3-yloxy)-1,4-dihydroquinoline-3-carboxamide | 1, 2 | 376.2 |
| 57 | 1-(4-fluorophenyl)-6-((2-methylpyrimidin-5-yl)oxy)-4-oxo-1,4-dihydroquinoline-3-carboxamide | 1, 2 | 391.3 |
| 58 | 1-(4-fluorophenyl)-6-((6-fluoropyridin-3-yl)oxy)-4-oxo-1,4-dihydroquinoline-3-carboxamide | 1, 2 | 394.3 |
| 59 | 1-(4-fluorophenyl)-6-((5-fluoropyridin-3-yl)oxy)-4-oxo-1,4-dihydroquinoline-3-carboxamide | 1, 2 | 394.2 |

Example 16

1-(4-fluorophenyl)-4-oxo-6-(pyridin-3-yl)-1,4-dihydroquinoline-3-carboxamide (60)

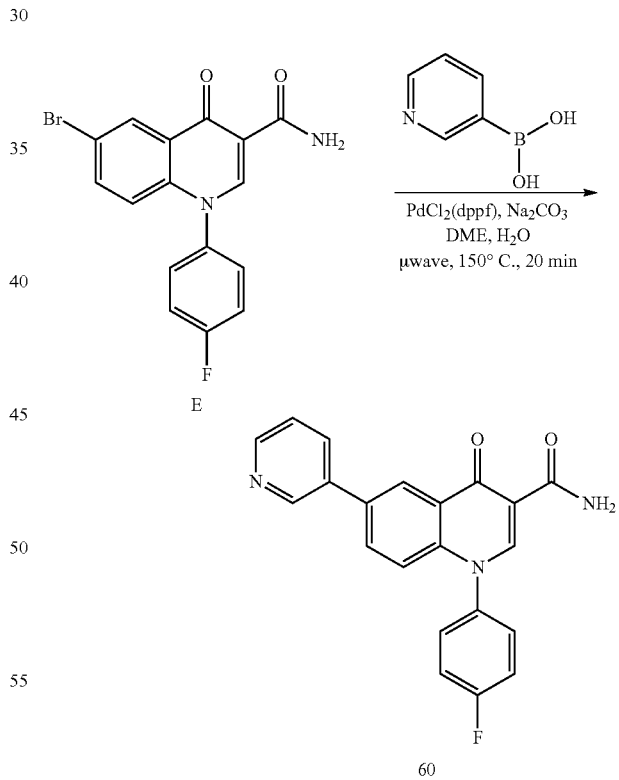

1-(4-fluorophenyl)-4-oxo-6-(pyridin-3-yl)-1,4-dihydroquinoline-3-carboxamide (60)

Compound E (15 mg, 0.042 mmol, 1.0 eq), 3-pyridinylboronic acid (11 mg, 0.087 mmol, 2.1 eq), [1,1'-bis(diphenylphosphino)ferrocene]dichloropalladium(II) (3.0 mg, 0.0042 mmol, 0.10 eq) and 1N sodium carbonate (0.21 mL, 0.21 mmol, 5.0 eq) were dissolved in dimethoxyethane (0.6 mL) in a microwave vial and heated at 150° C. for 20 minutes in a microwave reactor. The reaction was portioned between ethyl acetate and water and the layers separated. The aqueous phase was extracted with an additional portion of ethyl acetate and the combined organics were dried (MgSO₄), filtered and concentrated in vacuo. Purification by reverse phase chromatography afforded 10.1 mg (68%) of the title compound as white solid. ¹H NMR (400 MHz, DMSO-d₆) δ 9.21 (d, J=4.3 Hz, 1H), 8.96 (d, J=1.9 Hz, 1H), 8.62 (m, 2H), 8.60 (s, 1H), 8.17 (dt, J=8.0, 1.7 Hz, 1H), 8.09 (dd, J=8.8, 2.3 Hz, 1H), 7.81-7.78 (m, 2H), 7.66 (d, J=4.3 Hz, 1H), 7.57-7.52 (m, 3H), 7.16 (d, J=8.8 Hz, 1H); ES-MS [M+1]⁺: 360.2.

The following compounds were prepared in an analogous manner by first preparing the appropriate synthetic intermediate by use of the synthetic procedures indicated next to each compound:

| No. | Name | Examples used to prepare intermediate compound | ES-MS [M + 1]⁺ |
| --- | --- | --- | --- |
| 61 | 1-(4-fluorophenyl)-6-(1-methyl-1H-pyrazol-4-yl)-4-oxo-1,4-dihydroquinoline-3-carboxamide | 1, 2 | 363.2 |
| 62 | 1-(4-fluorophenyl)-6-(2-methylpyrimidin-5-yl)-4-oxo-1,4-dihydroquinoline-3-carboxamide | 1, 2 | 375.2 |
| 63 | 1-(4-fluorophenyl)-4-oxo-6-(pyridin-4-yl)-1,4-dihydroquinoline-3-carboxamide | 1, 2 | 360.2 |

Example 17

6-((cis-2,6-Dimethylmorpholino)methyl)-1-(4-fluorophenyl)-4-oxo-1,4-dihydroquinoline-3-carboxamide (64)

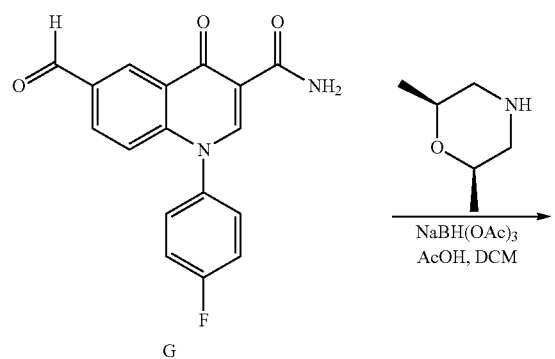

G

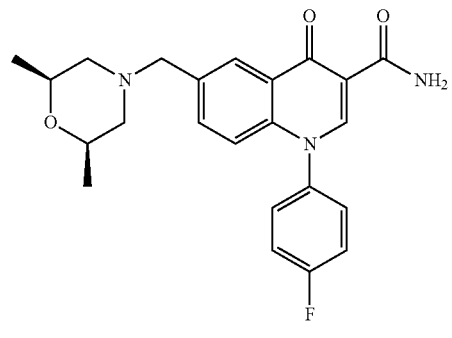

64

6-((cis-2,6-dimethylmorpholino)methyl)-1-(4-fluorophenyl)-4-oxo-1,4-dihydroquinoline-3-carboxamide (64)

A solution of compound G (10 mg, 0.032 mmol), cis-2,6-dimethylmorpholine (5 μL, 0.039 mmol), and acetic acid (4.6 μL, 0.081 mmol) in dichloromethane (1 mL) were stirred for one hour. To this mixture was added sodium triacetoxyborohydride (10.2 mg, 0.048 mmol). After 16 hours, the reaction was concentrated to dryness. Purification by reverse phase HPLC afforded 5 mg (38%) of the title compound. ¹H NMR (400 MHz, DMSO-d₆) δ 9.23 (d, J=4.4 Hz, 1H), 8.55 (s, 1H), 8.26 (d, J=1.8 Hz, 1H), 7.77-7.73 (m, 2H), 7.65 (dd, J=8.7, 2 Hz, 1H), 7.59 (d, J=4.4 Hz, 1H), 7.52 (t, J=8.68, 8.76, 2H), 7.03 (d, J=8.68, 1H), 3.57-3.52 (m, 4H), 2.65 (d, J=10.2 Hz, 2H), 1.01 (d, J=6.3 Hz, 6H); ES-MS [M+1]⁺: 410.3.

The following compounds were prepared in an analogous manner by first preparing the appropriate synthetic intermediate by use of the synthetic procedures indicated next to each compound:

| No. | Name | Examples used to prepare intermediate compound | ES-MS [M + 1]⁺ |
| --- | --- | --- | --- |
| 65 | 6-((6,6-difluoro-2-azaspiro[3.3]heptan-2-yl)methyl)-1-(4-fluorophenyl)-4-oxo-1,4-dihydroquinoline-3-carboxamide | 1, 2, 3 | 428.2 |
| 66 | 6-((4-cyclopropylpiperazin-1-yl)methyl)-1-(4-fluorophenyl)-4-oxo-1,4-dihydroquinoline-3-carboxamide | 1, 2, 3 | 421.2 |
| 67 | 1-(4-fluorophenyl)-6-((octahydroquinolin-1(2H)-yl)methyl)-4-oxo-1,4-dihydroquinoline-3-carboxamide | 1, 2, 3 | 434.2 |
| 68 | 6-((4,7-dimethyl-1,4-diazepan-1-yl)methyl)-1-(4-fluorophenyl)-4-oxo-1,4-dihydroquinoline-3-carboxamide | 1, 2, 3 | 423.2 |
| 69 | 6-((cyclopentyl(methyl)amino)methyl)-1-(4-fluorophenyl)-4-oxo-1,4-dihydroquinoline-3-carboxamide | 1, 2, 3 | 394.2 |
| 70 | 6-((cyclopropyl(methyl)amino)methyl)-1-(4-fluorophenyl)-4-oxo-1,4-dihydroquinoline-3-carboxamide | 1, 2, 3 | 366.2 |
| 71 | 6-(((1,4-thiazepan-4-yl)methyl)-1-(4-fluorophenyl)-4-oxo-1,4-dihydroquinoline-3-carboxamide | 1, 2, 3 | 412.2 |

-continued

| No. | Name | Examples used to prepare intermediate compound | ES-MS [M + 1]+ |
|---|---|---|---|
| 72 | 6-((1,4-oxazepan-4-yl)methyl)-1-(4-fluorophenyl)-4-oxo-1,4-dihydroquinoline-3-carboxamide | 1, 2, 3 | 396.2 |
| 73 | 6-(azepan-1-ylmethyl)-1-(4-fluorophenyl)-4-oxo-1,4-dihydroquinoline-3-carboxamide | 1, 2, 3 | 394.2 |
| 74 | 1-(4-fluorophenyl)-6-((4-methoxypiperidin-1-yl)methyl)-4-oxo-1,4-dihydroquinoline-3-carboxamide | 1, 2, 3 | 410.2 |
| 75 | 6-((4-cyanopiperidin-1-yl)methyl)-1-(4-fluorophenyl)-4-oxo-1,4-dihydroquinoline-3-carboxamide | 1, 2, 3 | 405.2 |
| 76 | 1-(4-fluorophenyl)-6-((4-(methylsulfonyl)piperidin-1-yl)methyl)-4-oxo-1,4-dihydroquinoline-3-carboxamide | 1, 2, 3 | 458.2 |
| 77 | 1-(4-fluorophenyl)-4-oxo-6-((4-(trifluoromethyl)piperidin-1-yl)methyl)-1,4-dihydroquinoline-3-carboxamide | 1, 2, 3 | 448.2 |
| 78 | 6-((4,4-difluoropiperidin-1-yl)methyl)-1-(4-fluorophenyl)-4-oxo-1,4-dihydroquinoline-3-carboxamide | 1, 2, 3 | 416.2 |
| 79 | 1-(4-fluorophenyl)-6-((2-methylmorpholino)methyl)-4-oxo-1,4-dihydroquinoline-3-carboxamide | 1, 2, 3 | 396.2 |
| 80 | 6-(((3,3-difluorocyclobutyl)(methyl)amino)methyl)-1-(4-fluorophenyl)-4-oxo-1,4-dihydroquinoline-3-carboxamide | 1, 2, 3 | 416.2 |
| 81 | 1-(4-fluorophenyl)-4-oxo-6-((4-(2,2,2-trifluoroethyl)piperazin-1-yl)methyl)-1,4-dihydroquinoline-3-carboxamide | 1, 2, 3 | 463.2 |
| 82 | 6-((4-acetylpiperazin-1-yl)methyl)-1-(4-fluorophenyl)-4-oxo-1,4-dihydroquinoline-3-carboxamide | 1, 2, 3 | 423.2 |
| 83 | 1-(4-fluorophenyl)-6-((4-(methylsulfonyl)piperazin-1-yl)methyl)-4-oxo-1,4-dihydroquinoline-3-carboxamide | 1, 2, 3 | 459.2 |
| 84 | 6-((1,1-dioxidothiomorpholino)methyl)-1-(4-fluorophenyl)-4-oxo-1,4-dihydroquinoline-3-carboxamide | 1, 2, 3 | 430.2 |
| 85 | 6-((1,1-dioxido-1,4-thiazepan-4-yl)methyl)-1-(4-fluorophenyl)-4-oxo-1,4-dihydroquinoline-3-carboxamide | 1, 2, 3 | 444.2 |
| 86 | 6-((3,3-difluoropyrrolidin-1-yl)methyl)-1-(4-fluorophenyl)-4-oxo-1,4-dihydroquinoline-3-carboxamide | 1, 2, 3 | 402.2 |
| 87 | 1-(4-fluorophenyl)-6-((4-methylpiperazin-1-yl)methyl)-4-oxo-1,4-dihydroquinoline-3-carboxamide | 1, 2, 3 | 395.2 |
| 88 | (S)-1-(4-fluorophenyl)-6-((2-methylmorpholino)methyl)-4-oxo-1,4-dihydroquinoline-3-carboxamide | 1, 2, 3 | 396.4 |
| 89 | (R)-1-(4-fluorophenyl)-6-((2-methylmorpholino)methyl)-4-oxo-1,4-dihydroquinoline-3-carboxamide | 1, 2, 3 | 396.4 |
| 90 | 6-((2,2-dimethylmorpholino)methyl)-1-(4-fluorophenyl)-4-oxo-1,4-dihydroquinoline-3-carboxamide | 1, 2, 3 | 410.4 |
| 91 | 6-(((3,3-difluorocyclobutyl)(methyl)amino)methyl)-8-fluoro-1-(4-fluorophenyl)-4-oxo-1,4-dihydroquinoline-3-carboxamide | 1, 2, 3 | 434.3 |
| 92 | 6-((cis-2,6-dimethylmorpholino)methyl)-8-fluoro-1-(4-fluorophenyl)-4-oxo-1,4-dihydroquinoline-3-carboxamide | 1, 2, 3 | 428.4 |
| 93 | 8-fluoro-1-(4-fluorophenyl)-6-((2-methylmorpholino)methyl)-4-oxo-1,4-dihydroquinoline-3-carboxamide | 1, 2, 3 | 414.2 |
| 94 | 6-((4,4-difluoropiperidin-1-yl)methyl)-8-fluoro-1-(4-fluorophenyl)-4-oxo-1,4-dihydroquinoline-3-carboxamide | 1, 2, 3 | 434.2 |
| 95 | 6-((3,3-difluoropyrrolidin-1-yl)methyl)-8-fluoro-1-(4-fluorophenyl)-4-oxo-1,4-dihydroquinoline-3-carboxamide | 1, 2, 3 | 420.2 |

Example 18

1-(4-Fluorophenyl)-6-(methyl(pyridin-3-ylmethyl)amino)-4-oxo-1,4-dihydroquinoline-3-carbonitrile (96)

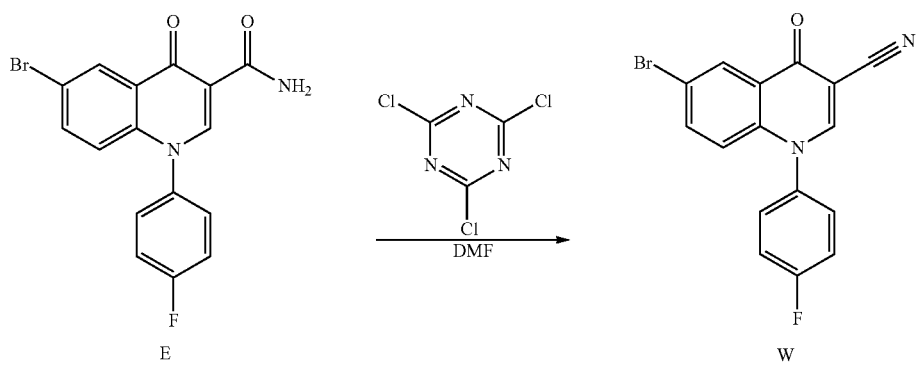

-continued

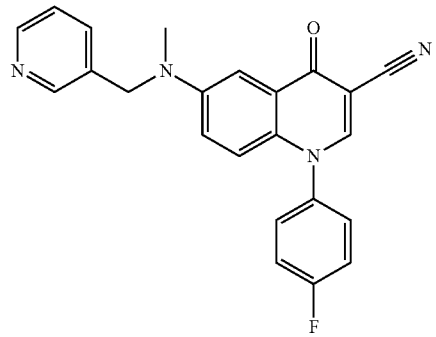

96

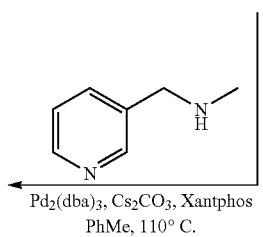

Pd₂(dba)₃, Cs₂CO₃, Xantphos
PhMe, 110° C.

6-bromo-1-(4-fluorophenyl)-4-oxo-1,4-dihydro-quinoline-3-carbonitrile (W)

Compound E (30 mg, 0.083 mmol, 1.0 eq) and cyanuric chloride (15 mg, 0.083 mmol, 1.0 eq) were dissolved in DMF (0.5 mL) and the reaction was stirred at room temperature for 30 minutes. The reaction was diluted with ethyl acetate and washed with saturated sodium bicarbonate. The organic phase was dried (MgSO₄), filtered and concentrated in vacuo. Purification by reverse phase chromatography afforded 10.1 mg (68%) of the title compound as white solid. $^1$H NMR (400 MHz, DMSO-d₆) δ 8.94 (s, 1H), 8.30 (d, J=2.4 Hz, 1H), 7.86 (dd, J=9.0, 2.4 Hz, 1H), 7.75-7.72 (m, 2H), 7.53 (t, J=8.7 Hz, 2H), 6.96 (d, J=9.1 Hz, 1H); ES-MS [M+1]⁺: 343.2.

1-(4-fluorophenyl)-6-(methyl(pyridin-3-ylmethyl) amino)-4-oxo-1,4-dihydroquinoline-3-carbonitrile (96)

Compound W (25 mg, 0.073 mmol, 1.0 eq), N-methyl-N-(3-pyridylmethyl)amine (17 mg, 0.15 mmol, 2.0 eq), cesium carbonate (33 mg, 0.10 mmol, 1.4 eq), tris(dibenzylideneacetone)dipalladium(0) (5.3 mg, 0.0058 mmol, 0.080 eq) and 4,5-bis(diphenylphosphino)-9,9-dimethylxanthene (5.1 mg, 0.0087 mmol, 0.12 eq) were dissolved in toluene (0.5 mL) in a sealed vial and heated at 110° C. overnight. The reaction was cooled, filtered over Celite® and washed with 5% methanol in DCM. The organics were concentrated and purified using reverse phase chromatography to afford 11.3 mg (40%) of the title compound as a yellow solid. $^1$H NMR (400 MHz, DMSO-d₆) δ 8.65 (s, 1H), 8.44-8.42 (m, 2H), 7.70-7.67 (m, 2H), 7.57 (dt, J=7.8, 1.8 Hz, 1H), 7.48 (t, J=8.7 Hz, 2H), 7.33-7.32 (m, 2H), 7.26 (dd, J=9.4, 3.1 Hz, 1H), 6.83 (d, J=9.3 Hz, 1H), 4.72 (s, 2H), 3.1 (s, 3H); ES-MS [M+1]⁺: 385.2.

Example 19

Biological Activity

A. mGlu₂ Ca²⁺ Flux Assay

G$_{\alpha15}$ HEK293 cells stably expressing rat mGlu₂ were plated in black-walled, clear-bottomed, poly-D-lysine coated 384-well plates in 20 μL of assay medium (DMEM containing 10% dialyzed FBS, 20 mM HEPES, and 1 mM sodium pyruvate) at a density of 12K cells/well. The cells were grown overnight at 37° C. in the presence of 5% CO₂. The next day, medium was removed and the cells incubated with 20 μL of 2.3 μM Fluo-4, AM prepared as a 2.3 mM stock in DMSO and mixed in a 1:1 ratio with 10% (w/v) pluronic acid F-127 and diluted in assay buffer (Hank's balanced salt solution, 20 mM HEPES, and 2.5 mM probenecid) for 45 minutes at 37° C. Dye was removed, 20 μL of assay buffer was added, and the plate was incubated for 5 minutes at room temperature.

Ca²⁺ flux was measured using the Functional Drug Screening System (FDSS7000, Hamamatsu, Japan). After establishment of a fluorescence baseline for about 3 seconds, the compounds of the present invention were added to the cells, and the response in cells was measured. 2.3 minutes later an EC₂₀ concentration of the mGlu₂ receptor agonist glutamate was added to the cells, and the response of the cells was measured for 1.9 minutes; an EC₈₀ concentration of agonist was added and readings taken for an additional 1.7 minutes. All test compounds were dissolved and diluted to a concentration of 10 mM in 100% DMSO. Compounds were then serially diluted 1:3 in DMSO into 10 point concentration response curves, transferred to daughter plates, and further diluted into assay buffer to a 2× stock. Calcium fluorescence measures were recorded as fold over basal fluorescence; raw data was then normalized to the maximal response to glutamate. Antagonism of the agonist response of the mGlu₂ receptor in the present invention was observed as a decrease in response to nearly maximal concentrations of glutamate in the presence of compound compared to the response to glutamate in the absence of compound.

The raw data file containing all time points was used as the data source in the analysis template. This was saved by the FDSS as a tab-delimited text file. Data were normalized using a static ratio function (F/F₀) for each measurement of the total 360 values per well divided by each well's initial value. Data were then reduced to peak amplitudes (Max–Initial Min) using a time range that starts approximately 3 seconds prior to the glutamate EC₈₀ addition and continues for approximately 90 seconds. This is sufficient time to capture the peak amplitude of the cellular calcium response. Individual amplitudes were expressed as % EC$_{Max}$ by multiplying each amplitude by 100 and then dividing the product by the mean of the amplitudes derived from the glutamate EC$_{Max}$-treated wells. IC50 values for test compounds were generated by fitting the normalized values versus the log of the test compound concentration (in mol/L) using a 4 parameter logistic equation where none of the parameters were fixed. Each of the three values collected at each concentration of test compound were weighted evenly.

A compound was designated as a negative allosteric modulator (NAM) if the compound showed a concentration-dependent decrease in the glutamate EC₈₀ addition. For NAMs, potency ($IC_{50}$) and maximum response (% Glu Max), i.e. the amplitude of response in the presence of 30 μM test compound as a percentage of the maximal response to glutamate, are reported. For NAMs that show a decrease in the $EC_{80}$ response, but do not hit a plateau, the average of the maximum response at a single concentration (30 μM) was determined (% Glu Max) and potencies were reported as ">10,000 nM". Compounds with no measurable activity are designated as ">30,000 nM" since the top concentration of compound tested in the assay is 30 μM.

B. Results and Discussion of Biological Activity Data

The results of these assays are shown in Table 1. The data in Table 1 demonstrates that the disclosed compounds are negative allosteric modulators of $mGlu_2$ and show high affinity for the $mGlu_2$ receptor(s). Data is from a single experiment unless otherwise noted. Data that is an average of two experiments is noted as "n=2" while data that is an average of three or more experiments is presented as the average plus or minus the standard error of the mean.

TABLE 1

| Compound | rat $mGlu_2$ $IC_{50}$ (nM) | rat $mGlu_2$ Glu max (%) |
|---|---|---|
| 1 | 227 ± 55 | 1.52 ± 0.26 |
| 2 | 440 ± 97 | 1.52 ± 0.63 |
| 3 | 3910 | −0.78 |
| 4 | >10,000 | 53.77 |
| 5 | 10,000 | 4.65 |
| 6 | >10,000 | 68.47 |
| 7 | >10,000 | 42.15 |
| 8 | >10,000 | 18.67 |
| 9 | 492 ± 97 | 1.88 ± 0.38 |
| 10 | 482 ± 87 | 1.90 ± 0.11 |
| 11 | 2590 | 0.92 |
| 12 | 202 ± 14 | 2.39 ± 0.13 |
| 13 | 311 (n = 2) | 1.14 (n = 2) |
| 14 | 252 (n = 2) | 1.15 (n = 2) |
| 15 | 139 (n = 2) | 1.61 (n = 2) |
| 16 | 433 (n = 2) | 1.77 (n = 2) |
| 17 | 421 (n = 2) | 1.05 (n = 2) |
| 18 | 1150 | 1.73 |
| 19 | 224 (n = 2) | 1.02 (n = 2) |
| 20 | 155 (n = 2) | 1.33 (n = 2) |
| 21 | 541 ± 116 | 1.55 ± 0.39 |
| 22 | 419 ± 46 | 1.20 ± 0.50 |
| 23 | 460 ± 62 | 1.07 ± 0.13 |
| 24 | 422 ± 94 | 1.09 ± 0.16 |
| 25 | 1230 | 0.97 |
| 26 | 444 (n = 2) | 1.91 (n = 2) |
| 27 | 391 (n = 2) | 1.75 (n = 2) |
| 28 | 1150 | 0.77 |
| 29 | 843 | 1.92 |
| 30 | 391 ± 44 | 1.31 ± 0.45 |
| 31 | 153 ± 33 | 1.86 ± 0.26 |
| 32 | 243 ± 63 | 1.83 ± 0.20 |
| 33 | 421 (n = 2) | 2.18 (n = 2) |
| 34 | 534 | 1.97 |
| 35 | 287 ± 51 | 1.71 ± 0.20 |
| 36 | 1460 | 1.28 |
| 37 | 203 ± 42 | 1.70 ± 0.12 |
| 38 | 900 | 1.68 |
| 39 | 883 | 0.83 |
| 40 | 429 | 1.81 |
| 41 | 265 ± 73 | 1.62 ± 0.23 |
| 42 | 167 | 2.57 |
| 43 | 5040 | 1.85 |
| 44 | 1080 | 1.67 |
| 45 | 352 (n = 2) | 1.47 (n = 2) |
| 46 | 269 | 0.78 |
| 47 | 1550 | 1.21 |
| 48 | 1030 | 1.40 |
| 49 | 155 (n = 2) | 1.53 (n = 2) |
| 50 | 1320 | 1.08 |
| 51 | 1180 | 1.39 |
| 52 | 669 | 2.26 |
| 53 | 659 | 1.04 |
| 54 | 2700 | 1.02 |
| 55 | 1710 | 1.96 |
| 56 | 882 ± 160 | 1.84 ± 0.47 |
| 57 | 4480 | 15.71 |
| 58 | 1360 | 1.18 |
| 59 | 2110 | 0.44 |
| 60 | 277 | 1.33 |
| 61 | 544 (n = 2) | 0.41 (n = 2) |
| 62 | >10,000 | 30.30 |
| 63 | 407 | 0.97 |
| 64 | 222 ± 36 | 1.42 ± 0.51 |
| 65 | 2020 | 1.93 |
| 66 | 1290 | 1.89 |
| 67 | 617 | 2.40 |
| 68 | 4040 | 2.47 |
| 69 | 2190 | 1.39 |
| 70 | 821 | 1.33 |
| 71 | 164 (n = 2) | 2.06 (n = 2) |
| 72 | >10,000 | 29.60 |
| 73 | 2590 | 0.96 |
| 74 | 1880 | 1.23 |
| 75 | 735 | 1.02 |
| 76 | 1120 | 1.29 |
| 77 | 823 | 1.41 |
| 78 | 197 ± 91 | 1.59 ± 0.27 |
| 79 | 328 ± 64 | 1.31 ± 0.04 |
| 80 | 397 (n = 2) | 1.03 (n = 2) |
| 81 | 753 | 1.19 |
| 82 | 3190 | 2.14 |
| 83 | 694 | 1.47 |
| 84 | 1160 | 2.04 |
| 85 | 422 ± 52 | 1.24 ± 0.04 |
| 86 | 259 (n = 2) | 0.98 (n = 2) |
| 87 | 1360 | 0.93 |
| 88 | 724 | 1.36 |
| 89 | 1150 | 1.08 |
| 90 | 142 (n = 2) | 2.01 (n = 2) |
| 91 | >30,000 | N/A |
| 92 | 4410 | 2.23 |
| 93 | 6520 | 0.14 |
| 94 | 1770 | 5.78 |
| 95 | >10,000 | 31.09 |
| 96 | 3160 | 3.44 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A compound of formula (I)

(I)

or a pharmaceutically acceptable salt thereof, wherein
$R^1$ is aryl heteroaryl;
$R^{2a}$, $R^{2b}$, and $R^{2c}$ are each independently selected from hydrogen, halogen, $C_1$-$C_4$ alkyl, $C_1$-$C_4$ alkoxy, $C_1$-$C_4$ haloalkyl, and $C_1$-$C_4$ haloalkoxy;
$R^3$ is —X—$(CR^{8a}R^{8b})_p$—Z—$(CR^{8c}R^{8d})_q$—N$(R^{7a})(R^{7b})$, —X—$(CR^{8a}R^{8b})_p$—Z—$(CR^{8c}R^{8d})_q$—Y-A, -A'—X—$(CR^{8a}R^{8b})_p$—N$(R^{7a})(R^{7b})$, or -A'—X—$(CR^{8a}R^{8b})_p$—Y-A;
p is 0-2;
q is 0-2;
X, Y, and Z are each independently selected from a bond, $CR^{8e}R^{8f}$, O, S, $NR^{10}$, —C(O)—, —O—C(O)—, —C(O)—O—, —O—C(O)—$NR^{10}$—, —C(O)—$NR^{10}$—, —$NR^{10}$—C(O)—, —$NR^{10}$—C(O)—O—, —$NR^{10}$—C(O)—NR—, —$NR^{10}$—$SO_2$—, and —$SO_2$—;
$R^{7a}$ and $R^{7b}$ are each independently selected from $C_1$-$C_7$ alkyl, $C_1$-$C_7$ haloalkyl, cycloalkyl, $C_1$-$C_7$ heteroalkyl, and heterocycle, or $R^{7a}$ and $R^{7b}$ together with the nitrogen atom to which they attach form a heterocycle;
$R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy;
$R^{10}$ at each occurrence is independently selected from hydrogen, $C_1$-$C_4$ alkyl, and $C_1$-$C_4$ haloalkyl;
A is aryl, heteroaryl, cycloalkyl, or heterocycle;
A' is aryl, heteroaryl, cycloalkyl, or heterocycle; and
$R^4$ is —$CONH_2$ or cyano;
wherein said aryl, heteroaryl, cycloalkyl, and heterocycle, at each occurrence, are independently substituted or unsubstituted.

2. The compound of claim 1, wherein
$R^1$ is aryl or heteroaryl, substituted with 0-3 substituents independently selected from fluoro, chloro, cyano, $C_1$-$C_6$ alkyl, $C_1$-$C_6$ fluoroalkyl, $C_1$-$C_6$ alkoxyalkyl, cyclopropyl, fluorocyclopropyl, $OR^5$, and $NR^{6a}R^{6b}$; wherein
$R^5$ is hydrogen, $C_1$-$C_6$ alkyl or $C_1$-$C_6$ fluoroalkyl; and
$R^{6a}$ and $R^{6b}$ are each independently hydrogen, $C_1$-$C_6$ alkyl, cyclopropyl, cyclobutyl, or $C_1$-$C_6$ heteroalkyl; or $R^{6a}$ and $R^{6b}$ together with the nitrogen atom to which they are attach form a heterocycle; wherein each $R^{6a}$ and $R^{6b}$ are substituted with 0-3 fluorine atoms.

3. The compound of claim 1, wherein $R^1$ is aryl substituted with 0-2 substituents independently selected from fluoro, chloro, $C_1$-$C_3$ alkyl, $C_1$-$C_3$ fluoroalkyl, $C_1$-$C_3$ alkoxyalkyl, and $OR^5$; wherein $R^5$ is hydrogen, $C_1$-$C_3$ alkyl, or $C_1$-$C_3$ fluoroalkyl.

4. The compound of claim 1, wherein $R^1$ is heteroaryl substituted with 0-2 substituents independently selected from fluoro, chloro, $C_1$-$C_3$ alkyl, $C_1$-$C_3$ fluoroalkyl, and $C_1$-$C_3$ alkoxyalkyl.

5. The compound of claim 1, wherein $R^{2a}$, $R^{2b}$, and $R^{2c}$ are each independently hydrogen, fluoro, or chloro.

6. The compound of claim 1, wherein $R^{2a}$, $R^{2b}$, and $R^{2c}$ are each hydrogen.

7. The compound of claim 1, wherein
$R^3$ is —X—$(CR^{8a}R^{8b})_p$—Z—$(CR^{8c}R^{8d})_q$—N$((R^{7a})(R^{7b}))$, —X—$(CR^{8a}R^{8b})_p$—Z—$(CR^{8c}R^{8d})_q$—Y-A, -A'—X—$(CR^{8a}R^{8b})_p$—N$(R^{7a})(R^{7b})$, or -A'—X—$(CR^{8a}R^{8b})_p$—Y-A; wherein
p is 0-2;
q is 0-2;
X is a bond, $CR^{8e}R^{8f}$, O, or $NR^{10}$;
Y is a bond, $CR^{8e}R^{8f}$, O, or $NR^{10}$;
$R^{7a}$ and $R^{7b}$ are each independently selected from $C_1$-$C_7$ alkyl, cycloalkyl, $C_1$-$C_7$ heteroalkyl, and heterocycle, or $R^{7a}$ and $R^{7b}$ together with the nitrogen atom to which they attach form a heterocycle;
$R^{8a}$, $R^{8b}$, $R^{8c}$, $R^{8d}$, $R^{8e}$ and $R^{8f}$, at each occurrence, are independently selected from hydrogen, halogen, $C_1$-$C_4$ alkyl, $C_1$-$C_4$ alkoxy, $C_1$-$C_4$ haloalkyl, and $C_1$-$C_4$ haloalkoxy;
$R^{10}$ at each occurrence is independently selected from hydrogen, $C_1$-$C_4$ alkyl, and $C_1$-$C_4$ haloalkyl;
A is aryl, heteroaryl, cycloalkyl, or heterocycle; and
A' is cycloalkyl or heterocycle.

8. The compound of claim 1, wherein $R^3$ is

107

-continued

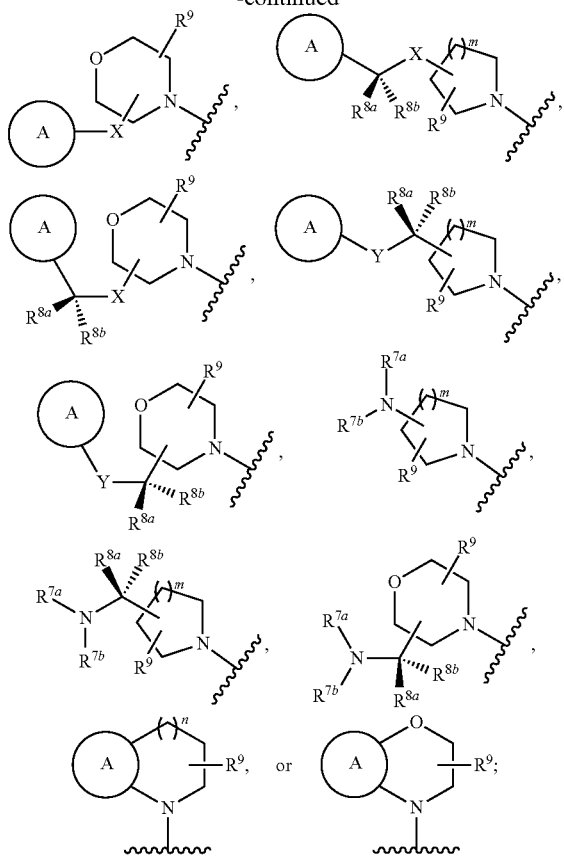

wherein
X is a bond, $CR^{8e}R^{8f}$, O, or $NR^{10}$;
Y is a bond, $CR^{8e}R^{8f}$, O, or $NR^{10}$;
$R^{7a}$ and $R^{7b}$ are each independently selected from $C_1$-$C_7$ alkyl, $C_3$-$C_7$ cycloalkyl, $C_1$-$C_7$ heteroalkyl, and monocyclic heterocycle, or $R^{7a}$ and $R^{7b}$ together with the nitrogen atom to which they attach form a heterocycle; wherein $R^{7a}$ and $R^{7b}$ are substituted with 0-3 fluorine atoms;
$R^{8a}$, $R^{8b}$, $R^{8c}$, $R^{8d}$, $R^{8e}$ and $R^{8f}$ are each independently selected from hydrogen, fluoro, and methyl;
$R^9$ at each occurrence is independently selected from fluoro, methyl, heterocycle, and heteroaryl; wherein 0-4 $R^9$ groups are present in each $R^3$;
m is 0-3;
n is 0-2;
$R^{10}$ is hydrogen, $C_1$-$C_3$ alkyl, or $C_1$-$C_3$ fluoroalkyl;
A is an aryl group of 6-10 atoms, a heteroaryl group of 5-10 atoms, $C_3$-$C_7$ cycloalkyl, a heterocycle group of 4-10 atoms, or a spiro heterocycle group of 7-10 atoms; wherein A is substituted with 0-3 substituents independently selected from fluoro, chloro, cyano, methyl, $C_1$-$C_3$ fluoroalkyl, cycloalkyl, $OR^{11}$, $NR^{12a}R^{12b}$, $SO_2R^{11}$, and $COR^{11}$; wherein
$R^{11}$ is independently selected from hydrogen, $C_1$-$C_3$ alkyl, and $C_1$-$C_3$ fluoroalkyl;
$R^{12a}$ and $R^{12b}$ are each independently selected from hydrogen, $C_1$-$C_4$ alkyl, cyclopropyl, cyclobutyl, and $C_1$-$C_4$ heteroalkyl; or $R^{12a}$ and $R^{12b}$ together with the nitrogen atom to which they attach form a heterocycle; wherein each $R^{12a}$ and $R^{12b}$ are each independently substituted with 0-3 fluorine atoms.

108

9. The compound of claim 1, wherein $R^3$ is

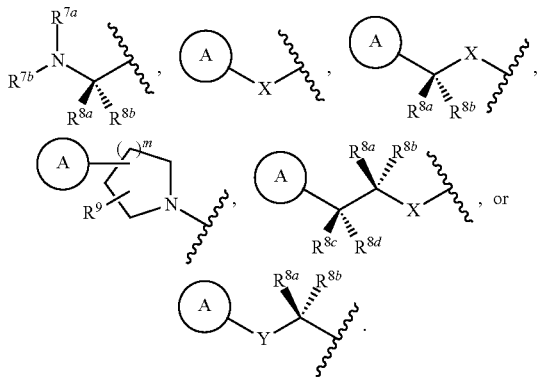

10. The compound of claim 1, wherein $R^4$ is —$CONH_2$.
11. The compound of claim 1, wherein $R^4$ is cyano.
12. The compound of claim 1, selected from the group consisting of:
1-(4-fluorophenyl)-4-oxo-6-(thiomorpholinomethyl)-1,4-dihydroquinoline-3-carboxamide;
1-(4-fluorophenyl)-6-(morpholinomethyl)-4-oxo-1,4-dihydroquinoline-3-carboxamide;
1-(4-fluorophenyl)-4-oxo-6-(piperidin-1-ylmethyl)-1,4-dihydroquinoline-3-carboxamide;
1-(4-fluorophenyl)-4-oxo-6-phenethyl-1,4-dihydroquinoline-3-carboxamide;
1-(4-fluorophenyl)-6-(4-methylphenethyl)-4-oxo-1,4-dihydroquinoline-3-carboxamide;
1-(4-fluorophenyl)-6-(3-methylphenethyl)-4-oxo-1,4-dihydroquinoline-3-carboxamide;
1-(4-fluorophenyl)-6-(2-methylphenethyl)-4-oxo-1,4-dihydroquinoline-3-carboxamide;
1-(4-fluorophenyl)-4-oxo-6-(2-(pyridin-4-yl)ethyl)-1,4-dihydroquinoline-3-carboxamide;
1-(4-fluorophenyl)-4-oxo-6-(2-(pyridin-3-yl)ethyl)-1,4-dihydroquinoline-3-carboxamide;
1-(4-fluorophenyl)-4-oxo-6-(2-(pyridin-2-yl)ethyl)-1,4-dihydroquinoline-3-carboxamide;
1-(4-fluorophenyl)-6-(methyl(pyridin-3-ylmethyl)amino)-4-oxo-1,4-dihydroquinoline-3-carboxamide;
1-(4-fluorophenyl)-4-oxo-6-(pyridin-3-yloxy)-1,4-dihydroquinoline-3-carboxamide;
1-(4-fluorophenyl)-6-(2-(2-methylpyrimidin-5-yl)ethyl)-4-oxo-1,4-dihydroquinoline-3-carboxamide;
1-(2-fluoro-4-methoxyphenyl)-6-(2-(2-methylpyrimidin-5-yl)ethyl)-4-oxo-1,4-dihydroquinoline-3-carboxamide;
1-(3-fluoro-4-methoxyphenyl)-6-(2-(2-methylpyrimidin-5-yl)ethyl)-4-oxo-1,4-dihydroquinoline-3-carboxamide;
1-(4-methoxyphenyl)-6-(2-(2-methylpyrimidin-5-yl)ethyl)-4-oxo-1,4-dihydroquinoline-3-carboxamide;
1-(4-fluorophenyl)-4-oxo-6-(pyridin-3-ylamino)-1,4-dihydroquinoline-3-carboxamide;
1-(4-fluorophenyl)-4-oxo-6-((pyridin-3-ylmethyl)amino)-1,4-dihydroquinoline-3-carboxamide;
1-(4-fluorophenyl)-6-(methyl(pyridin-4-yl)amino)-4-oxo-1,4-dihydroquinoline-3-carboxamide;
1-(4-fluorophenyl)-6-(methyl(pyridin-4-ylmethyl)amino)-4-oxo-1,4-dihydroquinoline-3-carboxamide;
1-(4-fluorophenyl)-6-((2-methylpyrimidin-5-yl)oxy)-4-oxo-1,4-dihydroquinoline-3-carboxamide;

1-(4-fluorophenyl)-6-((6-fluoropyridin-3-yl)oxy)-4-oxo-1,4-dihydroquinoline-3-carboxamide;
1-(4-fluorophenyl)-6-((5-fluoropyridin-3-yl)oxy)-4-oxo-1,4-dihydroquinoline-3-carboxamide;
1-(4-fluorophenyl)-6-((6-methylpyridin-3-yl)oxy)-4-oxo-1,4-dihydroquinoline-3-carboxamide;
1-(4-fluorophenyl)-6-(methyl(pyridin-3-yl)amino)-4-oxo-1,4-dihydroquinoline-3-carboxamide;
6-((6,6-difluoro-2-azaspiro[3.3]heptan-2-yl)methyl)-1-(4-fluorophenyl)-4-oxo-1,4-dihydroquinoline-3-carboxamide;
6-((4-cyclopropylpiperazin-1-yl)methyl)-1-(4-fluorophenyl)-4-oxo-1,4-dihydroquinoline-3-carboxamide;
1-(4-fluorophenyl)-6-((octahydroquinolin-1 (2H)-yl)methyl)-4-oxo-1,4-dihydroquinoline-3-carboxamide;
6-((4,7-dimethyl-1,4-diazepan-1-yl)methyl)-1-(4-fluorophenyl)-4-oxo-1,4-dihydroquinoline-3-carboxamide;
6-((cyclopentyl(methyl)amino)methyl)-1-(4-fluorophenyl)-4-oxo-1,4-dihydroquinoline-3-carboxamide;
6-((cyclopropyl(methyl)amino)methyl)-1-(4-fluorophenyl)-4-oxo-1,4-dihydroquinoline-3-carboxamide;
6-((1,4-thiazepan-4-yl)methyl)-1-(4-fluorophenyl)-4-oxo-1,4-dihydroquinoline-3-carboxamide;
6-((1,4-oxazepan-4-yl)methyl)-1-(4-fluorophenyl)-4-oxo-1,4-dihydroquinoline-3-carboxamide;
6-(azepan-1-ylmethyl)-1-(4-fluorophenyl)-4-oxo-1,4-dihydroquinoline-3-carboxamide;
1-(4-fluorophenyl)-6-((4-methoxypiperidin-1-yl)methyl)-4-oxo-1,4-dihydroquinoline-3-carboxamide;
6-((4-cyanopiperidin-1-yl)methyl)-1-(4-fluorophenyl)-4-oxo-1,4-dihydroquinoline-3-carboxamide;
1-(4-fluorophenyl)-6-((4-(methyl sulfonyl)piperidin-1-yl)methyl)-4-oxo-1,4-dihydroquinoline-3-carboxamide;
1-(4-fluorophenyl)-4-oxo-6-((4-(trifluoromethyl)piperidin-1-yl)methyl)-1,4-dihydroquinoline-3-carboxamide;
6-((4,4-difluoropiperidin-1-yl)methyl)-1-(4-fluorophenyl)-4-oxo-1,4-dihydroquinoline-3-carboxamide;
1-(4-fluorophenyl)-6-((2-methylmorpholino)methyl)-4-oxo-1,4-dihydroquinoline-3-carboxamide;
6-(((3,3-difluorocyclobutyl)(methyl)amino)methyl)-1-(4-fluorophenyl)-4-oxo-1,4-dihydroquinoline-3-carboxamide;
6-((cis-2,6-dimethylmorpholino)methyl)-1-(4-fluorophenyl)-4-oxo-1,4-dihydroquinoline-3-carboxamide;
1-(4-fluorophenyl)-4-oxo-6-((4-(2,2,2-trifluoroethyl)piperazin-1-yl)methyl)-1,4-dihydroquinoline-3-carboxamide;
6-((4-acetylpiperazin-1-yl)methyl)-1-(4-fluorophenyl)-4-oxo-1,4-dihydroquinoline-3-carboxamide;
1-(4-fluorophenyl)-6-((4-(methylsulfonyl)piperazin-1-yl)methyl)-4-oxo-1,4-dihydroquinoline-3-carboxamide;
6-((1,1-dioxidothiomorpholino)methyl)-1-(4-fluorophenyl)-4-oxo-1,4-dihydroquinoline-3-carboxamide;
6-((1,1-dioxido-1,4-thiazepan-4-yl)methyl)-1-(4-fluorophenyl)-4-oxo-1,4-dihydroquinoline-3-carboxamide;
6-((3,3-difluoropyrrolidin-1-yl)methyl)-1-(4-fluorophenyl)-4-oxo-1,4-dihydroquinoline-3-carboxamide;
1-(4-fluorophenyl)-6-((4-methylpiperazin-1-yl)methyl)-4-oxo-1,4-dihydroquinoline-3-carboxamide;
1-(4-fluorophenyl)-6-((6-methylpyridin-3-yl)methoxy)-4-oxo-1,4-dihydroquinoline-3-carboxamide;
1-(3-methylisothiazol-5-yl)-6-(2-(2-methylpyrimidin-5-yl)ethyl)-4-oxo-1,4-dihydroquinoline-3-carboxamide;
1-(4-fluorophenyl)-4-oxo-6-(1-(pyridin-4-yl)ethoxy)-1,4-dihydroquinoline-3-carboxamide;
1-(4-fluorophenyl)-6-((2-methylpyridin-4-yl)methoxy)-4-oxo-1,4-dihydroquinoline-3-carboxamide;
1-(4-fluorophenyl)-4-oxo-6-(pyridin-4-ylmethoxy)-1,4-dihydroquinoline-3-carboxamide;
1-(4-fluorophenyl)-4-oxo-6-((2-(pyridin-4-yl)ethyl)amino)-1,4-dihydroquinoline-3-carboxamide;
1-(4-fluorophenyl)-4-oxo-6-((2-(pyridin-3-yl)ethyl)amino)-1,4-dihydroquinoline-3-carboxamide;
1-(4-fluorophenyl)-6-((2-morpholinoethyl)amino)-4-oxo-1,4-dihydroquinoline-3-carboxamide;
1-(4-fluorophenyl)-6-((2-methylpyrimidin-5-yl)methoxy)-4-oxo-1,4-dihydroquinoline-3-carboxamide;
1-(4-fluorophenyl)-4-oxo-6-(1-(pyridin-3-yl)ethoxy)-1,4-dihydroquinoline-3-carboxamide;
1-(4-fluorophenyl)-6-(methyl((2-methylpyrimidin-5-yl)methyl)amino)-4-oxo-1,4-dihydroquinoline-3-carboxamide;
1-(4-fluorophenyl)-6-(((3-fluoropyridin-4-yl)oxy)methyl)-4-oxo-1,4-dihydroquinoline-3-carboxamide;
1-(4-fluorophenyl)-6-(((2-methylpyridin-4-yl)oxy)methyl)-4-oxo-1,4-dihydroquinoline-3-carboxamide;
1-(4-fluorophenyl)-4-oxo-6-(((2-(trifluoromethyl)pyridin-4-yl)oxy)methyl)-1,4-dihydroquinoline-3-carboxamide;
1-(4-fluorophenyl)-6-(((2-methylpyrimidin-5-yl)oxy)methyl)-4-oxo-1,4-dihydroquinoline-3-carboxamide;
1-(4-fluorophenyl)-4-oxo-6-(((6-(trifluoromethyl)pyridin-3-yl)oxy)methyl)-1,4-dihydroquinoline-3-carboxamide;
1-(4-fluorophenyl)-4-oxo-6-(((tetrahydro-2H-pyran-4-yl)methyl)amino)-1,4-dihydroquinoline-3-carboxamide;
6-(((6-chloropyridin-3-yl)oxy)methyl)-1-(4-fluorophenyl)-4-oxo-1,4-dihydroquinoline-3-carboxamide;
1-(4-fluorophenyl)-4-oxo-6-(2-(pyridin-3-yl)piperidin-1-yl)-1,4-dihydroquinoline-3-carboxamide;
1-(4-fluorophenyl)-6-(((2-fluoropyridin-3-yl)oxy)methyl)-4-oxo-1,4-dihydroquinoline-3-carboxamide;
1-(4-fluorophenyl)-4-oxo-6-(2-(pyridin-3-yl)pyrrolidin-1-yl)-1,4-dihydroquinoline-3-carboxamide;
1-(4-fluorophenyl)-6-(((6-methylpyridin-3-yl)oxy)methyl)-4-oxo-1,4-dihydroquinoline-3-carboxamide;
6-(ethyl(pyridin-3-ylmethyl)amino)-1-(4-fluorophenyl)-4-oxo-1,4-dihydroquinoline-3-carboxamide;
1-(4-fluorophenyl)-4-oxo-6-(5H-pyrrolo[3,4-b]pyridin-6(7H)-yl)-1,4-dihydroquinoline-3-carboxamide;
1-(4-fluorophenyl)-4-oxo-6-(pyridin-3-ylmethoxy)-1,4-dihydroquinoline-3-carboxamide;
1-(4-fluorophenyl)-6-(methyl(pyridin-3-ylmethyl)amino)-4-oxo-1,4-dihydroquinoline-3-carbonitrile;
1-(4-fluorophenyl)-6-(((6-fluoropyridin-3-yl)oxy)methyl)-4-oxo-1,4-dihydroquinoline-3-carboxamide;
1-(4-fluorophenyl)-4-oxo-6-(2-(2-(trifluoromethyl)pyridin-4-yl)ethyl)-1,4-dihydroquinoline-3-carboxamide;
1-(4-fluorophenyl)-4-oxo-6-(2-(6-(trifluoromethyl)pyridin-3-yl)ethyl)-1,4-dihydroquinoline-3-carboxamide;
1-(4-fluorophenyl)-6-(2-(5-fluoropyridin-3-yl)ethyl)-4-oxo-1,4-dihydroquinoline-3-carboxamide;
8-fluoro-1-(4-fluorophenyl)-6-(2-(2-methylpyrimidin-5-yl)ethyl)-4-oxo-1,4-dihydroquinoline-3-carboxamide;
1-(4-fluorophenyl)-6-(3-morpholinopyrrolidin-1-yl)-4-oxo-1,4-dihydroquinoline-3-carboxamide;
8-fluoro-1-(4-fluorophenyl)-6-(methyl(pyridin-3-ylmethyl)amino)-4-oxo-1,4-dihydroquinoline-3-carboxamide;
1-(4-fluorophenyl)-6-(1-methyl-1H-pyrazol-4-yl)-4-oxo-1,4-dihydroquinoline-3-carboxamide;

1-(4-fluorophenyl)-6-(2-methylpyrimidin-5-yl)-4-oxo-1,4-dihydroquinoline-3-carboxamide;

1-(4-fluorophenyl)-4-oxo-6-(pyridin-4-yl)-1,4-dihydroquinoline-3-carboxamide;

1-(4-fluorophenyl)-4-oxo-6-(pyridin-3-yl)-1,4-dihydroquinoline-3-carboxamide;

(S)-1-(4-fluorophenyl)-6-((2-methylmorpholino)methyl)-4-oxo-1,4-dihydroquinoline-3-carboxamide;

(R)-1-(4-fluorophenyl)-6-((2-methylmorpholino)methyl)-4-oxo-1,4-dihydroquinoline-3-carboxamide;

6-((2,2-dimethylmorpholino)methyl)-1-(4-fluorophenyl)-4-oxo-1,4-dihydroquinoline-3-carboxamide;

6-(((3,3-difluorocyclobutyl)(methyl)amino)methyl)-8-fluoro-1-(4-fluorophenyl)-4-oxo-1,4-dihydroquinoline-3-carboxamide;

6-((cis-2,6-dimethylmorpholino)methyl)-8-fluoro-1-(4-fluorophenyl)-4-oxo-1,4-dihydroquinoline-3-carboxamide;

8-fluoro-1-(4-fluorophenyl)-6-((2-methylmorpholino)methyl)-4-oxo-1,4-dihydroquinoline-3-carboxamide;

6-((4,4-difluoropiperidin-1-yl)methyl)-8-fluoro-1-(4-fluorophenyl)-4-oxo-1,4-dihydroquinoline-3-carboxamide;

6-((3,3-difluoropyrrolidin-1-yl)methyl)-8-fluoro-1-(4-fluorophenyl)-4-oxo-1,4-dihydroquinoline-3-carboxamide;

7-fluoro-1-(4-fluorophenyl)-6-(methyl(pyridin-3-ylmethyl)amino)-4-oxo-1,4-dihydroquinoline-3-carboxamide; and 7-fluoro-1-(4-fluorophenyl)-6-(2-(2-methylpyrimidin-5-yl)ethyl)-4-oxo-1,4-dihydroquinoline-3-carboxamide;

or a pharmaceutically acceptable salt thereof.

13. A pharmaceutical composition comprising a therapeutically effective amount of the compound of claim 1, or a pharmaceutically acceptable salt thereof, in combination with one or more pharmaceutically acceptable carriers.

\* \* \* \* \*

UNITED STATES PATENT AND TRADEMARK OFFICE
CERTIFICATE OF CORRECTION

PATENT NO. : 9,382,208 B1
APPLICATION NO. : 15/006486
DATED : July 5, 2016
INVENTOR(S) : P. Jeffrey Conn et al.

Page 1 of 1

It is certified that error appears in the above-identified patent and that said Letters Patent is hereby corrected as shown below:

In the claims,

Column 105, line 15, insert the word --or-- between the words "aryl" and "heteroaryl"

Signed and Sealed this
Twentieth Day of September, 2016

Michelle K. Lee
*Director of the United States Patent and Trademark Office*

UNITED STATES PATENT AND TRADEMARK OFFICE
CERTIFICATE OF CORRECTION

PATENT NO. : 9,382,208 B1
APPLICATION NO. : 15/006486
DATED : July 5, 2016
INVENTOR(S) : P. Jeffrey Conn et al.

It is certified that error appears in the above-identified patent and that said Letters Patent is hereby corrected as shown below:

In the Specification

Column 1, Line 16:
Replace the following paragraph:
[[This invention was made with government support under Grant number 5 U54 MH84659-06 awarded by the National Institute of Mental Health (NIMH). The government has certain rights in the invention.]]
With the paragraph:
--This invention was made with government support under Grant Number MH084659, awarded by the National Institutes of Health. The Government has certain rights in the invention.--

Signed and Sealed this
Eleventh Day of July, 2023

Katherine Kelly Vidal
*Director of the United States Patent and Trademark Office*